US010703802B2

(12) United States Patent
Hong et al.

(10) Patent No.: US 10,703,802 B2
(45) Date of Patent: Jul. 7, 2020

(54) COMPOSITION COMPRISING AT LEAST TWO INFLUENZA A VIRUS-NEUTRALIZING-BINDING MOLECULES

(71) Applicant: CELLTRION, INC., Incheon (KR)

(72) Inventors: Seung Suh Hong, Seoul (KR); Shin Jae Chang, Incheon (KR); Ki Sung Kwon, Seoul (KR); Kye Sook Yi, Incheon (KR); Sung Hwan Kim, Incheon (KR); Eun Beom Lee, Seoul (KR); Jae Won Lee, Gyeonggi-do (KR); So Jung Lee, Incheon (KR); Ji Young Shin, Incheon (KR); Myung Sam Cho, Incheon (KR)

(73) Assignee: CELLTRION, INC. (KR)

( * ) Notice: Subject to any disclaimer, the term of this patent is extended or adjusted under 35 U.S.C. 154(b) by 533 days.

(21) Appl. No.: 14/780,682

(22) PCT Filed: Mar. 28, 2014

(86) PCT No.: PCT/KR2014/002691
§ 371 (c)(1),
(2) Date: Sep. 28, 2015

(87) PCT Pub. No.: WO2014/158001
PCT Pub. Date: Oct. 2, 2014

(65) Prior Publication Data
US 2016/0052997 A1 Feb. 25, 2016

(30) Foreign Application Priority Data

Mar. 29, 2013 (KR) .................. 10-2013-0034041
Dec. 2, 2013 (KR) .................. 10-2013-0148247

(51) Int. Cl.
| | | |
|---|---|---|
| *A61K 45/06* | (2006.01) |
| *A61K 31/13* | (2006.01) |
| *C07K 16/10* | (2006.01) |
| *A61K 31/196* | (2006.01) |
| *A61K 31/4965* | (2006.01) |
| *A61K 31/7012* | (2006.01) |
| *G01N 33/569* | (2006.01) |
| *A61K 31/215* | (2006.01) |
| *A61K 47/68* | (2017.01) |
| *A61K 39/00* | (2006.01) |

(52) U.S. Cl.
CPC .......... *C07K 16/1018* (2013.01); *A61K 31/13* (2013.01); *A61K 31/196* (2013.01); *A61K 31/215* (2013.01); *A61K 31/4965* (2013.01); *A61K 31/7012* (2013.01); *A61K 45/06* (2013.01); *A61K 47/6841* (2017.08); *G01N 33/56983* (2013.01); *G01N 33/56994* (2013.01); *A61K 2039/507* (2013.01); *C07K 2317/76* (2013.01); *G01N 2333/11* (2013.01); *G01N 2469/10* (2013.01)

(58) Field of Classification Search
None
See application file for complete search history.

(56) References Cited

U.S. PATENT DOCUMENTS

| | | | | |
|---|---|---|---|---|
| 9,475,861 B2 * | 10/2016 | Chang | ................ | C07K 16/1018 |
| 9,573,991 B2 * | 2/2017 | Chang | ................ | C07K 16/1018 |
| 9,834,594 B2 * | 12/2017 | Chang | ................ | C07K 16/1018 |
| 9,856,312 B2 * | 1/2018 | Chang | ................ | C07K 16/1018 |
| 2010/0086555 A1 * | 4/2010 | Lanzavecchia | .... | C07K 16/1018 |
| | | | | 424/159.1 |

FOREIGN PATENT DOCUMENTS

| | | |
|---|---|---|
| JP | 2011-528901 | 12/2011 |
| KR | 2009-0108508 | 10/2009 |
| KR | 2010-0115346 | 10/2010 |
| KR | 10-2011-0047193 A | 5/2011 |
| KR | 10-2011-0102198 A | 9/2011 |
| KR | 2012-0107512 | 10/2012 |
| KR | 2013-0035916 | 4/2013 |
| WO | WO 2008-054481 A2 | 5/2008 |

(Continued)

OTHER PUBLICATIONS

Du et al., A Critical HA1 Neutralizing Domain of H5N1 Influenza in an Optimal Conformation Induces Strong Cross-Protection, PLoS ONE, Jan. 2013, 8(1).*
Abed et al., The 2009 Pandemic H1N1 D222G Hemagglutinin Mutation Alters Receptor Specificity and Increases Virulence in Mice but Not in Ferrets, The Journal of Infectious Diseases, 2011, vol. 204, pp. 1008-1016.*
Lifely et al., Glycosylation and biological activity of CAMPATH-1H expressed in different cell lines and grown under different culture conditions, 1995, Glycobiology, vol. 5, No. 8, pp. 813-822.*

(Continued)

*Primary Examiner* — Benjamin P Blumel
(74) *Attorney, Agent, or Firm* — Sheridan Ross P.C.

(57) ABSTRACT

The present invention provides a composition comprising at least two influenza A virus-neutralizing binding molecules that bind to an epitope in the stem region of influenza A virus hemagglutinin (HA) protein, the method comprising: i) a first binding molecule capable of neutralizing at least one influenza A virus subtype selected from the group consisting of H1, H2, H5 and H9; ii) a second binding molecule capable of neutralizing at least one influenza A virus subtype selected from the group consisting of H1, H3, H5, H7 and H9. The mixed composition of the present invention can effectively neutralize the multiple influenza subtypes of both phylogenetic group 1 and phylogenetic group 2 and can be used in combination with a chemical compound. Thus, the composition of the present invention is very useful for the prevention and treatment of a disease by influenza virus.

25 Claims, 27 Drawing Sheets
Specification includes a Sequence Listing.

(56) References Cited

FOREIGN PATENT DOCUMENTS

| WO | WO 2009/079259 | 6/2009 |
|----|----|----|
| WO | WO 2010/010466 | 1/2010 |
| WO | WO 2010-047509 A2 | 4/2010 |
| WO | WO 2010/130636 | 11/2010 |
| WO | WO 2011/111966 | 9/2011 |
| WO | WO 2011/117848 | 9/2011 |
| WO | WO 2011-123495 A1 | 10/2011 |
| WO | WO 2013/007770 | 1/2013 |
| WO | WO 2013/011347 | 1/2013 |
| WO | WO 2013/048153 | 4/2013 |

OTHER PUBLICATIONS

Chen et al., Human monoclonal antibdoes targeting the haemagglutinin glycoprotein can neutralize H7N9 influenza virus, 2015, Nature Communications, vol. 6.*

International Search Report prepared by the Korean Intellectual Property Office dated Jul. 1, 2014, for International Application No. PCT/KR2014/002691.

Bruhns "Properties of mouse and human IgG receptors and their contribution to disease models," Blood, Jun. 2012, vol. 119, No. 24, pp. 5640-5649.

Cheung et al. "Biology of Influenza A Virus," Annals of the New York Academy of Sciences, Apr. 2007, vol. 1102, pp. 1-25.

Corti et al. "A Neutralizing Antibody Selected from Plasma Cells That Binds to Group 1 and Group 2 Influenza A Hemagglutinins," Science, Aug. 2011, vol. 333, No. 6044, pp. 850-856.

Ekiert et al. "A Highly Conserved Neutralizing Epitope on Group 2 Influenza A Viruses," Science, Aug. 2011, vol. 33, No. 6044, pp. 843-850.

Jin_et al. "A rapid and efficient single-cell manipulation method for screening antigen-specific antibody-secreting cells from human peripheral blood," Nature Medicine, Sep. 2009, vol. 15, No. 9, pp. 1088-1092.

Kenny "Immunochemical Methods in Cell and Molecular Biology: R J Mayer and J H Walker, pp. 325, Academic Press, London, 1987," Biochemical Education, Jul. 1989, vol. 17, No. 3, p. 164.

Luke et al. "Meta-Analysis: Convalescent Blood Products for Spanish Influenza Pneumonia: A Future H5N1 Treatment?" Annals of Internal Medicine, Oct. 2006, vol. 145, No. 8, pp. 599-609.

Palmer, Jr. et al. "Spatially Resolved, Quantitative Determination of Luciferase Activity by Photon-Counting Mircoscopy," Methods in Enzymology, Academic Press, 1999, Ed. Ron J. Doyle, vol. 310, pp. 152-160.

Simmons et al. "Prophylactic and Therapeutic Efficacy of Human Monoclonal Antibodies against H5N1 Influenza," PLoS Medicine, May 2007, vol. 4, No. 5, e178, 9 pages.

Sui et al. "Structural and functional bases for broad-spectrum neutralization of avian and human influenza A viruses," Nature Structural & Molecular Biology, Mar. 2009, vol. 16, No. 3, pp. 265-273.

Throsby et al. "Heterosubtypic Neutralizing Monoclonal Antibodies Cross-Protective against H5N1 and H1N1 Recovered from Human IgM+ Memory B Cells," PLoS ONE, Dec. 2008, vol. 3, No. 12, e3942, 15 pages.

Tong et al. "A distinct lineage of influenza A virus from bats," PNAS, Mar. 2012, vol. 109, No. 11, pp. 4269-4274.

Treanor "Influenza Vaccine—Outmaneuvering Antigenic Shift and Drift," New England Journal of Medicine, Jan. 2004, vol. 350, No. 3, pp. 218-220.

Wrammert et al. "Broadly cross-reactive antibodies dominate the human B cell response against 2009 pandemic H1N1 influenza virus infection," The Journal of Experimental Medicine, Jan. 2011, vol. 208, No. 1, pp. 181-193.

Official Action for Canada Patent Application No. 2,902,147, dated Jun. 20, 2017, 4 pages.

Cho "Development of Human Monoclonal Antibodies Neutralizing Influenza Viruses belonging to Group 1 and 2 of Influenza A," Korean Biotechnology Conference, Apr. 2012, p. 76.

Ma "What is the history of the H3 numbering system?" Jun. 16, 2014, 10 pages [retrieved online from: www.ericmajinglong.com/2014/06/16/what-is-the-history-of-the-h3-numbering-system/].

Nabel et al. "Induction of unnatural immunity: prospects for a broadly protective universal influenza vaccine," Nature Medicine, Dec. 2010, vol. 16, No. 12, pp. 1389-1391.

Raju "Terminal sugars of Fc glycans influence antibody effector functions of IgGs," Current Opinion in Immunology, 2008, vol. 20, pp. 471-478.

Raju "Glycosylation Variations with Expression Systems and Their Impact on Biological Activity of Therapeutic Immunoglobulins," BioProcess International, Apr. 2003, pp. 44-53.

* cited by examiner

[Figure 1]
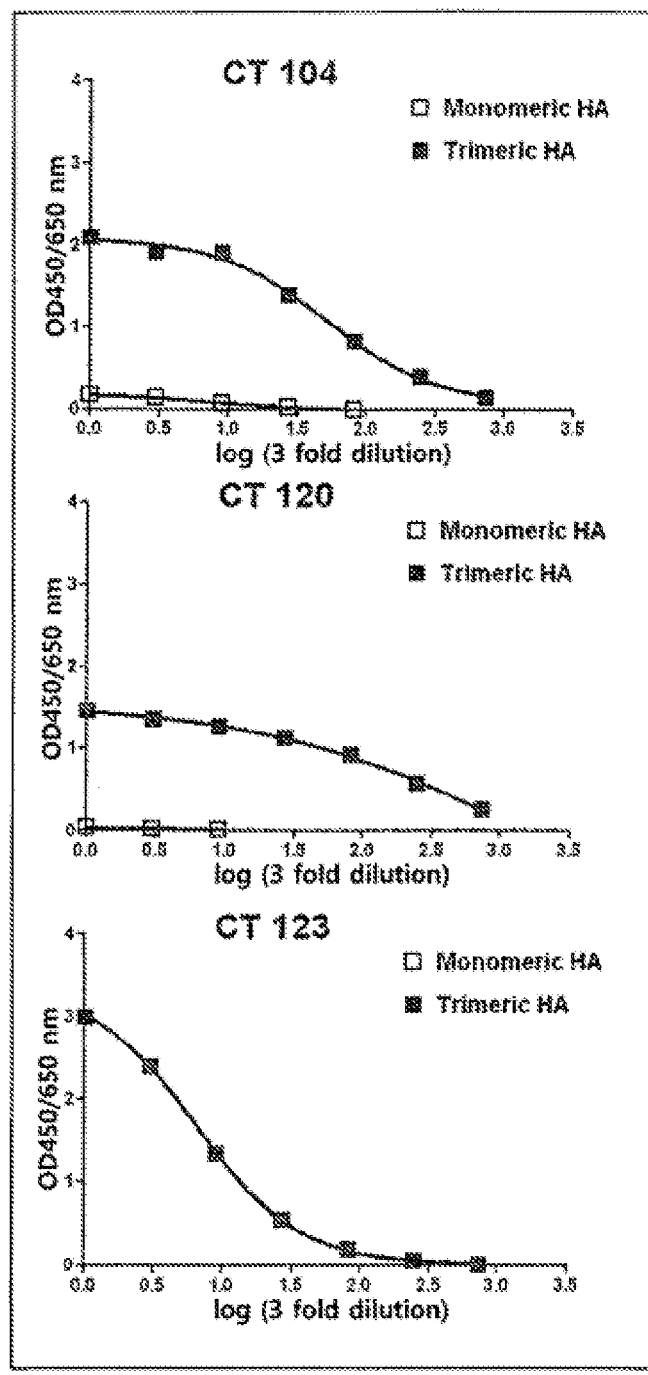

[Figure 2]
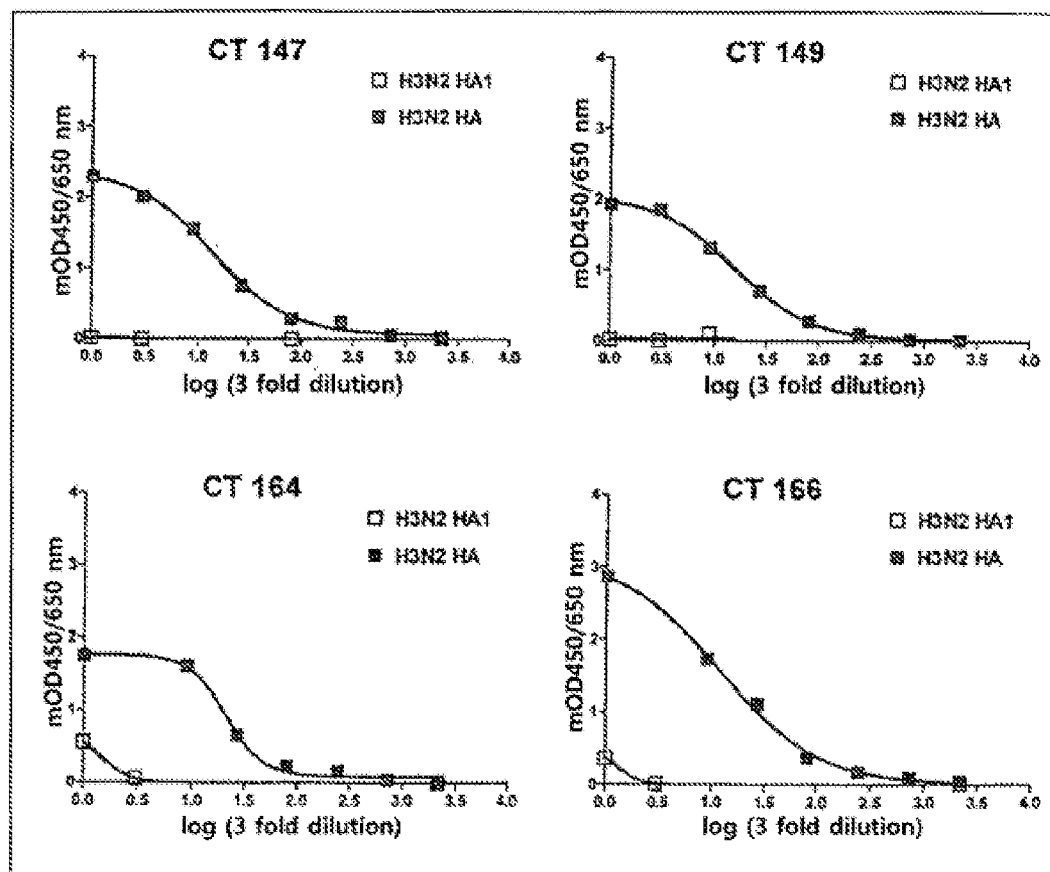

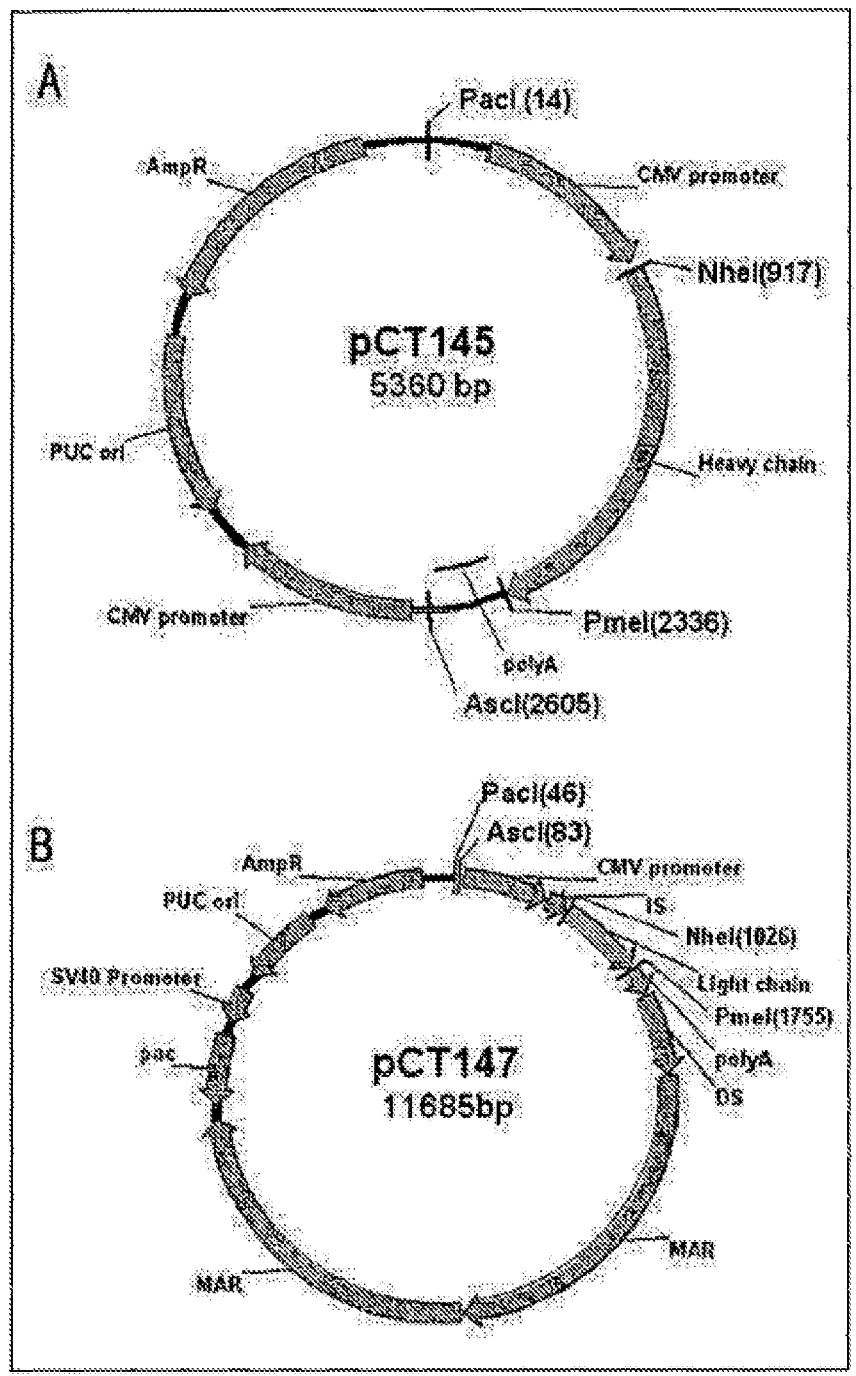
[Figure 3]

【Figure 4】
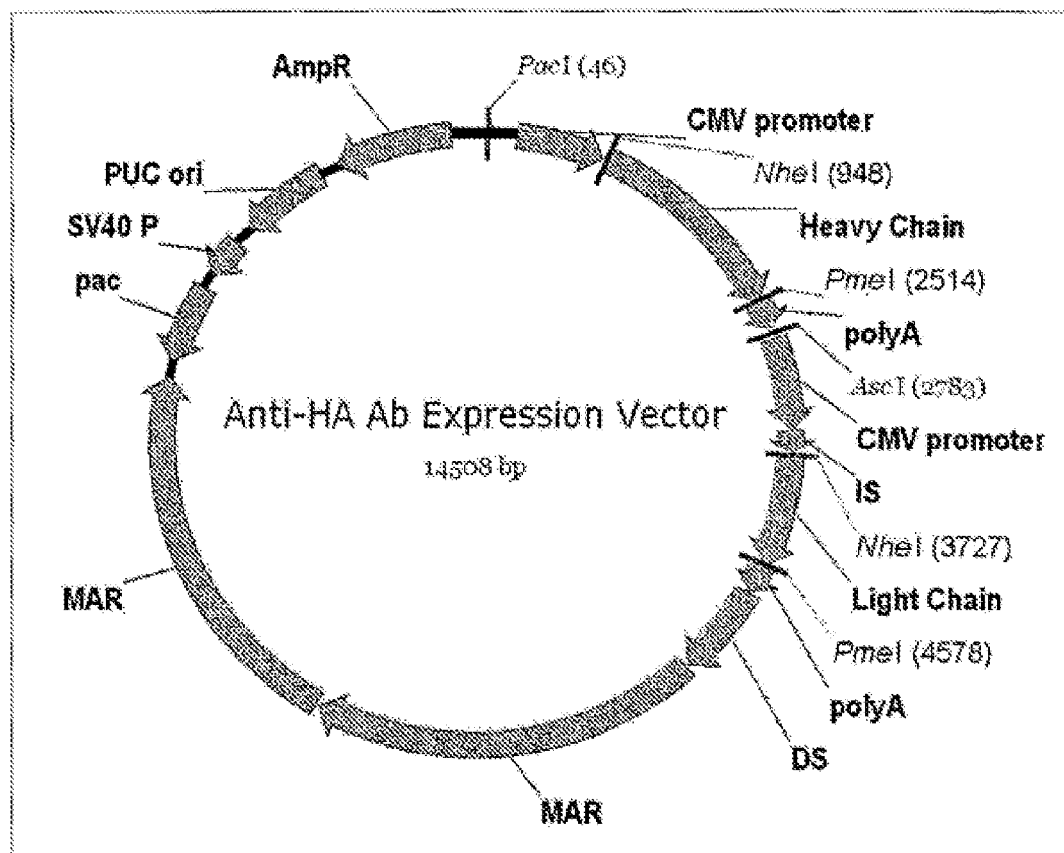

[Figure 5a]
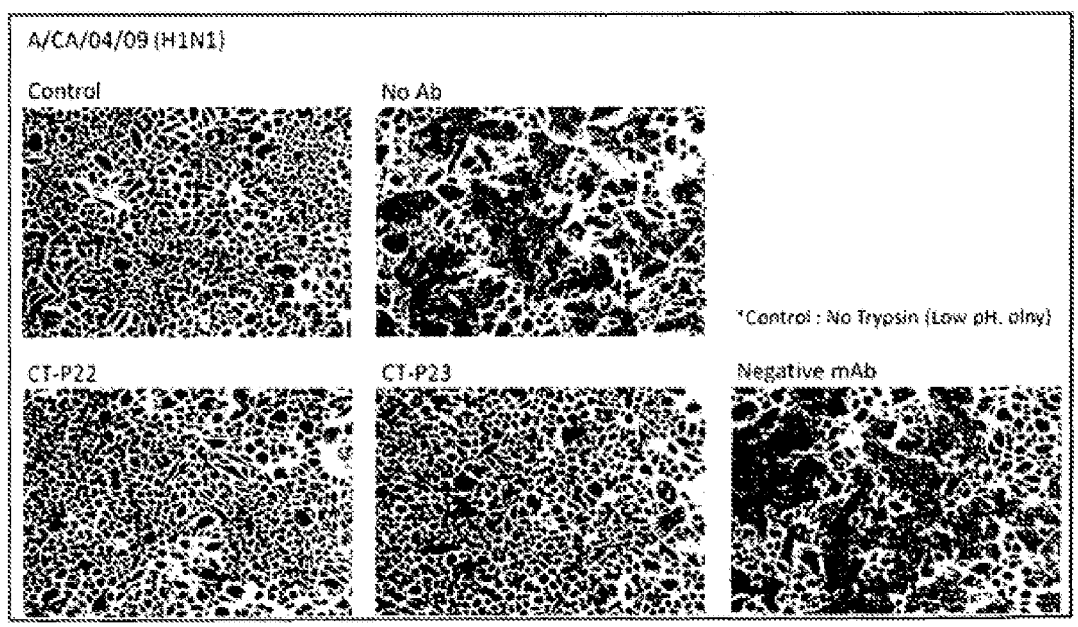

[Figure 5b]
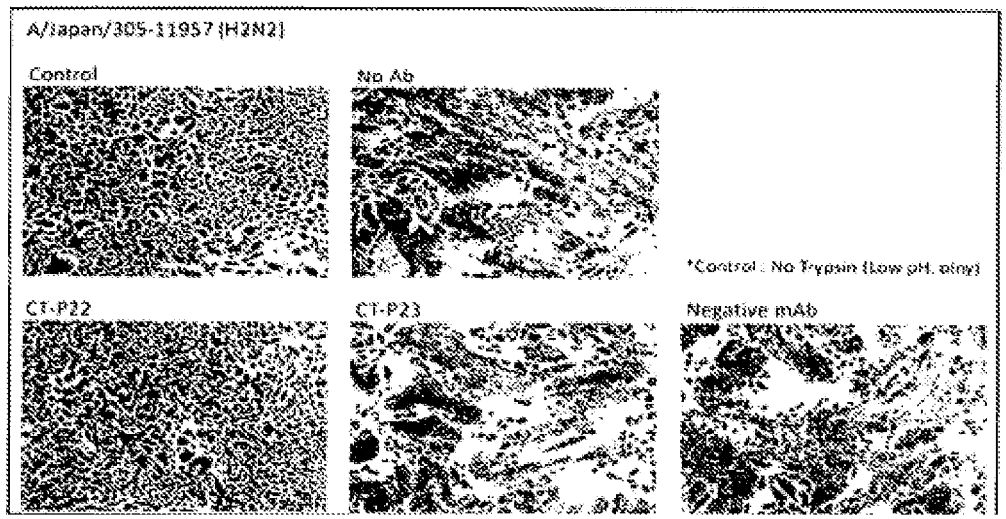

[Figure 5c]
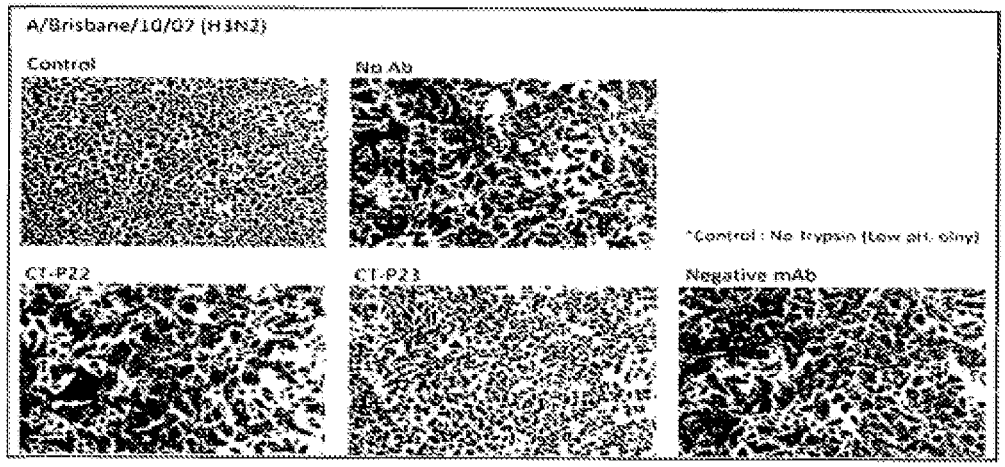

[Figure 5d]
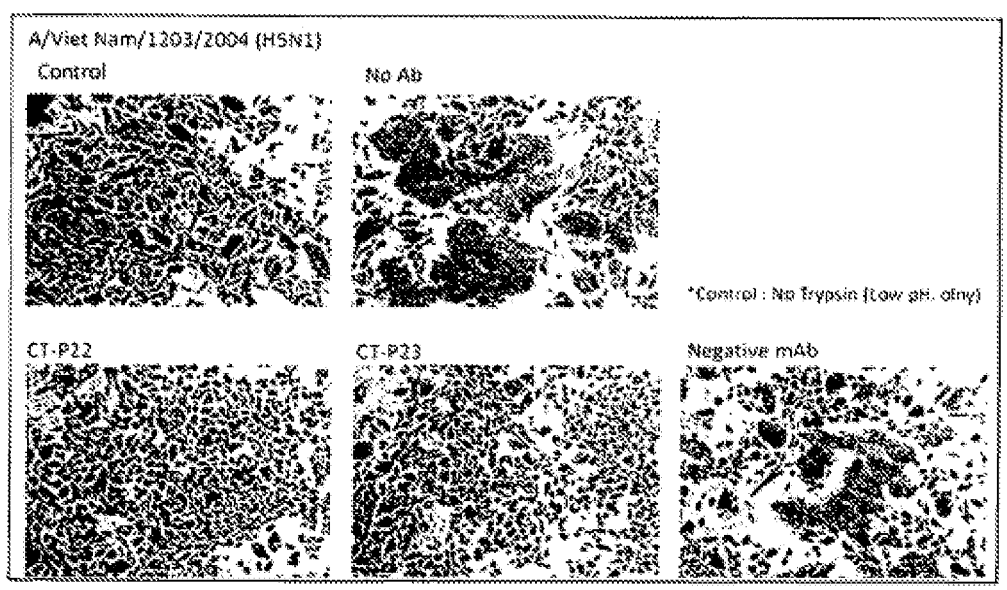

【Figure 6a】
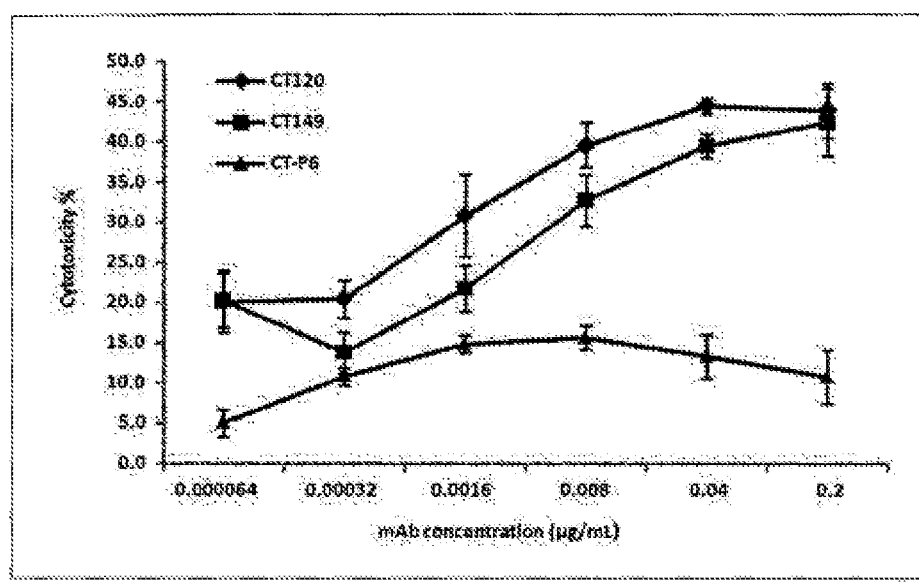

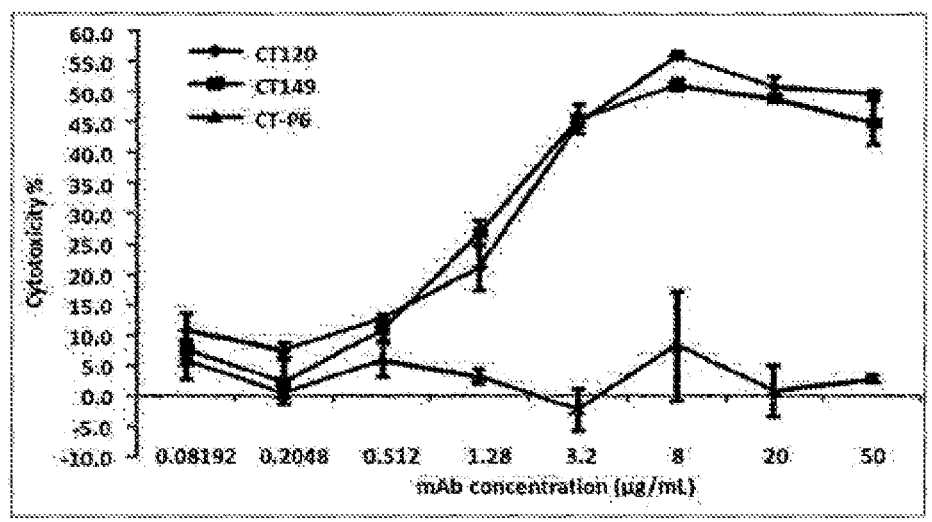
[Figure 6b]

【Figure 7】
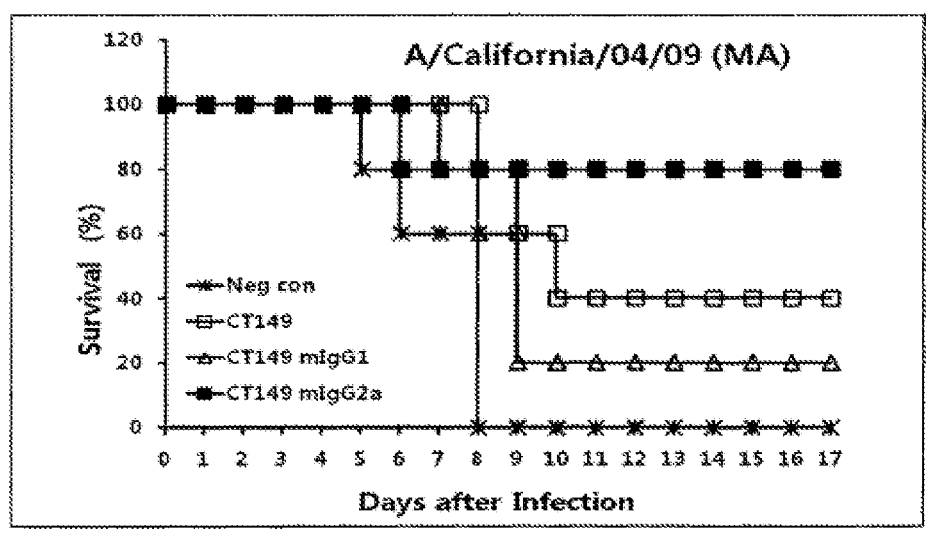

【Figure 8a】
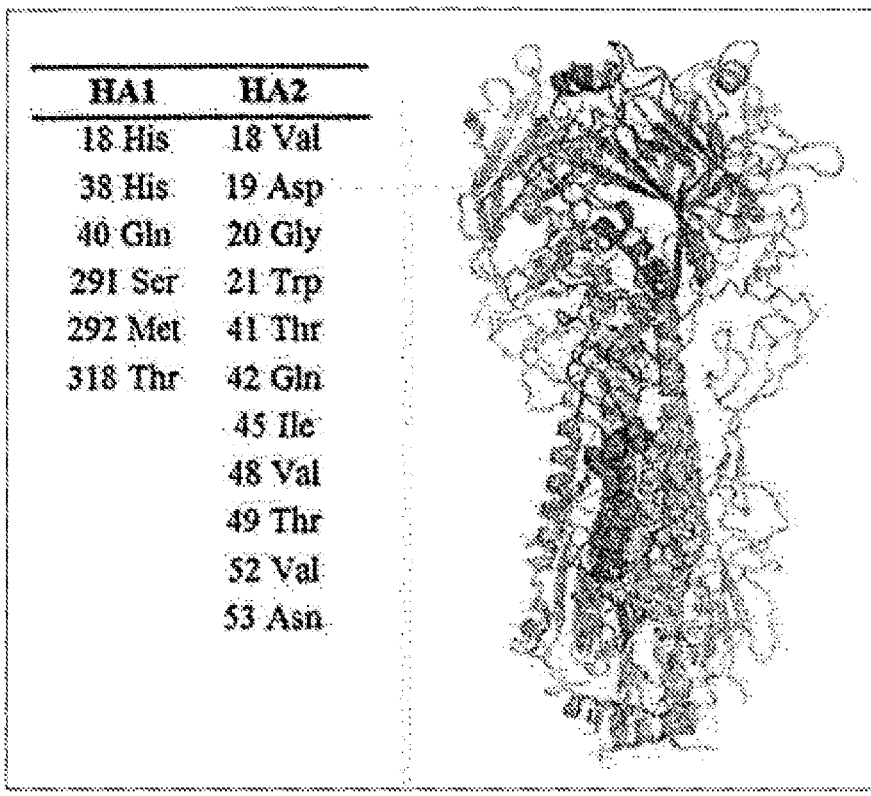

[Figure 8b]

[Figure 8c]
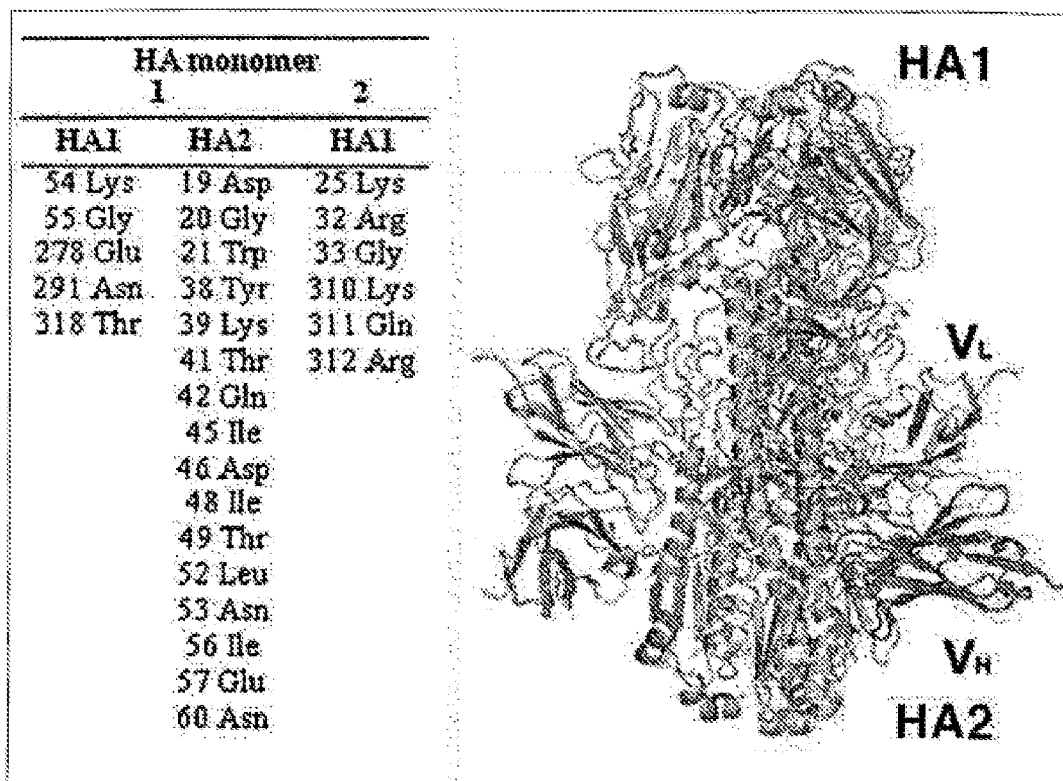

[Figure 9]
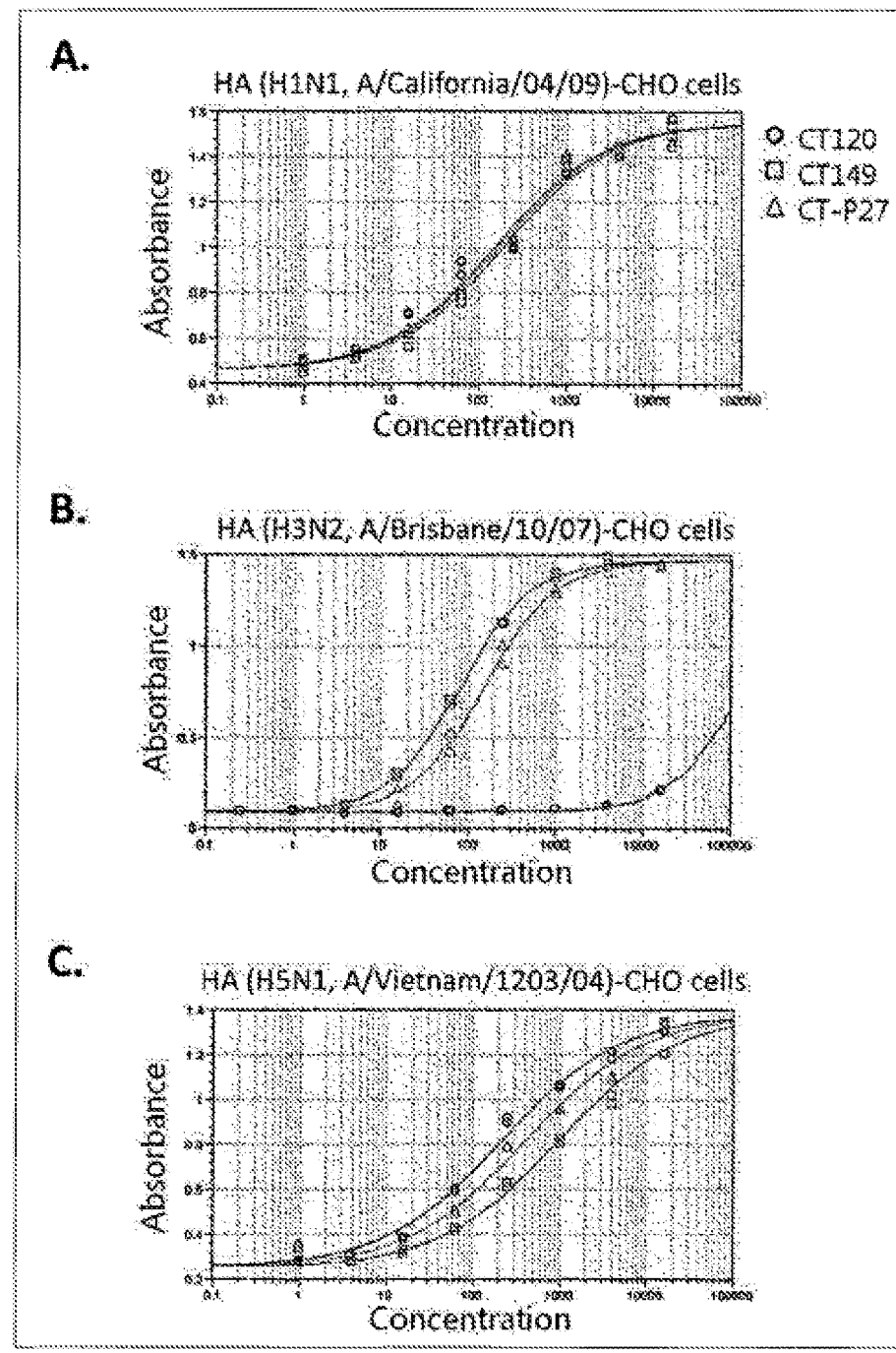

[Figure 10]
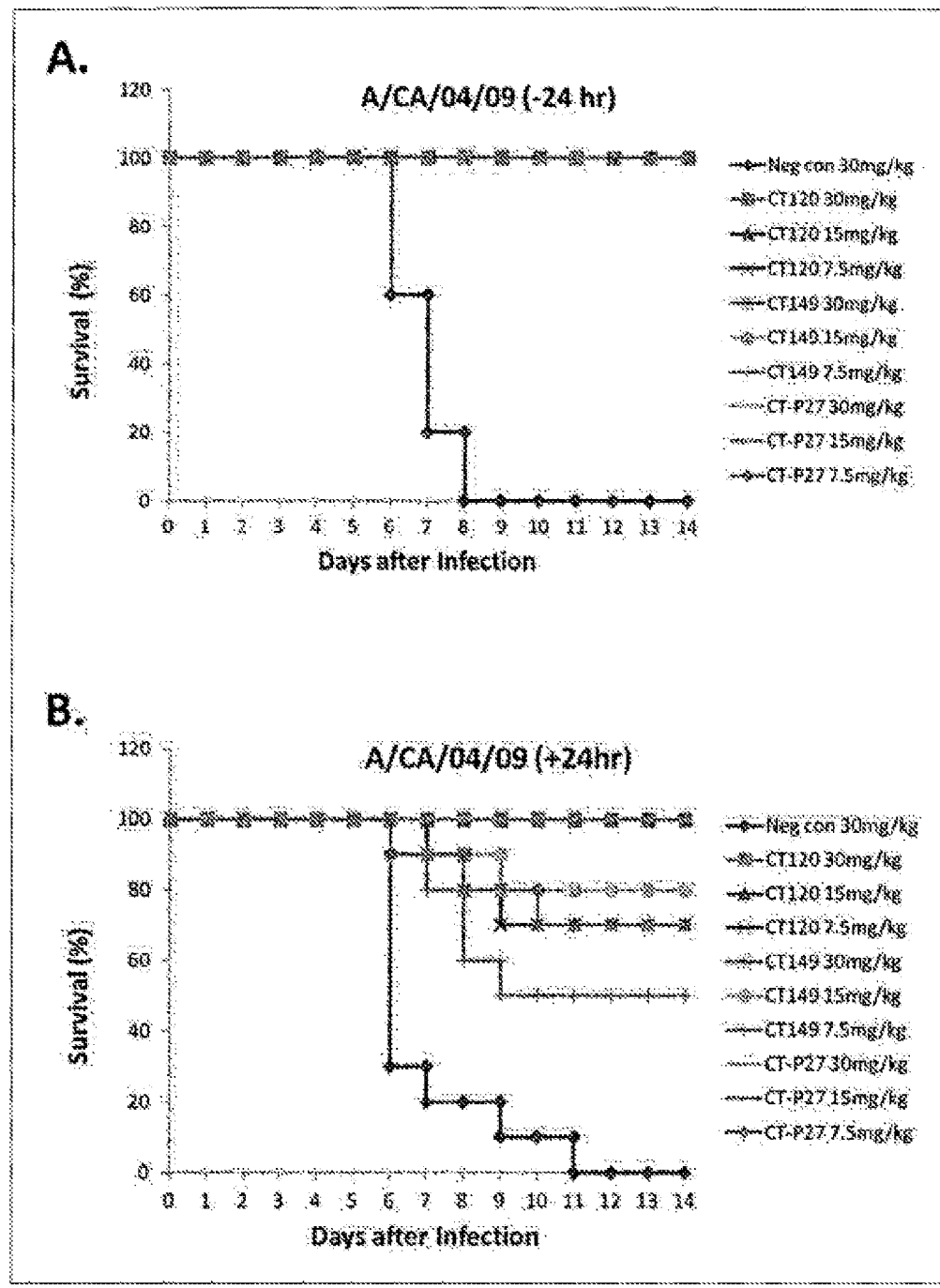

[Figure 11]
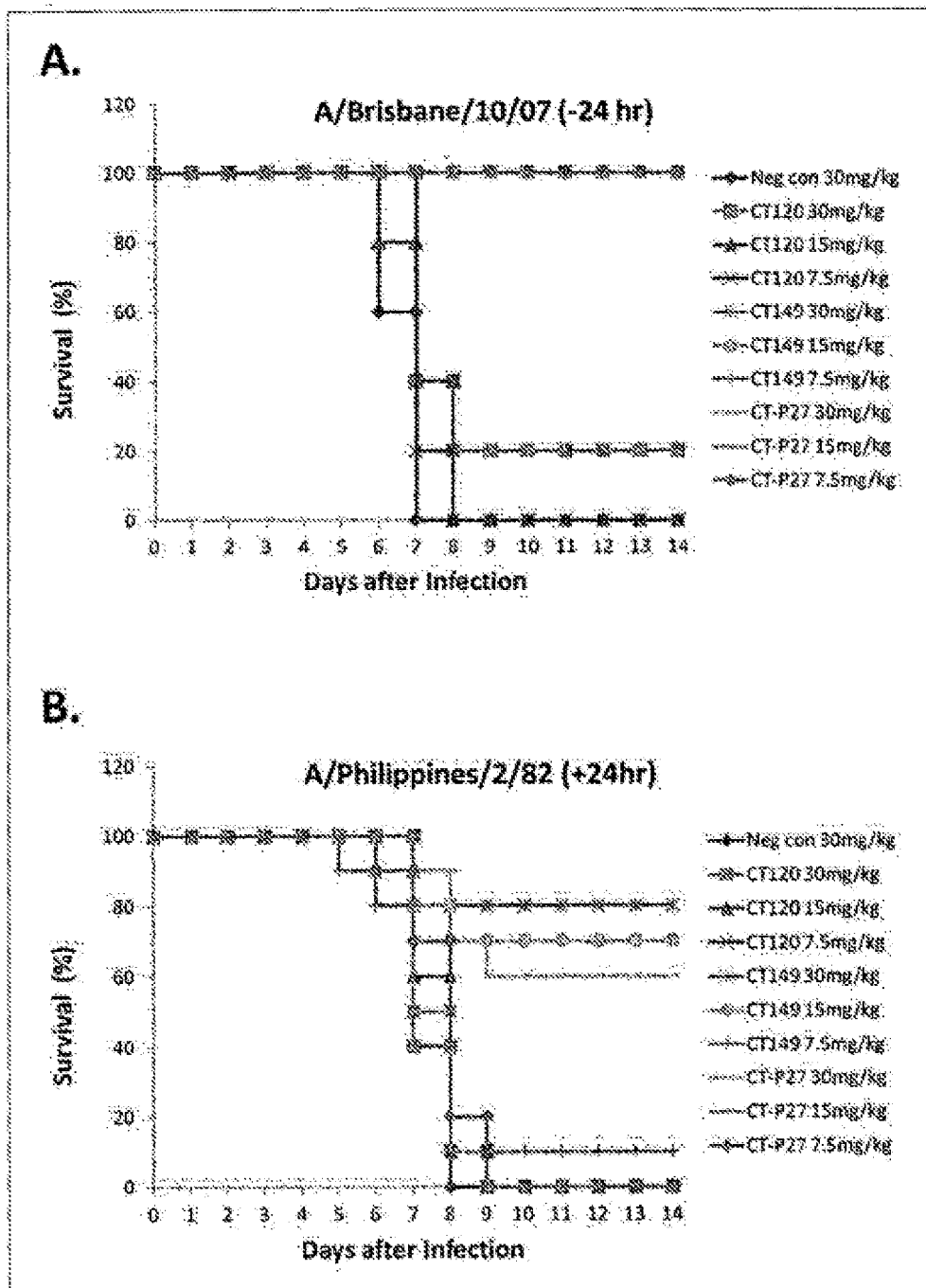

[Figure 12]
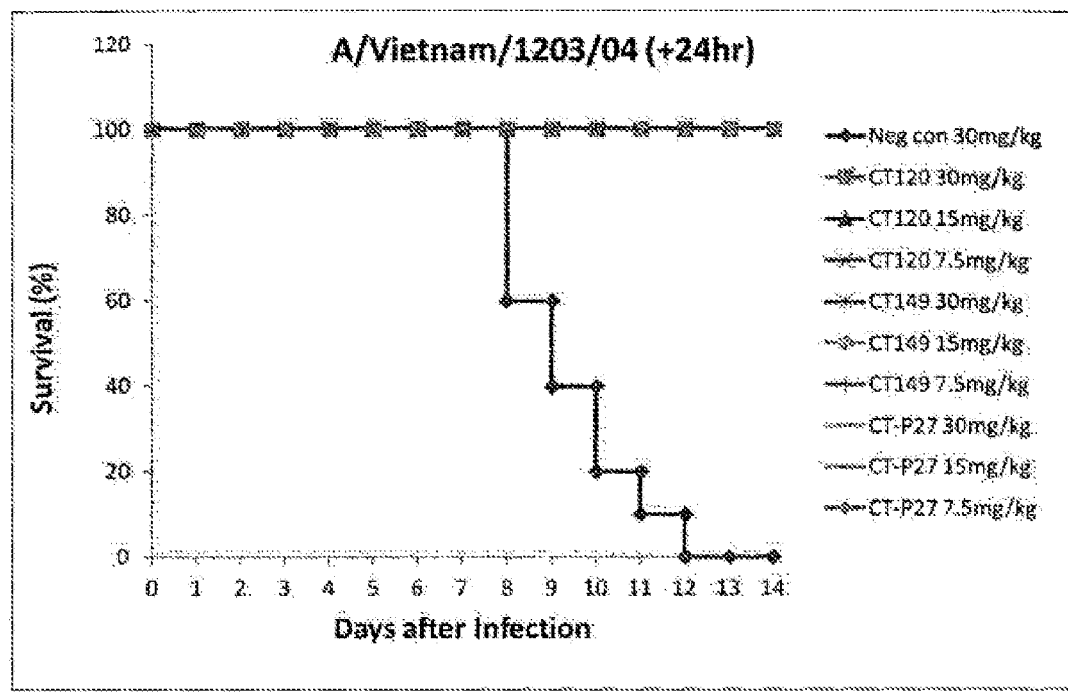

[Figure 13]
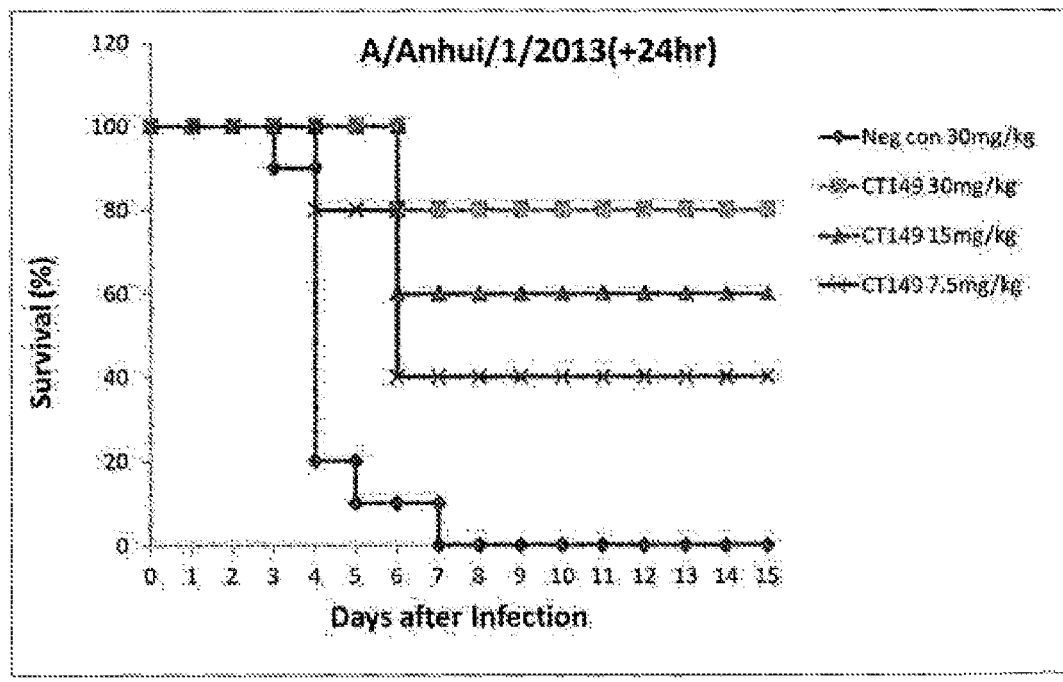

[Figure 14]
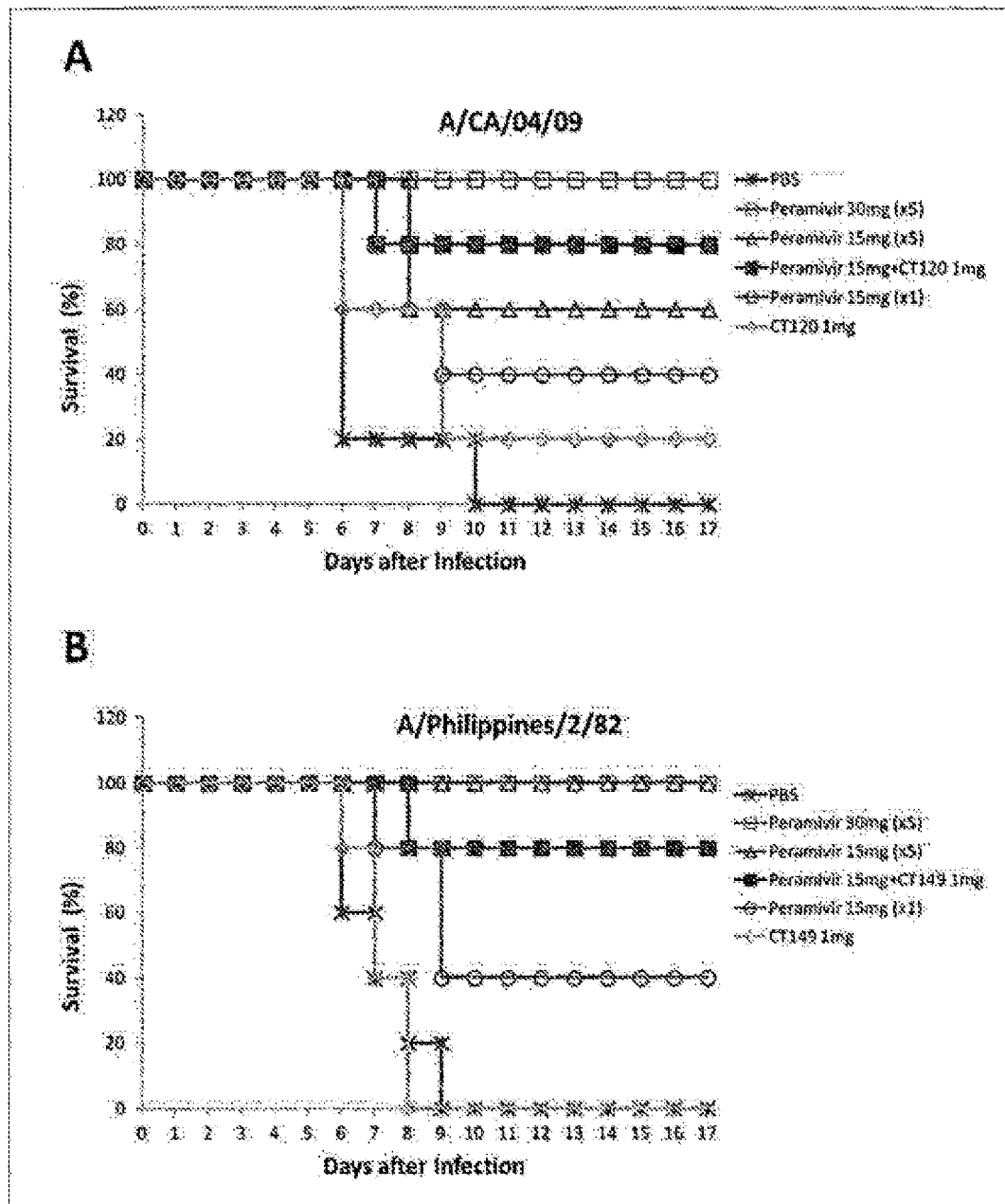

【Figure 15】
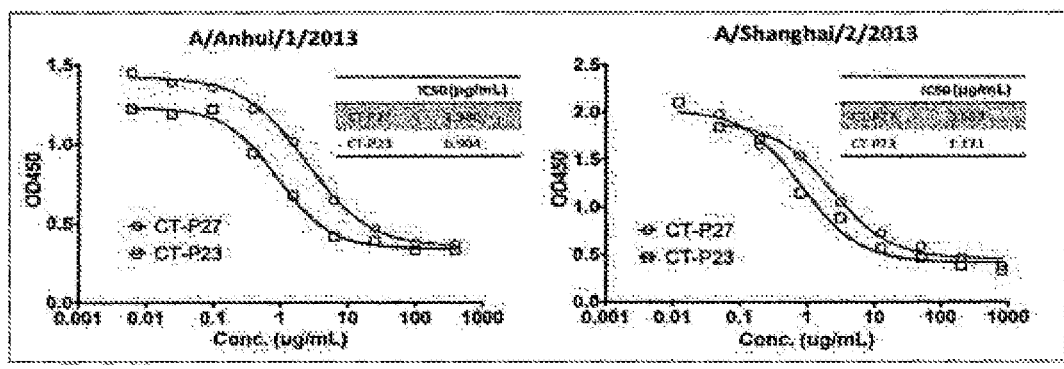

[Figure 16a]
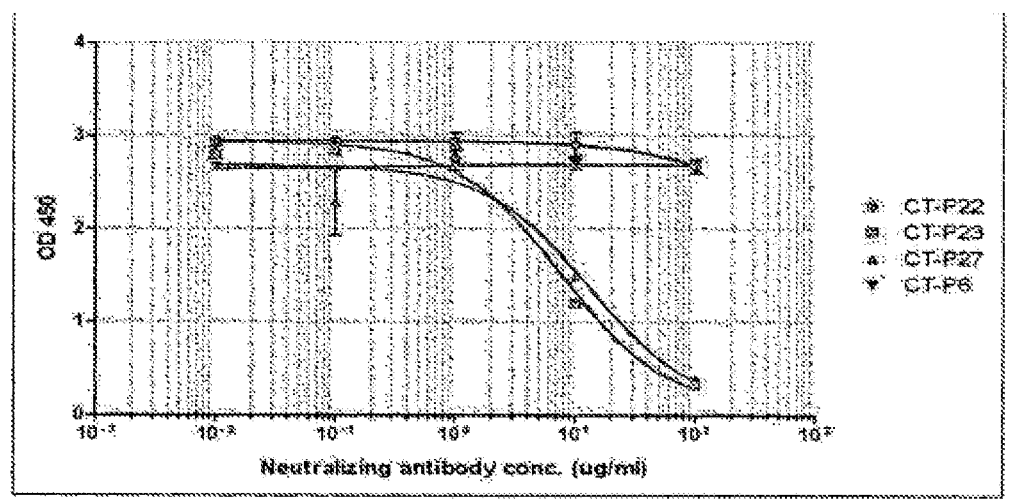

[Figure 16b]
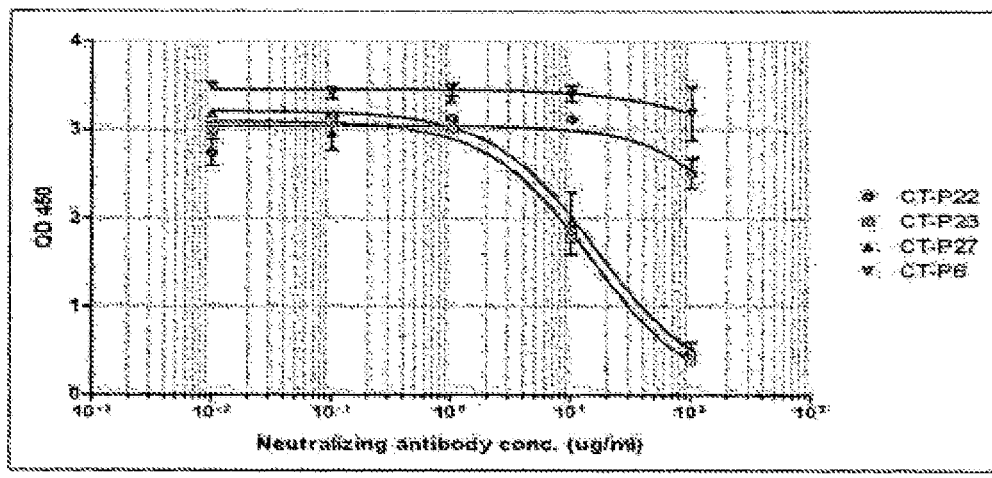

【Figure 17a】
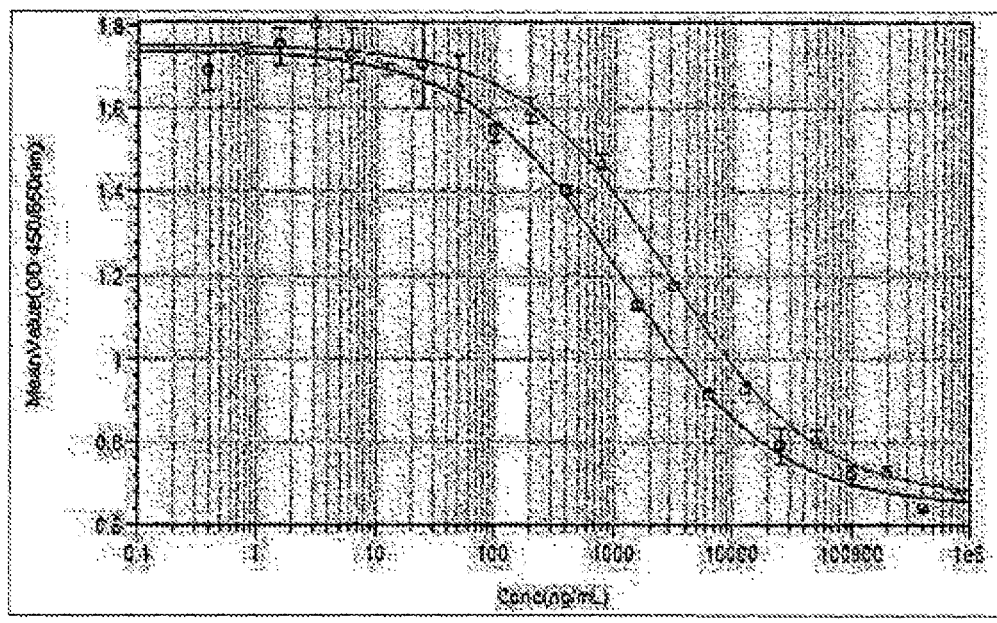

[Figure 17b]
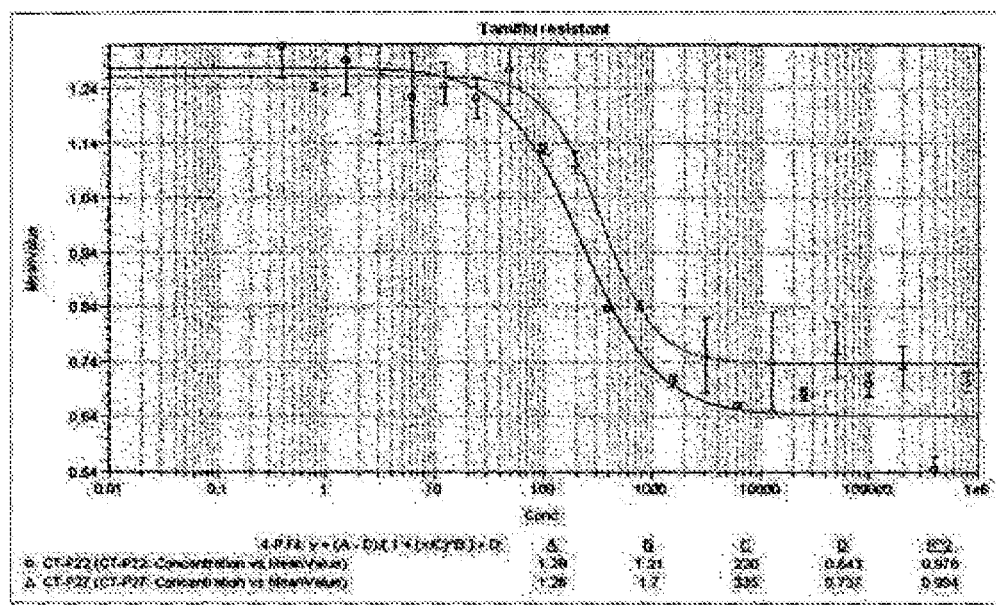

[Figure 18a]
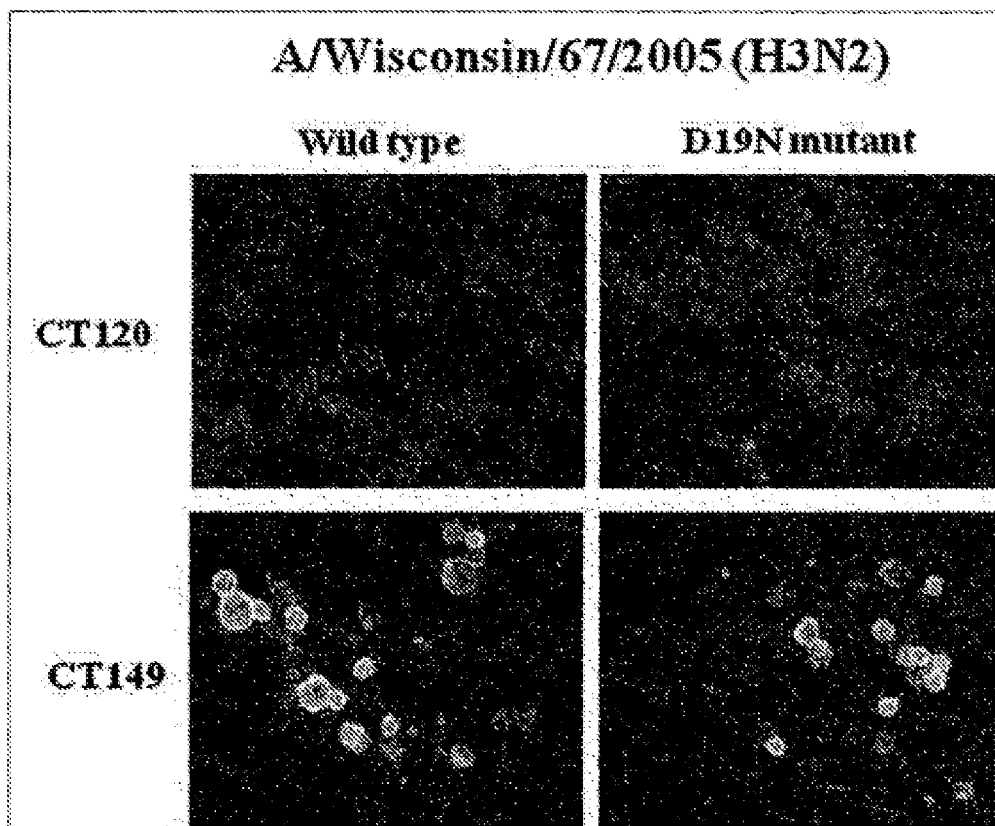

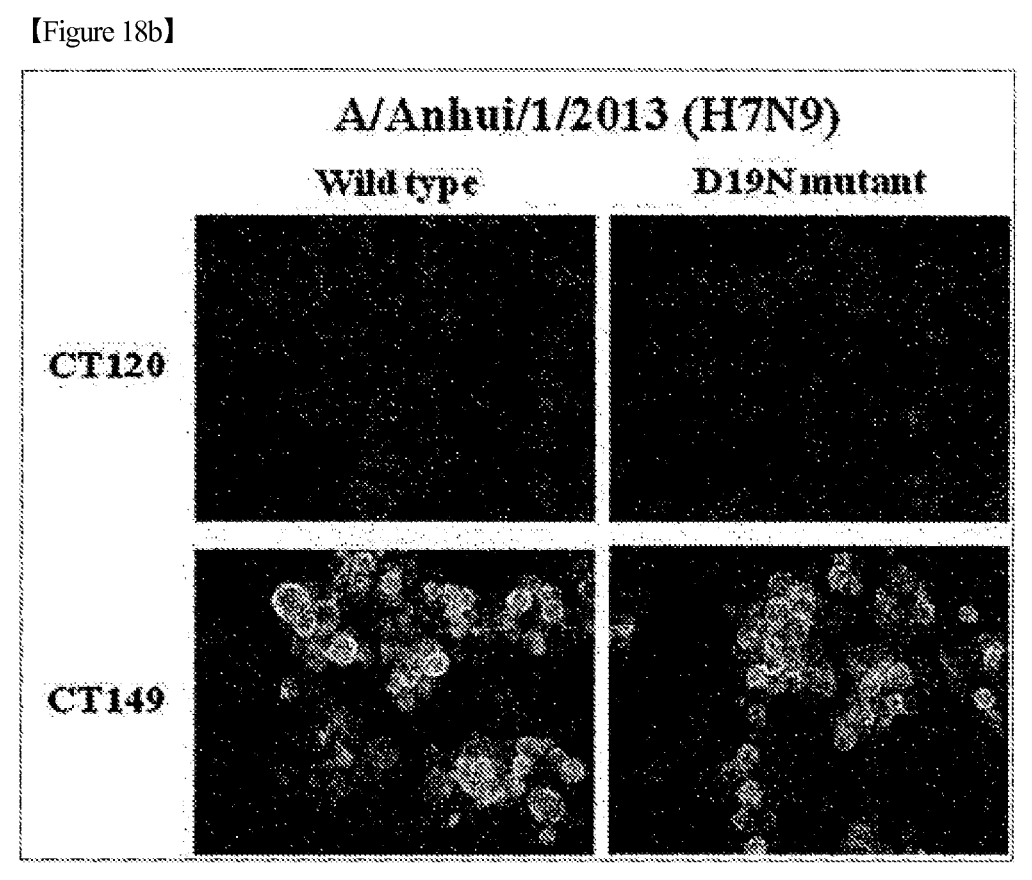

【Figure 18b】

SEQUENCE LISTING

```
<160> NUMBER OF SEQ ID NOS: 112

<210> SEQ ID NO 1
<211> LENGTH: 12
<212> TYPE: PRT
<213> ORGANISM: Artificial Sequence
<220> FEATURE:
<223> OTHER INFORMATION: CT104 light chain CDR1
```

```
<400> SEQUENCE: 1

Arg Ala Ser Gln Ser Leu Ser Ser Ser Leu Val
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CT104 light chain CDR2

<400> SEQUENCE: 2

Gly Ala Ser Ser Arg Ala Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CT104 light chain CDR3

<400> SEQUENCE: 3

Gln Gln Tyr Gly Asn Ser Pro Tyr Thr
1               5

<210> SEQ ID NO 4
<211> LENGTH: 6
<212> TYPE: PRT
<213> ORGANISM: Artificial Sequence
<220> FEATURE:
<223> OTHER INFORMATION: CT104 heavy chain CDR1

<400> SEQUENCE: 4

Asn Asn Tyr Ala Ile Ser
1               5

<210> SEQ ID NO 5
<211> LENGTH: 18
<212> TYPE: PRT
<213> ORGANISM: Artificial Sequence
<220> FEATURE:
<223> OTHER INFORMATION: CT104 heavy chain CDR2

<400> SEQUENCE: 5

Gly Gly Ile Ser Pro Ile Phe Gly Thr Leu Asn Tyr Ala Glu Arg Phe
1               5                   10                  15

Gln Gly

<210> SEQ ID NO 6
<211> LENGTH: 11
<212> TYPE: PRT
<213> ORGANISM: Artificial Sequence
<220> FEATURE:
<223> OTHER INFORMATION: CT104 heavy chain CDR3

<400> SEQUENCE: 6

Gly Cys Gly Tyr Asn Cys Tyr Tyr Phe Asp Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: CT120 light chain CDR1
```

<400> SEQUENCE: 7

Arg Ala Ser Glu Asn Ile Trp Asn Asn Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CT120 light chain CDR2

<400> SEQUENCE: 8

Gly Ala Ser Thr Gly Ala Thr
1               5

<210> SEQ ID NO 9
<211> LENGTH: 9
<212> TYPE: PRT
<213> ORGANISM: Artificial Sequence
<220> FEATURE:
<223> OTHER INFORMATION: CT120 light chain CDR3

<400> SEQUENCE: 9

Gln Gln Tyr Asn Ser Trp Pro Arg Thr
1               5

<210> SEQ ID NO 10
<211> LENGTH: 5
<212> TYPE: PRT
<213> ORGANISM: Artificial Sequence
<220> FEATURE:
<223> OTHER INFORMATION: CT120 heavy chain CDR1

<400> SEQUENCE: 10

Ser His Ala Ile Ser
1               5

<210> SEQ ID NO 11
<211> LENGTH: 17
<212> TYPE: PRT
<213> ORGANISM: Artificial Sequence
<220> FEATURE:
<223> OTHER INFORMATION: CT120 heavy chain CDR2

<400> SEQUENCE: 11

Gly Ile Ser Pro Met Phe Gly Thr Thr His Tyr Ala Gln Lys Phe Gln
1               5                   10                  15

Gly

<210> SEQ ID NO 12
<211> LENGTH: 14
<212> TYPE: PRT
<213> ORGANISM: Artificial Sequence
<220> FEATURE:
<223> OTHER INFORMATION: CT120 heavy chain CDR3

<400> SEQUENCE: 12

Asp Gly Ala Gly Ser Tyr Tyr Pro Leu Asn Trp Phe Asp Pro
1               5                   10

<210> SEQ ID NO 13
<211> LENGTH: 12
<212> TYPE: PRT
<213> ORGANISM: Artificial Sequence
<220> FEATURE:

<223> OTHER INFORMATION: CT123 light chain CDR1

<400> SEQUENCE: 13

Arg Ala Ser Gln Ser Val Ser Ile Ser Tyr Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: CT123 light chain CDR2

<400> SEQUENCE: 14

Gly Ala Ser Arg Arg Ala Thr
1               5

<210> SEQ ID NO 15
<211> LENGTH: 9
<212> TYPE: PRT
<213> ORGANISM: Artificial Sequence
<220> FEATURE:
<223> OTHER INFORMATION: CT123 light chain CDR3

<400> SEQUENCE: 15

Gln Gln Tyr Gly Ser Ser Pro Tyr Thr
1               5

<210> SEQ ID NO 16
<211> LENGTH: 5
<212> TYPE: PRT
<213> ORGANISM: Artificial Sequence
<220> FEATURE:
<223> OTHER INFORMATION: CT123 heavy chain CDR1

<400> SEQUENCE: 16

Arg Phe Gly Ile His
1               5

<210> SEQ ID NO 17
<211> LENGTH: 17
<212> TYPE: PRT
<213> ORGANISM: Artificial Sequence
<220> FEATURE:
<223> OTHER INFORMATION: CT123 heavy chain CDR2

<400> SEQUENCE: 17

Val Ile Trp Tyr Asp Gly Ser Asn Lys Phe Tyr Ala Asp Ser Val Lys
1               5                   10                  15

Gly

<210> SEQ ID NO 18
<211> LENGTH: 18
<212> TYPE: PRT
<213> ORGANISM: Artificial Sequence
<220> FEATURE:
<223> OTHER INFORMATION: CT123 heavy chain CDR3

<400> SEQUENCE: 18

Asp Ser Arg Gly Tyr Cys Ser Ser Ile Ile Cys Phe Glu Gly Gly Leu
1               5                   10                  15

Asp Asn

<210> SEQ ID NO 19
<211> LENGTH: 12

```
<212> TYPE: PRT
<213> ORGANISM: Artificial Sequence
<220> FEATURE:
<223> OTHER INFORMATION: CT147 light chain CDR1

<400> SEQUENCE: 19

Arg Ala Ser Arg Arg Val Gly Ser Thr Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: CT147 light chain CDR2

<400> SEQUENCE: 20

Gly Ala Ser Ser Arg Ala Ala
1               5

<210> SEQ ID NO 21
<211> LENGTH: 9
<212> TYPE: PRT
<213> ORGANISM: Artificial Sequence
<220> FEATURE:
<223> OTHER INFORMATION: CT147 light chain CDR3

<400> SEQUENCE: 21

Gln Gln Tyr Ala Ala Ser Pro Trp Thr
1               5

<210> SEQ ID NO 22
<211> LENGTH: 5
<212> TYPE: PRT
<213> ORGANISM: Artificial Sequence
<220> FEATURE:
<223> OTHER INFORMATION: CT147 heavy chain CDR1

<400> SEQUENCE: 22

Thr Tyr Gly Ile Ser
1               5

<210> SEQ ID NO 23
<211> LENGTH: 17
<212> TYPE: PRT
<213> ORGANISM: Artificial Sequence
<220> FEATURE:
<223> OTHER INFORMATION: CT147 heavy chain CDR2

<400> SEQUENCE: 23

Trp Ile Ser Ala Tyr Thr Gly Asn Thr Asp Tyr Ala Gln Lys Val Gln
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: CT147 heavy chain CDR3

<400> SEQUENCE: 24

Asp Lys Val Gln Gly Arg Val Glu Ala Gly Ser Gly Gly Arg His Asp
1               5                   10                  15

Tyr
```

<210> SEQ ID NO 25
<211> LENGTH: 12
<212> TYPE: PRT
<213> ORGANISM: Artificial Sequence
<220> FEATURE:
<223> OTHER INFORMATION: CT149 light chain CDR1

<400> SEQUENCE: 25

Arg Ala Ser His Arg Val Gly Ser Thr Tyr Ile Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: CT149 light chain CDR2

<400> SEQUENCE: 26

Gly Ala Ser Asn Arg Ala Thr
1               5

<210> SEQ ID NO 27
<211> LENGTH: 9
<212> TYPE: PRT
<213> ORGANISM: Artificial Sequence
<220> FEATURE:
<223> OTHER INFORMATION: CT149 light chain CDR3

<400> SEQUENCE: 27

Gln Gln Phe Ser Val Ser Pro Trp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: CT149 heavy chain CDR1

<400> SEQUENCE: 28

Thr Tyr Gly Val Ser
1               5

<210> SEQ ID NO 29
<211> LENGTH: 17
<212> TYPE: PRT
<213> ORGANISM: Artificial Sequence
<220> FEATURE:
<223> OTHER INFORMATION: CT149 heavy chain CDR2

<400> SEQUENCE: 29

Trp Ile Ser Ala Tyr Thr Gly Ile Thr Asp Tyr Ala Gln Lys Phe Gln
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: CT149 heavy chain CDR3

<400> SEQUENCE: 30

Asp Lys Val Gln Gly Arg Val Glu Val Gly Ser Gly Gly Arg His Asp
1               5                   10                  15

-continued

Tyr

<210> SEQ ID NO 31
<211> LENGTH: 12
<212> TYPE: PRT
<213> ORGANISM: Artificial Sequence
<220> FEATURE:
<223> OTHER INFORMATION: CT164 light chain CDR1

<400> SEQUENCE: 31

Arg Ala Ser His Ser Val Gly Ser Thr Tyr Ile Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: CT164 light chain CDR2

<400> SEQUENCE: 32

Gly Ala Ser Asn Arg Ala Thr
1               5

<210> SEQ ID NO 33
<211> LENGTH: 9
<212> TYPE: PRT
<213> ORGANISM: Artificial Sequence
<220> FEATURE:
<223> OTHER INFORMATION: CT164 light chain CDR3

<400> SEQUENCE: 33

Gln Gln Phe Ser Val Ser Pro Trp Thr
1               5

<210> SEQ ID NO 34
<211> LENGTH: 5
<212> TYPE: PRT
<213> ORGANISM: Artificial Sequence
<220> FEATURE:
<223> OTHER INFORMATION: CT164 heavy chain CDR1

<400> SEQUENCE: 34

Thr Tyr Gly Val Ser
1               5

<210> SEQ ID NO 35
<211> LENGTH: 17
<212> TYPE: PRT
<213> ORGANISM: Artificial Sequence
<220> FEATURE:
<223> OTHER INFORMATION: CT164 heavy chain CDR2

<400> SEQUENCE: 35

Trp Ile Ser Gly Tyr Thr Gly Ile Thr Asp Tyr Ala Gln Lys Ser Gln
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: CT164 heavy chain CDR3

<400> SEQUENCE: 36

Asp Lys Val Gln Gly Arg Val Glu Ala Gly Ser Gly Gly Arg His Asp
1               5                   10                  15

Tyr

<210> SEQ ID NO 37
<211> LENGTH: 12
<212> TYPE: PRT
<213> ORGANISM: Artificial Sequence
<220> FEATURE:
<223> OTHER INFORMATION: CT166 light chain CDR1

<400> SEQUENCE: 37

Arg Ala Ser His Ser Ile Gly Ser Thr Tyr Ile Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: CT166 light chain CDR2

<400> SEQUENCE: 38

Gly Ala Ser Asn Arg Ala Ser
1               5

<210> SEQ ID NO 39
<211> LENGTH: 9
<212> TYPE: PRT
<213> ORGANISM: Artificial Sequence
<220> FEATURE:
<223> OTHER INFORMATION: CT166 light chain CDR3

<400> SEQUENCE: 39

Gln Gln Phe Ser Val Ser Pro Trp Thr
1               5

<210> SEQ ID NO 40
<211> LENGTH: 5
<212> TYPE: PRT
<213> ORGANISM: Artificial Sequence
<220> FEATURE:
<223> OTHER INFORMATION: CT166 heavy chain CDR1

<400> SEQUENCE: 40

Thr Tyr Gly Val Ser
1               5

<210> SEQ ID NO 41
<211> LENGTH: 17
<212> TYPE: PRT
<213> ORGANISM: Artificial Sequence
<220> FEATURE:
<223> OTHER INFORMATION: CT166 heavy chain CDR2

<400> SEQUENCE: 41

Trp Ile Ser Gly Tyr Thr Gly Ile Thr Asp Tyr Ala Gln Lys Phe Gln
1               5                   10                  15

Gly

<210> SEQ ID NO 42
<211> LENGTH: 17
<212> TYPE: PRT
<213> ORGANISM: Artificial Sequence
<220> FEATURE:

<223> OTHER INFORMATION: CT166 heavy chain CDR3

<400> SEQUENCE: 42

Asp Lys Val Gln Gly Arg Val Glu Val Gly Ser Gly Gly Arg His Asp
1               5                   10                  15

Tyr

<210> SEQ ID NO 43
<211> LENGTH: 235
<212> TYPE: PRT
<213> ORGANISM: Artificial Sequence
<220> FEATURE:
<223> OTHER INFORMATION: CT104 light chain

<400> SEQUENCE: 43

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Leu Ser Ser Ser Leu Val Trp Tyr Gln Gln Lys Pro Gly Gln Ala
        50                  55                  60

Pro Arg Leu Leu Ile Tyr Gly Ala Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
                100                 105                 110

Gly Asn Ser Pro Tyr Thr Phe Gly Gln Gly Thr Gln Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 44
<211> LENGTH: 469
<212> TYPE: PRT
<213> ORGANISM: Artificial Sequence
<220> FEATURE:
<223> OTHER INFORMATION: CT104 heavy chain

<400> SEQUENCE: 44

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
                20                  25                  30

```
Pro Gly Ser Ser Val Lys Val Ser Cys Lys Ala Ser Gly Gly Thr Leu
         35                  40                  45

Asn Asn Tyr Ala Ile Ser Trp Val Arg Gln Ala Pro Gly Gln Gly Leu
     50                  55                  60

Glu Trp Met Gly Gly Ile Ser Pro Ile Phe Gly Thr Leu Asn Tyr Ala
 65                  70                  75                  80

Glu Arg Phe Gln Gly Arg Val Thr Ile Thr Ala Asp Val Phe Thr Asn
                 85                  90                  95

Thr Val Tyr Met Glu Leu Ser Ser Leu Arg Ser Glu Asp Thr Ala Val
                100                 105                 110

Tyr Phe Cys Ala Arg Gly Cys Gly Tyr Asn Cys Tyr Tyr Phe Asp Gly
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445
```

-continued

```
Val Met His Glu Gly Leu His Asn Pro Tyr Thr Gln Lys Ser Leu Ser
    450                 455                 460

Leu Phe Pro Gly Lys
465

<210> SEQ ID NO 45
<211> LENGTH: 234
<212> TYPE: PRT
<213> ORGANISM: Artificial Sequence
<220> FEATURE:
<223> OTHER INFORMATION: CT120 light chain

<400> SEQUENCE: 45

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Ile Trp Asn Asn Leu Ala Trp Tyr Gln Gln Lys Pro Gly Gln Ala Pro
    50                  55                  60

Arg Leu Leu Ile Ser Gly Ala Ser Thr Gly Ala Thr Gly Val Pro Ser
65                  70                  75                  80

Arg Phe Arg Gly Ser Gly Ser Arg Thr Glu Phe Thr Leu Thr Ile Ser
                85                  90                  95

Ser Leu Gln Ser Glu Asp Phe Ala Ile Tyr Phe Cys Gln Gln Tyr Asn
            100                 105                 110

Ser Trp Pro Arg Thr Phe Gly Pro Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 46
<211> LENGTH: 472
<212> TYPE: PRT
<213> ORGANISM: Artificial Sequence
<220> FEATURE:
<223> OTHER INFORMATION: CT120 heavy chain

<400> SEQUENCE: 46

Met Asp Trp Thr Trp Arg Phe Leu Phe Val Val Ala Ala Ala Thr Gly
1               5                   10                  15

Val Gln Cys Gln Val Gln Leu Val Gln Ser Gly Ala Glu Val Lys Met
            20                  25                  30

Pro Gly Ser Ser Val Lys Val Ser Cys Lys Thr Ser Gly Val Phe Phe
        35                  40                  45
```

```
Ser Ser His Ala Ile Ser Trp Val Arg Gln Ala Pro Gly Gln Gly Leu
     50                  55                  60

Glu Trp Met Gly Gly Ile Ser Pro Met Phe Gly Thr Thr His Tyr Ala
 65                  70                  75                  80

Gln Lys Phe Gln Gly Arg Val Thr Ile Thr Ala Asp Gln Ser Thr Thr
                 85                  90                  95

Thr Ala Tyr Met Glu Leu Thr Ser Leu Thr Ser Glu Asp Thr Ala Val
            100                 105                 110

Tyr Tyr Cys Ala Arg Asp Gly Ala Gly Ser Tyr Tyr Pro Leu Asn Trp
        115                 120                 125

Phe Asp Pro Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Arg Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Gly Leu His Asn His Tyr Thr Gln Lys
    450                 455                 460
```

Ser Leu Ser Leu Phe Pro Gly Lys
465                 470

<210> SEQ ID NO 47
<211> LENGTH: 235
<212> TYPE: PRT
<213> ORGANISM: Artificial Sequence
<220> FEATURE:
<223> OTHER INFORMATION: CT123 light chain

<400> SEQUENCE: 47

Met Glu Thr Pro Ala Gln Leu Leu Phe Leu Leu Leu Trp Leu Pro
1               5                   10                  15

Asp Thr Thr Gly Glu Thr Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ile Ser Tyr Leu Ala Trp Tyr Gln Arg Lys Pro Gly Gln Ala
        50                  55                  60

Pro Arg Leu Leu Ile Tyr Gly Ala Ser Arg Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Tyr Thr Phe Gly Gln Gly Thr Lys Leu Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 48
<211> LENGTH: 476
<212> TYPE: PRT
<213> ORGANISM: Artificial Sequence
<220> FEATURE:
<223> OTHER INFORMATION: CT123 heavy chain

<400> SEQUENCE: 48

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Arg Phe Gly Ile His Trp Val Arg Gln Ala Pro Gly Lys Gly Leu
        50                  55                  60

-continued

```
Glu Trp Met Ala Val Ile Trp Tyr Asp Gly Ser Asn Lys Phe Tyr Ala
 65                  70                  75                  80

Asp Ser Val Lys Gly Arg Phe Thr Ile Ser Arg Asp Asn Ser Lys Asn
                 85                  90                  95

Thr Val Tyr Leu Gln Met Asn Ser Leu Arg Ala Glu Asp Thr Ala Val
            100                 105                 110

Tyr Tyr Cys Ala Lys Asp Ser Arg Gly Tyr Cys Ser Ser Ile Ile Cys
        115                 120                 125

Phe Glu Gly Gly Leu Asp Asn Trp Gly Gln Gly Thr Leu Val Thr Val
130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Gly Leu His Asn His
450                 455                 460

Tyr Thr Gln Lys Ser Leu Ser Leu Phe Pro Gly Lys
465                 470                 475
```

<210> SEQ ID NO 49
<211> LENGTH: 215
<212> TYPE: PRT
<213> ORGANISM: Artificial Sequence
<220> FEATURE:
<223> OTHER INFORMATION: CT147 light chain

<400> SEQUENCE: 49

```
Glu Ile Val Leu Thr Gln Ser Pro Gly Thr Leu Ser Val Ser Pro Gly
1               5                   10                  15

Glu Arg Ala Thr Leu Ser Cys Arg Ala Ser Arg Arg Val Gly Ser Thr
            20                  25                  30

Tyr Leu Ala Trp Tyr Gln Gln Lys Pro Gly Gln Ala Pro Arg Arg Leu
        35                  40                  45

Ile Tyr Gly Ala Ser Ser Arg Ala Ala Gly Ile Pro Asp Arg Phe Ser
    50                  55                  60

Gly Thr Gly Ser Gly Thr Asp Phe Thr Leu Thr Ile Ser Arg Val Asp
65                  70                  75                  80

Pro Glu Asp Phe Ala Val Tyr Tyr Cys Gln Gln Tyr Ala Ala Ser Pro
                85                  90                  95

Trp Thr Phe Gly Gln Gly Thr Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 50
<211> LENGTH: 456
<212> TYPE: PRT
<213> ORGANISM: Artificial Sequence
<220> FEATURE:
<223> OTHER INFORMATION: CT147 heavy chain
<220> FEATURE:
<221> NAME/KEY: misc_feature
<222> LOCATION: (219)..(219)
<223> OTHER INFORMATION: Xaa can be any naturally occurring amino acid

<400> SEQUENCE: 50

```
Gln Val Gln Leu Val Gln Ser Gly Gly Glu Leu Lys Lys Pro Gly Ala
1               5                   10                  15

Ser Val Arg Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Val
        35                  40                  45

Gly Trp Ile Ser Ala Tyr Thr Gly Asn Thr Asp Tyr Ala Gln Lys Val
    50                  55                  60

Gln Gly Arg Val Thr Met Thr Thr Asp Thr Ser Thr Ser Thr Ala Tyr
```

65                  70                  75                  80
Met Glu Leu Arg Ser Leu Thr Ser Asp Asp Thr Ala Val Tyr Tyr Cys
                        85                  90                  95

Ala Arg Asp Lys Val Gln Gly Arg Val Glu Ala Gly Ser Gly Gly Arg
                100                 105                 110

His Asp Tyr Trp Gly Gln Gly Thr Leu Val Thr Val Ser Ser Ala Ser
                115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                    165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Xaa Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                    245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                    325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                    405                 410                 415

Ser Lys Leu Thr Val Asp Lys Ser Arg Trp Gln Gln Gly Asn Val Phe
                420                 425                 430

Ser Cys Ser Val Met His Glu Gly Leu His Asn His Tyr Thr Gln Lys
            435                 440                 445

Ser Leu Ser Leu Ser Pro Gly Lys
    450                 455

<210> SEQ ID NO 51
<211> LENGTH: 215
<212> TYPE: PRT
<213> ORGANISM: Artificial Sequence

```
<220> FEATURE:
<223> OTHER INFORMATION: CT149 light chain

<400> SEQUENCE: 51

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Arg Val Gly Ser Thr
            20                  25                  30

Tyr Ile Ala Trp Tyr Gln Gln Lys Ser Gly Gln Ala Pro Arg Arg Leu
        35                  40                  45

Ile Tyr Gly Ala Ser Asn Arg Ala Thr Asp Ile Pro Asp Arg Phe Ser
50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 52
<211> LENGTH: 456
<212> TYPE: PRT
<213> ORGANISM: Artificial Sequence
<220> FEATURE:
<223> OTHER INFORMATION: CT149 heavy chain

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Pro Glu Trp Val
        35                  40                  45

Gly Trp Ile Ser Ala Tyr Thr Gly Ile Thr Asp Tyr Ala Gln Lys Phe
50                  55                  60

Gln Gly Arg Val Thr Leu Thr Thr Asp Ala Thr Thr Ala Thr Ala Phe
65                  70                  75                  80

Leu Asp Leu Arg Ser Leu Arg Pro Asp Asp Thr Ala Thr Tyr Phe Cys
                85                  90                  95

Ala Arg Asp Lys Val Gln Gly Arg Val Glu Val Gly Ser Gly Gly Arg
            100                 105                 110

His Asp Tyr Trp Gly Gln Gly Thr Leu Val Ile Val Ser Ser Ala Ser
```

```
            115                 120                 125
Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Gly Leu His Asn His Tyr Thr Gln Lys
        435                 440                 445

Ser Leu Ser Leu Ser Pro Gly Lys
    450                 455

<210> SEQ ID NO 53
<211> LENGTH: 215
<212> TYPE: PRT
<213> ORGANISM: Artificial Sequence
<220> FEATURE:
<223> OTHER INFORMATION: CT164 light chain

<400> SEQUENCE: 53

Glu Val Val Leu Thr Gln Ser Pro Gly Thr Leu Thr Leu Pro Pro Gly
1               5                   10                  15

Asp Arg Ala Thr Leu Ser Cys Arg Ala Ser His Ser Val Gly Ser Thr
```

```
            20                  25                  30
Tyr Ile Ala Trp Phe Gln Gln Lys Ser Gly Gln Ala Pro Arg Arg Leu
        35                  40                  45

Ile Tyr Gly Ala Ser Asn Arg Ala Thr Asp Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 54
<211> LENGTH: 456
<212> TYPE: PRT
<213> ORGANISM: Artificial Sequence
<220> FEATURE:
<223> OTHER INFORMATION: CT164 heavy chain

<400> SEQUENCE: 54

Gln Val Gln Leu Val Gln Ser Gly Val Glu Val Lys Lys Pro Gly Ala
1               5                   10                  15

Ser Val Lys Val Ser Cys Lys Thr Ser Gly Tyr Pro Phe Ser Thr Tyr
            20                  25                  30

Gly Val Ser Trp Val Arg Gln Ala Pro Gly Gln Gly Leu Glu Trp Val
        35                  40                  45

Gly Trp Ile Ser Gly Tyr Thr Gly Ile Thr Asp Tyr Ala Gln Lys Ser
    50                  55                  60

Gln Gly Arg Val Thr Leu Thr Thr Asp Ala Ser Thr Ala Thr Ala Phe
65                  70                  75                  80

Leu Glu Leu Arg Ser Leu Arg Pro Asp Asp Thr Ala Thr Tyr Phe Cys
                85                  90                  95

Ala Arg Asp Lys Val Gln Gly Arg Val Glu Ala Gly Ser Gly Gly Arg
            100                 105                 110

His Asp Tyr Trp Gly Gln Gly Thr Leu Val Ile Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
```

165                 170                 175
His Thr Phe Pro Ala Val Leu Gln Ser Ser Gly Leu Tyr Ser Leu Ser
                180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Gly Leu His Asn His Tyr Thr Gln Lys
        435                 440                 445

Ser Leu Ser Leu Ser Pro Gly Lys
    450                 455

<210> SEQ ID NO 55
<211> LENGTH: 215
<212> TYPE: PRT
<213> ORGANISM: Artificial Sequence
<220> FEATURE:
<223> OTHER INFORMATION: CT166 light chain

<400> SEQUENCE: 55

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Ser Ile Gly Ser Thr
            20                  25                  30

Tyr Ile Ala Trp Tyr Gln Gln Lys Ser Gly Gln Ala Pro Arg Arg Leu
        35                  40                  45

Ile Tyr Gly Ala Ser Asn Arg Ala Ser Asp Ile Pro Asp Arg Phe Ser
    50                  55                  60

Gly Ser Gly Ser Gly Thr Asp Phe Thr Leu Thr Ile Arg Arg Leu Glu

```
            65                  70                  75                  80
Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys Arg Thr Val Ala
            100                 105                 110

Ala Pro Ser Val Phe Ile Phe Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 56
<211> LENGTH: 456
<212> TYPE: PRT
<213> ORGANISM: Artificial Sequence
<220> FEATURE:
<223> OTHER INFORMATION: CT166 heavy chain

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Leu Glu Trp Val
        35                  40                  45

Gly Trp Ile Ser Gly Tyr Thr Gly Ile Thr Asp Tyr Ala Gln Lys Phe
    50                  55                  60

Gln Gly Arg Val Thr Leu Thr Thr Asp Ala Thr Thr Ala Thr Ala Phe
65                  70                  75                  80

Leu Glu Leu Arg Ser Leu Arg Pro Asp Asp Thr Ala Thr Tyr Phe Cys
                85                  90                  95

Ala Arg Asp Lys Val Gln Gly Val Glu Val Gly Ser Gly Gly Arg
            100                 105                 110

His Asp Tyr Trp Gly Gln Gly Thr Leu Val Ile Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
```

```
                210                 215                 220
Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Gly Leu His Asn His Tyr Thr Gln Lys
        435                 440                 445

Ser Leu Ser Leu Ser Pro Gly Lys
    450                 455

<210> SEQ ID NO 57
<211> LENGTH: 36
<212> TYPE: DNA
<213> ORGANISM: Artificial Sequence
<220> FEATURE:
<223> OTHER INFORMATION: CT104 light chain CDR1

<400> SEQUENCE: 57
agggccagtc agagtcttag cagcagctcc ttagtc                            36

<210> SEQ ID NO 58
<211> LENGTH: 20
<212> TYPE: DNA
<213> ORGANISM: Artificial Sequence
<220> FEATURE:
<223> OTHER INFORMATION: CT104 light chain CDR2

<400> SEQUENCE: 58
ggtgcatcca gcagggccac                                              20

<210> SEQ ID NO 59
<211> LENGTH: 27
<212> TYPE: DNA
<213> ORGANISM: Artificial Sequence
<220> FEATURE:
<223> OTHER INFORMATION: CT104 light chain CDR3
```

```
<400> SEQUENCE: 59
cagcagtatg ggaactcacc gtacacg                                        27

<210> SEQ ID NO 60
<211> LENGTH: 18
<212> TYPE: DNA
<213> ORGANISM: Artificial Sequence
<220> FEATURE:
<223> OTHER INFORMATION: CT104 heavy chain CDR1

<400> SEQUENCE: 60
aacaactatg ctatcagc                                                  18

<210> SEQ ID NO 61
<211> LENGTH: 54
<212> TYPE: DNA
<213> ORGANISM: Artificial Sequence
<220> FEATURE:
<223> OTHER INFORMATION: CT104 heavy chain CDR2

<400> SEQUENCE: 61
ggagggatca gccctatctt tgggacatta aactacgcag agaggttcca gggc           54

<210> SEQ ID NO 62
<211> LENGTH: 33
<212> TYPE: DNA
<213> ORGANISM: Artificial Sequence
<220> FEATURE:
<223> OTHER INFORMATION: CT104 heavy chain CDR3

<400> SEQUENCE: 62
ggttgtggct acaattgtta ctactttgac ggg                                 33

<210> SEQ ID NO 63
<211> LENGTH: 33
<212> TYPE: DNA
<213> ORGANISM: Artificial Sequence
<220> FEATURE:
<223> OTHER INFORMATION: CT120 light chain CDR1

<400> SEQUENCE: 63
agggccagtg agaatatttg gaacaacttg gcc                                 33

<210> SEQ ID NO 64
<211> LENGTH: 21
<212> TYPE: DNA
<213> ORGANISM: Artificial Sequence
<220> FEATURE:
<223> OTHER INFORMATION: CT120 light chain CDR2

<400> SEQUENCE: 64
ggtgcgtcca ccggggccac t                                              21

<210> SEQ ID NO 65
<211> LENGTH: 27
<212> TYPE: DNA
<213> ORGANISM: Artificial Sequence
<220> FEATURE:
<223> OTHER INFORMATION: CT120 light chain CDR3

<400> SEQUENCE: 65
cagcagtata attcgtggcc tcggacg                                        27

<210> SEQ ID NO 66
<211> LENGTH: 15
```

```
<212> TYPE: DNA
<213> ORGANISM: Artificial Sequence
<220> FEATURE:
<223> OTHER INFORMATION: CT120 heavy chain CDR1

<400> SEQUENCE: 66
agtcatgcta tcagt                                                    15

<210> SEQ ID NO 67
<211> LENGTH: 51
<212> TYPE: DNA
<213> ORGANISM: Artificial Sequence
<220> FEATURE:
<223> OTHER INFORMATION: CT120 heavy chain CDR2

<400> SEQUENCE: 67
gggatcagcc ctatgtttgg aacaacacac tacgcacaga agttccaggg c            51

<210> SEQ ID NO 68
<211> LENGTH: 42
<212> TYPE: DNA
<213> ORGANISM: Artificial Sequence
<220> FEATURE:
<223> OTHER INFORMATION: CT120 heavy chain CDR3

<400> SEQUENCE: 68
gatggtgcgg ggagttatta tccactcaac tggttcgacc cc                      42

<210> SEQ ID NO 69
<211> LENGTH: 36
<212> TYPE: DNA
<213> ORGANISM: Artificial Sequence
<220> FEATURE:
<223> OTHER INFORMATION: CT123 light chain CDR1

<400> SEQUENCE: 69
agggccagtc agagtgttag catcagctac ttagcc                             36

<210> SEQ ID NO 70
<211> LENGTH: 21
<212> TYPE: DNA
<213> ORGANISM: Artificial Sequence
<220> FEATURE:
<223> OTHER INFORMATION: CT123 light chain CDR2

<400> SEQUENCE: 70
ggcgcatcca ggagggccac t                                             21

<210> SEQ ID NO 71
<211> LENGTH: 27
<212> TYPE: DNA
<213> ORGANISM: Artificial Sequence
<220> FEATURE:
<223> OTHER INFORMATION: CT123 light chain CDR3

<400> SEQUENCE: 71
cagcagtatg gtagctcacc gtacact                                       27

<210> SEQ ID NO 72
<211> LENGTH: 15
<212> TYPE: DNA
<213> ORGANISM: Artificial Sequence
<220> FEATURE:
<223> OTHER INFORMATION: CT123 heavy chain CDR1

<400> SEQUENCE: 72
```
aggtttggca tccac                                              15

<210> SEQ ID NO 73
<211> LENGTH: 51
<212> TYPE: DNA
<213> ORGANISM: Artificial Sequence
<220> FEATURE:
<223> OTHER INFORMATION: CT123 heavy chain CDR2

<400> SEQUENCE: 73
gttatatggt acgatggaag taataaattc tatgcagact ccgtgaaggg c        51

<210> SEQ ID NO 74
<211> LENGTH: 54
<212> TYPE: DNA
<213> ORGANISM: Artificial Sequence
<220> FEATURE:
<223> OTHER INFORMATION: CT123 heavy chain CDR3

<400> SEQUENCE: 74
gattcccgcg gatattgtag tagtatcatt tgttttgagg ggggacttga caac      54

<210> SEQ ID NO 75
<211> LENGTH: 36
<212> TYPE: DNA
<213> ORGANISM: Artificial Sequence
<220> FEATURE:
<223> OTHER INFORMATION: CT147 light chain CDR1

<400> SEQUENCE: 75
agggccagtc ggcgcgttgg cagcacctac ttagcc                          36

<210> SEQ ID NO 76
<211> LENGTH: 21
<212> TYPE: DNA
<213> ORGANISM: Artificial Sequence
<220> FEATURE:
<223> OTHER INFORMATION: CT147 light chain CDR2

<400> SEQUENCE: 76
ggtgcatcca gcagggccgc t                                          21

<210> SEQ ID NO 77
<211> LENGTH: 27
<212> TYPE: DNA
<213> ORGANISM: Artificial Sequence
<220> FEATURE:
<223> OTHER INFORMATION: CT147 light chain CDR3

<400> SEQUENCE: 77
cagcagtatg ctgcctcacc gtggacg                                    27

<210> SEQ ID NO 78
<211> LENGTH: 15
<212> TYPE: DNA
<213> ORGANISM: Artificial Sequence
<220> FEATURE:
<223> OTHER INFORMATION: CT147 heavy chain CDR1

<400> SEQUENCE: 78
acctatggca tcagc                                                 15

<210> SEQ ID NO 79
<211> LENGTH: 51
<212> TYPE: DNA
<213> ORGANISM: Artificial Sequence
<220> FEATURE:
<223> OTHER INFORMATION: CT147 heavy chain CDR2

<400> SEQUENCE: 79
tggatcagcg cttatactgg aaatacagac tatgcacaga aggtccaggg c         51

<210> SEQ ID NO 80
<211> LENGTH: 51
<212> TYPE: DNA
<213> ORGANISM: Artificial Sequence
<220> FEATURE:
<223> OTHER INFORMATION: CT147 heavy chain CDR3

<400> SEQUENCE: 80
gataaggtcc aggggcgcgt tgaagcggga agtgggggcc ggcatgacta c         51

<210> SEQ ID NO 81
<211> LENGTH: 36
<212> TYPE: DNA
<213> ORGANISM: Artificial Sequence
<220> FEATURE:
<223> OTHER INFORMATION: CT149 light chain CDR1

<400> SEQUENCE: 81
agggccagtc accgtgttgg cagcacctac atagcc                          36

<210> SEQ ID NO 82
<211> LENGTH: 21
<212> TYPE: DNA
<213> ORGANISM: Artificial Sequence
<220> FEATURE:
<223> OTHER INFORMATION: CT149 light chain CDR2

<400> SEQUENCE: 82
ggtgcatcca acagggccac t                                          21

<210> SEQ ID NO 83
<211> LENGTH: 27
<212> TYPE: DNA
<213> ORGANISM: Artificial Sequence
<220> FEATURE:
<223> OTHER INFORMATION: CT149 light chain CDR3

<400> SEQUENCE: 83
cagcagttta gtgtttcacc gtggacg                                    27

<210> SEQ ID NO 84
<211> LENGTH: 15
<212> TYPE: DNA
<213> ORGANISM: Artificial Sequence
<220> FEATURE:
<223> OTHER INFORMATION: CT149 heavy chain CDR1

<400> SEQUENCE: 84
acttatggag tcagt                                                 15

<210> SEQ ID NO 85
<211> LENGTH: 51
<212> TYPE: DNA
<213> ORGANISM: Artificial Sequence
<220> FEATURE:
<223> OTHER INFORMATION: CT149 heavy chain CDR2

<400> SEQUENCE: 85
tggatcagcg cttacactgg tatcacagac tacgcacaga agtttcaggg c         51

<210> SEQ ID NO 86
<211> LENGTH: 51
<212> TYPE: DNA
<213> ORGANISM: Artificial Sequence
<220> FEATURE:
<223> OTHER INFORMATION: CT149 heavy chain CDR3

<400> SEQUENCE: 86
gataaggtgc aggggcgcgt tgaagtggga tctgggggtc gtcatgacta c    51

<210> SEQ ID NO 87
<211> LENGTH: 36
<212> TYPE: DNA
<213> ORGANISM: Artificial Sequence
<220> FEATURE:
<223> OTHER INFORMATION: CT164 light chain CDR1

<400> SEQUENCE: 87
agggccagtc acagtgttgg cagcacctac atagcc    36

<210> SEQ ID NO 88
<211> LENGTH: 21
<212> TYPE: DNA
<213> ORGANISM: Artificial Sequence
<220> FEATURE:
<223> OTHER INFORMATION: CT164 light chain CDR2

<400> SEQUENCE: 88
ggtgcatcca acagggccac t    21

<210> SEQ ID NO 89
<211> LENGTH: 27
<212> TYPE: DNA
<213> ORGANISM: Artificial Sequence
<220> FEATURE:
<223> OTHER INFORMATION: CT164 light chain CDR3

<400> SEQUENCE: 89
cagcagttta gtgtttcacc gtggacg    27

<210> SEQ ID NO 90
<211> LENGTH: 15
<212> TYPE: DNA
<213> ORGANISM: Artificial Sequence
<220> FEATURE:
<223> OTHER INFORMATION: CT164 heavy chain CDR1

<400> SEQUENCE: 90
acttatggag tcagc    15

<210> SEQ ID NO 91
<211> LENGTH: 51
<212> TYPE: DNA
<213> ORGANISM: Artificial Sequence
<220> FEATURE:
<223> OTHER INFORMATION: CT164 heavy chain CDR2

<400> SEQUENCE: 91
tggatcagcg gttatactgg tatcacagac tacgcacaga gtctcagggc    51

<210> SEQ ID NO 92
<211> LENGTH: 51
<212> TYPE: DNA
<213> ORGANISM: Artificial Sequence
<220> FEATURE:
<223> OTHER INFORMATION: CT164 heavy chain CDR3

<400> SEQUENCE: 92
gacaaagtgc aggggcgcgt tgaagcggga tctgggggtc gtcacgacta c     51

<210> SEQ ID NO 93
<211> LENGTH: 36
<212> TYPE: DNA
<213> ORGANISM: Artificial Sequence
<220> FEATURE:
<223> OTHER INFORMATION: CT166 light chain CDR1

<400> SEQUENCE: 93
agggccagtc acagtattgg cagcacctac atagcc                      36

<210> SEQ ID NO 94
<211> LENGTH: 21
<212> TYPE: DNA
<213> ORGANISM: Artificial Sequence
<220> FEATURE:
<223> OTHER INFORMATION: CT166 light chain CDR2

<400> SEQUENCE: 94
ggtgcatcca acagggcctc t                                      21

<210> SEQ ID NO 95
<211> LENGTH: 27
<212> TYPE: DNA
<213> ORGANISM: Artificial Sequence
<220> FEATURE:
<223> OTHER INFORMATION: CT166 light chain CDR3

<400> SEQUENCE: 95
cagcagttta gtgtttcacc gtggacg                                27

<210> SEQ ID NO 96
<211> LENGTH: 15
<212> TYPE: DNA
<213> ORGANISM: Artificial Sequence
<220> FEATURE:
<223> OTHER INFORMATION: CT166 heavy chain CDR1

<400> SEQUENCE: 96
acttatggag tcagc                                             15

<210> SEQ ID NO 97
<211> LENGTH: 51
<212> TYPE: DNA
<213> ORGANISM: Artificial Sequence
<220> FEATURE:
<223> OTHER INFORMATION: CT166 heavy chain CDR2

<400> SEQUENCE: 97
tggatcagcg gttacactgg tatcacagac tacgcacaga gtttcaggg c      51

<210> SEQ ID NO 98
<211> LENGTH: 51
<212> TYPE: DNA
<213> ORGANISM: Artificial Sequence
<220> FEATURE:
<223> OTHER INFORMATION: CT166 heavy chain CDR3

<400> SEQUENCE: 98
gataaggtgc aggggcgcgt tgaagtggga tctgggggtc gtcatgacta c     51

<210> SEQ ID NO 99

<211> LENGTH: 708
<212> TYPE: DNA
<213> ORGANISM: Artificial Sequence
<220> FEATURE:
<223> OTHER INFORMATION: CT104 light chain

<400> SEQUENCE: 99

| | |
|---|---|
| atggaaaccc cagcgcagct tctcttcctc ctgctactct ggctcccaga taccaccgga | 60 |
| gaaattgtgt tgacgcagtc tccaggcacc ctgtctttgt ctccagggga aagagccacc | 120 |
| ctctcctgca gggccagtca gagtcttagc agcagctcct tagtctggta ccagcagaaa | 180 |
| cctggccagg ctcccaggct cctcatctat ggtgcatcca gcagggccac tggcatccca | 240 |
| gacaggttca gtggcagtgg gtctgggaca gacttcactc tcaccatcag cagactggag | 300 |
| cctgaagatt ttgcagtgta ttactgtcag cagtatggga actcaccgta cacgtttggc | 360 |
| caggggaccc aggttgagat caaacgaact gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca aagcagacta cgagaaacac aaagtctacg cctgcgaagt cacccatcag | 660 |
| ggcctgagct cgcccgtcac aaagagcttc aacaggggag agtgttag | 708 |

<210> SEQ ID NO 100
<211> LENGTH: 1410
<212> TYPE: DNA
<213> ORGANISM: Artificial Sequence
<220> FEATURE:
<223> OTHER INFORMATION: CT104 heavy chain

<400> SEQUENCE: 100

| | |
|---|---|
| atggactgga cctggaggtt cctctttgtg gtggcagcag ctacaggtgt ccagtcccag | 60 |
| gtgcagctgg tgcagtctgg ggctgaggtg aagaagcctg gtcctcggt gaaggtctcc | 120 |
| tgcaaggctt ctggaggcac cctcaacaac tatgctatca gctgggtgcg acaggcccct | 180 |
| ggacaagggc ttgagtggat gggagggatc agccctatct ttgggacatt aaactacgca | 240 |
| gagaggttcc agggcagagt caccattacc gcggacgtat ttacgaacac agtctacatg | 300 |
| gagctgagca gcctgagatc tgaggacacg gccgtgtatt tctgtgcgag aggttgtggc | 360 |
| tacaattgtt actactttga cgggtggggc cagggaaccc tggtcaccgt ttcctcagcc | 420 |
| tccaccaagg gcccatcggt cttccccctg gcaccctcct ccaagagcac ctctgggggc | 480 |
| acagcggccc tgggctgcct ggtcaaggac tacttccccg aaccggtgac ggtgtcgtgg | 540 |
| aactcaggcg ccctgaccag cggcgtgcac accttcccgg ctgtcctaca gtcctcagga | 600 |
| ctctactccc tcagcagcgt ggtgaccgtg ccctccagca gcttgggcac ccagacctac | 660 |
| atctgcaacg tgaatcacaa gcccagcaac accaaggtgg acaagaaagt tgagcccaaa | 720 |
| tcttgtgaca aaactcacac atgcccaccg tgcccagcac ctgaactcct ggggggaccg | 780 |
| tcagtcttcc tcttcccccc aaaacccaag gacaccctca tgatctcccg gacccctgag | 840 |
| gtcacatgcg tggtggtgga cgtgagccac gaagaccctg aggtcaagtt caactggtac | 900 |
| gtggacggcg tggaggtgca taatgccaag acaaagccgc gggaggagca gtacaacagc | 960 |
| acgtaccgtg tggtcagcgt cctcaccgtc ctgcaccagg actggctgaa tggcaaggag | 1020 |
| tacaagtgca aggtctccaa caaagccctc ccagccccca tcgagaaaac catctccaaa | 1080 |
| gccaaagggc agccccgaga accacaggtg tacaccctgc cccatcccg ggatgagctg | 1140 |

```
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttttt cctttacagc aagctcaccg tggacaagag caggtggcag    1320
caggggaacg ttttttcatg ctccgtgatg catgagggtt tgcacaaccc ctacacgcag    1380
aagagcctct ccctgtttcc gggtaaatga                                     1410

<210> SEQ ID NO 101
<211> LENGTH: 705
<212> TYPE: DNA
<213> ORGANISM: Artificial Sequence
<220> FEATURE:
<223> OTHER INFORMATION: CT120 light chain

<400> SEQUENCE: 101
atggaagccc cagctcagct tctcttcctc ctgctactct ggctcccaga taccaccgga     60
gaaattgtgt tgacacagtc tccagccacc ttgtctttgt ctccagggga aagagccacc    120
ctctcctgca gggccagtga gaatatttgg aacaacttgg cctggtacca gcaaaaacct    180
ggccaggctc ccaggctcct catctctggt gcgtccaccg gggccactgg tgtcccaagt    240
aggtttagag gcagcgggtc taggacagaa ttcactctca ccatcagcag cctgcagtct    300
gaagattttg caatttattt ctgtcagcag tataattcgt ggcctcggac gttcggccca    360
gggaccaagg tggagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag cacccctgacg    600 ctgagcaaag cagactacga aaacacaaa gtctacgcct gcgaagtcac ccatcagggc    660
ctgagctcgc ccgtcacaaa gagcttcaac aggggagagt gttag                   705

<210> SEQ ID NO 102
<211> LENGTH: 1419
<212> TYPE: DNA
<213> ORGANISM: Artificial Sequence
<220> FEATURE:
<223> OTHER INFORMATION: CT120 heavy chain

<400> SEQUENCE: 102
atggactgga cctggaggtt cctctttgtg gtggcagcag ctacaggtgt ccagtgccag     60
gtgcagctgt gcagtctgg ggctgaggtg aagatgcctg gtcctcggt gaaggtctcc     120 tgcaagactt ctggagtctt cttcagcagt catgctatca gttgggtgcg acaggcccct    180
ggacaagggc ttgagtggat gggagggatc agccctatgt ttggaacaac acactacgca    240
cagaagttcc agggcagagt cacgattacc gcggaccaat ccacgaccac agcctacatg    300
gagttgacca gtcttacatc tgaggacacg gccgtatatt actgtgcgcg tgatggtgcg    360 ggagttatt atccactcaa ctggttcgac ccctggggcc agggaaccct ggtcaccgtc    420
tcctcagcct ccaccaaggg cccatcggtc ttccccctgg cacccctcctc caagagcacc    480 tctggggca gcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagagagtt    720
```

| | |
|---|---|
| gagcccaaat cttgtgacaa aactcacaca tgcccaccgt gcccagcacc tgaactcctg | 780 |
| gggggaccgt cagtcttcct cttcccccca aaacccaagg acaccctcat gatctcccgg | 840 |
| acccgtgagg tcacatgcgt ggtggtggac gtgagccacg aagaccctga ggtcaagttc | 900 |
| aactggtacg tggacggcgt ggaggtgcat aatgccaaga caaagccgcg ggaggagcag | 960 |
| tacaacagca cgtaccgtgt ggtcagcgtc ctcaccgtcc tgcaccagga ctggctgaat | 1020 |
| ggcaaggagt acaagtgcaa ggtctccaac aaagccctcc cagcccccat cgagaaaacc | 1080 |
| atctccaaag ccaaagggca gccccgagaa ccacaggtgt acaccctgcc cccatcccgg | 1140 |
| gatgagctga ccaagaacca ggtcagcctg acctgcctgg tcaaaggctt ttatcccagc | 1200 |
| gacatcgccg tggagtggga gagcaatggg cagccggaga caactacaa gaccacgcct | 1260 |
| cccgtgctgg actccgacgg ctccttttc ctttacagca agctcaccgt ggacaagagc | 1320 |
| aggtggcagc aggggaacgt cttttcatgc tccgtgatgc atgagggttt gcacaaccac | 1380 |
| tacacgcaga agagcctctc cctgtttccg ggtaaatga | 1419 |

<210> SEQ ID NO 103
<211> LENGTH: 708
<212> TYPE: DNA
<213> ORGANISM: Artificial Sequence
<220> FEATURE:
<223> OTHER INFORMATION: CT123 light chain

<400> SEQUENCE: 103

| | |
|---|---|
| atggaaaccc cagcgcagct tctcttcctc ctgctactct ggctcccaga taccaccgga | 60 |
| gaaactgtgt tgacgcagtc tccaggcacc ctgtctttgt ctccagggga aagagccacc | 120 |
| ctctcctgca gggccagtca gagtgttagc atcagctact tagcctggta ccagcggaaa | 180 |
| cctggccagg ctcccaggct cctcatctat ggcgcatcca gagggccac tggcatccca | 240 |
| gacaggttca gtggcagtgg gtctgggaca gacttcactc tcaccatcag cagactggag | 300 |
| cctgaagatt ttgcagtata ttactgtcag cagtatggta gctcaccgta cacttttggc | 360 |
| caggggacca agctggagat caaacgaact gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca aagcagacta cgagaaacac aaagtctacg cctgcgaagt cacccatcag | 660 |
| ggcctgagct cgcccgtcac aaaagagctt aacaggggag agtgttag | 708 |

<210> SEQ ID NO 104
<211> LENGTH: 1431
<212> TYPE: DNA
<213> ORGANISM: Artificial Sequence
<220> FEATURE:
<223> OTHER INFORMATION: CT123 heavy chain

<400> SEQUENCE: 104

| | |
|---|---|
| atggagtttg ggctgagctg ggttttcctc gttgctcttt taagaggtgt ccagtgtcag | 60 |
| gtgcagctgg tggagtctgg gggaggcgtg gtccagcctg gaggtccct gagactctcc | 120 |
| tgtgcagcgt ctggattcac cttcagtagg tttggcatcc actgggtccg ccaggctcca | 180 |
| ggcaagggc tggagtggat ggcagttata tggtacgatg gaagtaataa attctatgca | 240 |
| gactccgtga agggccgatt caccatctcc agagacaatt ccaagaacac ggtttatctg | 300 |
| caaatgaaca gcctcagagc cgaggacacg gctgtctatt actgtgcgaa agattcccgc | 360 |

```
ggatattgta gtagtatcat ttgttttgag gggggacttg acaactgggg ccagggaacc      420
ctggtcaccg tctcctcagc ctccaccaag ggcccatcgg tcttccccct ggcaccctcc      480
tccaagagca cctctggggg cacagcggcc ctgggctgcc tggtcaagga ctacttcccc      540
gaaccggtga cggtgtcgtg aactcaggc gccctgacca cggcgtgca caccttcccg        600 gctgtcctac agtcctcagg actctactcc ctcagcagcg tggtgaccgt gccctccagc      660
agcttgggca cccagaccta catctgcaac gtgaatcaca agcccagcaa caccaaggtg      720
gacaagagag ttgagcccaa atcttgtgac aaaactcaca catgcccacc gtgcccagca      780
cctgaactcc tggggggacc gtcagtcttc ctcttccccc caaaacccaa ggacaccctc      840
atgatctccc ggacccctga ggtcacatgc gtggtggtgg acgtgagcca cgaagaccct      900
gaggtcaagt tcaactggta cgtggacggc gtggaggtgc ataatgccaa gacaaagccg      960
cgggaggagc agtacaacag cacgtaccgt gtggtcagcg tcctcaccgt cctgcaccag     1020
gactggctga atggcaagga gtacaagtgc aaggtctcca acaaagccct cccagccccc     1080
atcgagaaaa ccatctccaa agccaaaggg cagccccgag aaccacaggt gtacaccctg     1140
cccccatccc gggatgagct gaccaagaac caggtcagcc tgacctgcct ggtcaaaggc     1200
ttctatccca gcgacatcgc cgtggagtgg gagagcaatg ggcagccgga gaacaactac     1260
aagaccacgc ctcccgtgct ggactccgac ggctcctttt tcctttacag caagctcacc     1320
gtggacaaga gcaggtggca gcaggggaac gtcttttcat gctccgtgat gcatgagggt     1380
ttgcacaacc actacacgca gaagagcctc tccctgtttc cgggtaaatg a              1431

<210> SEQ ID NO 105
<211> LENGTH: 648
<212> TYPE: DNA
<213> ORGANISM: Artificial Sequence
<220> FEATURE:
<223> OTHER INFORMATION: CT147 light chain

<400> SEQUENCE: 105
gagattgtgt tgactcagtc tccaggcacc ctgtctgtgt ctccagggga aagagccacc       60
ctctcctgca gggccagtcg cgcgttggc agcacctact tagcctggta ccagcagaaa       120
cctggccagg ctcccaggcg cctcatctat ggtgcatcca gcagggccgc tggcatccca      180
gacaggttca gtggcactgg gtctgggaca gacttcactc tcaccatcag cagggtggac      240
cctgaagatt ttgcggtata ttactgtcag cagtatgctg cctcaccgtg gacgttcggc      300
caagggacca cggtggagat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgttag                   648

<210> SEQ ID NO 106
<211> LENGTH: 1371
<212> TYPE: DNA
<213> ORGANISM: Artificial Sequence
<220> FEATURE:
<223> OTHER INFORMATION: CT147 heavy chain

<400> SEQUENCE: 106
```

```
caggttcagc tggtgcagtc tggaggtgag ctgaagaagc ctggggcctc agtgagggtc      60
tcctgtaagg cttctggcta ccctttacc acctatggca tcagctgggt gcgacaggcc     120
cctggacaag gccttgagtg ggtgggatgg atcagcgctt atactggaaa tacagactat    180
gcacagaagt tccagggcag agtaaccatg accacggaca catccacgag cacagcctac    240
atggagctga ggagcctcac atctgacgac acggccgtct attactgtgc gagagataag    300
gtccaggggc gcgttgaagc gggaagtggg ggccggcatg actactgggg ccagggaacc    360
ctggtcaccg tctcctcagc ctccaccaag ggcccatcgg tcttcccct ggcaccctcc     420
tccaagagca cctctggggg cacagcggcc ctgggctgcc tggtcaagga ctacttcccc    480
gaaccggtga cggtgtcgtg aactcaggc gccctgacca gcggcgtgca ccttcccg       540
gctgtcctac agtcctcagg actctactct ctcagcagcg tggtgaccgt gccctccagc    600
agcttgggca cccagaccta catctgcaac gtgaatcaca agcccagcaa caccaargtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggatgagct gaccaagaac caggtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctacag caagctcacc   1260
gtggacaaga gcaggtggca gcaggggaac gtcttctcat gctccgtgat gcatgagggt   1320
ctgcacaacc actacacgca gaagagcctc tccctgtctc cgggtaaatg a            1371
```

<210> SEQ ID NO 107
<211> LENGTH: 648
<212> TYPE: DNA
<213> ORGANISM: Artificial Sequence
<220> FEATURE:
<223> OTHER INFORMATION: CT149 light chain

<400> SEQUENCE: 107

```
gaagttgtgt tgacacagtc tcccggcacc ctggctttgc ctccagggga aagagccacc     60
ctctcctgca gggccagtca ccgtgttggc agcacctaca tagcctggta tcagcagaag    120
tctggccagg ctcccaggcg cctcatctat ggtgcatcca cagggccac tgacatccca     180
gacaggttca gtggcagtgg gtccgggaca gacttcactc tcaccatcag gagactggag    240
cctgaagatt ctgcagtgta ttactgtcag cagtttagtg tttcaccgtg gacgttcggc    300
caagggacca gggtggaaat caagcgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac cgagaaacac aaagtctacg cctgcgaagt cacccatcag    600
ggcctgagct cgcccgtcac aaagagcttc aacaggggag agtgttag                  648
```

<210> SEQ ID NO 108
<211> LENGTH: 1371
<212> TYPE: DNA
<213> ORGANISM: Artificial Sequence
<220> FEATURE:
<223> OTHER INFORMATION: CT149 heavy chain

<400> SEQUENCE: 108

| | |
|---|---|
| caggttcagc tggtgcagtc tggagctgag gtgaagaagc ctggggcctc agtgaaggtc | 60 |
| tcctgcaaga cttctggtta ttccttttcc acttatggag tcagttgggt ccgacaggcc | 120 |
| cccggacaag gcctgagtg ggtgggatgg atcagcgctt acactggtat cacagactac | 180 |
| gcacagaagt tcagggcag agtcactctg accacagacg caaccacggc caccgccttc | 240 |
| ctggacctga ggagtctgag acctgacgac acggccacgt atttctgtgc gagagataag | 300 |
| gtgcaggggc gcgttgaagt gggatctggg ggtcgtcatg actactgggg acagggaacc | 360 |
| ctggtcatcg tctcctcagc ctccaccaag ggcccatcgg tcttccccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca caccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagaaag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |
| atgatctccc ggacccctga ggtcacatgc gtggtggtgg acgtgagcca cgaagaccct | 840 |
| gaggtcaagt tcaactggta cgtggacggc gtggaggtgc ataatgccaa gacaaagccg | 900 |
| cgggaggagc agtacaacag cacgtaccgt gtggtcagcg tcctcaccgt cctgcaccag | 960 |
| gactggctga atggcaagga gtacaagtgc aaggtctcca acaaagccct cccagccccc | 1020 |
| atcgagaaaa ccatctccaa agccaaaggg cagccccgag aaccacaggt gtacaccctg | 1080 |
| cccccatccc gggatgagct gaccaagaac caggtcagcc tgacctgcct ggtcaaaggc | 1140 |
| ttctatccca gcgacatcgc cgtggagtgg gagagcaatg ggcagccgga gaacaactac | 1200 |
| aagaccacgc ctcccgtgct ggactccgac ggctccttct tcctctacag caagctcacc | 1260 |
| gtggacaaga gcaggtggca gcaggggaac gtcttctcat gctccgtgat gcatgagggt | 1320 |
| ctgcacaacc actacacgca gaagagcctc tccctgtctc cgggtaaatg a | 1371 |

<210> SEQ ID NO 109
<211> LENGTH: 648
<212> TYPE: DNA
<213> ORGANISM: Artificial Sequence
<220> FEATURE:
<223> OTHER INFORMATION: CT164 light chain

<400> SEQUENCE: 109

| | |
|---|---|
| gaagttgtgt tgacgcagtc tcccggcacc ctgactttgc ctccagggga cagagccacc | 60 |
| ctctcctgca gggccagtca cagtgttggc agcacctaca tagcctggtt tcagcagaag | 120 |
| tctggccagg ctcccaggcg cctcatctat ggtgcatcca cagggccac tgacatccca | 180 |
| gacaggttca gtggcagtgg gtccgggaca gacttcactc tcaccatcag agactggag | 240 |
| cctgaagatt ctgcagtgta ctactgtcag cagtttagtg tttcaccgtg acgttcggc | 300 |
| caagggacca gggtggaaat caagcgaact gtggctgcac catctgtctt catcttcccg | 360 |
| ccatctgatg agcagttgaa atctggaact gcctctgttg tgtgcctgct gaataacttc | 420 |

| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaagtctacg cctgcgaagt cacccatcag | 600 |
| ggcctgagct cgcccgtcac aaagagcttc aacaggggag agtgttag | 648 |

```
<210> SEQ ID NO 110
<211> LENGTH: 1371
<212> TYPE: DNA
<213> ORGANISM: Artificial Sequence
<220> FEATURE:
<223> OTHER INFORMATION: CT164 heavy chain

<400> SEQUENCE: 110
```

| caggttcagc tggtccagtc tggagtagag gtgaagaagc ctggggcctc agtgaaggtc | 60 |
| tcctgcaaga cttctggtta tccgttttcc acttatggag tcagctgggt ccgacaggcc | 120 |
| cctggacaag gccttgagtg ggtgggatgg atcagcggtt atactggtat cacagactac | 180 |
| gcacagaagt ctcagggcag agtcactctg acgacagacg caagcacggc caccgccttc | 240 |
| ttggagctga ggagtctgag gcctgacgac acggccacct attttgtgc gagagacaaa | 300 |
| gtgcagggc gcgttgaagc gggatctggg ggtcgtcacg actactgggg acagggaacc | 360 |
| ctggtcatcg tctcctcagc ctccaccaag ggcccatcgg tcttcccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca ccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagaaag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |
| atgatctccc ggacccctga ggtcacatgc gtggtggtgg acgtgagcca cgaagaccct | 840 |
| gaggtcaagt tcaactggta cgtggacggc gtggaggtgc ataatgccaa gacaaagccg | 900 |
| cgggaggagc agtacaacag cacgtaccgt gtggtcagcg tcctcaccgt cctgcaccag | 960 |
| gactggctga atggcaagga gtacaagtgc aaggtctcca acaaagccct cccagccccc | 1020 |
| atcgagaaaa ccatctccaa agccaaaggg cagccccgag aaccacaggt gtacaccctg | 1080 |
| cccccatccc gggatgagct gaccaagaac caggtcagcc tgacctgcct ggtcaaaggc | 1140 |
| ttctatccca gcgacatcgc cgtggagtgg gagagcaatg ggcagccgga gaacaactac | 1200 |
| aagaccacgc ctcccgtgct ggactccgac ggctccttct tcctctacag caagctcacc | 1260 |
| gtggacaaga gcaggtggca gcaggggaac gtcttctcat gctccgtgat gcatgagggt | 1320 |
| ctgcacaacc actacacgca gaagagcctc tccctgtctc cgggtaaatg a | 1371 |

```
<210> SEQ ID NO 111
<211> LENGTH: 648
<212> TYPE: DNA
<213> ORGANISM: Artificial Sequence
<220> FEATURE:
<223> OTHER INFORMATION: CT166 light chain

<400> SEQUENCE: 111
```

| gaagttgtgt tgacgcagtc tcccggcacc ctggctttgc ctccagggga aagagccacc | 60 |
| ctctcctgca gggccagtca cagtattggc agcacctaca tagcctggta tcagcagaag | 120 |
| tctggccagg ctcccaggcg cctcatctat ggtgcatcca cagggcctc tgacatccca | 180 |

```
gacaggttca gtggcagtgg gtccgggaca gacttcactc tcaccatcag gagactggag    240
cctgaagatt ctgcagtgta ttactgtcag cagtttagtg tttcaccgtg gacgttcggc    300
caagggacca gggtggaaat caagcgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttag                 648

<210> SEQ ID NO 112
<211> LENGTH: 1371
<212> TYPE: DNA
<213> ORGANISM: Artificial Sequence
<220> FEATURE:
<223> OTHER INFORMATION: CT166 heavy chain

<400> SEQUENCE: 112
caggttcagc tggtgcagtc tggagctgag gtgaagaagc ctggggcctc agtgaaggtc     60
tcctgcaaga cttctggtta ttccttttcc acttatggag tcagctgggt ccgacaggcc    120
cctggacaag gcttgagtg gatgggatgg atcagcggtt acactggtat cacagactac    180
gcacagaagt tcagggcag agtcactctg accacagacg caaccacggc caccgccttc    240
ctggagctga ggagtctgag acctgacgac acggccacct atttctgtgc gagagataag    300 gtgcagggc gcgttgaagt gggatctggg ggtcgtcatg actactgggg acagggaacc    360
ctggtcatcg tctcctcagc ctccaccaag ggcccatcgg tcttcccct ggcaccctcc    420 tccaagagca cctctggggg cacagcggcc ctgggctgcc tggtcaagga ctacttcccc    480
gaaccggtga cggtgtcgtg gaactcaggg gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggatgagct gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctacag caagctcacc    1260
gtggacaaga gcaggtggca gcaggggaac gtcttctcat gctccgtgat gcatgagggt    1320
ctgcacaacc actacacgca gaagagcctc tccctgtctc cgggtaaatg a             1371
```

COMPOSITION COMPRISING AT LEAST TWO INFLUENZA A VIRUS-NEUTRALIZING-BINDING MOLECULES

CROSS REFERENCE TO RELATED APPLICATIONS

This application is a national stage application under 35 U.S.C. 371 and claims the benefit of PCT Application No. PCT/KR2014/002691 having an international filing date of Mar. 28, 2014, which designated the United States, which PCT application claimed the benefit of Korean Patent Application No. 10-2013-0034041 filed Mar. 29, 2013, and Korean Patent Application No. 10-2013-0148247 filed Dec. 2, 2013, the disclosures of each of which are incorporated herein by reference.

TECHNICAL FIELD

The present invention relates to a composition comprising at least two influenza A virus-neutralizing binding molecules, and more particularly, to a composition comprising at least two human monoclonal antibodies having neutralizing activity against influenza A virus, which are produced by human B cells derived from the blood of patients who recovered from infection with influenza A virus.

BACKGROUND ART

Influenza, an illness caused by respiratory infection with influenza viruses, often occurs in winter. It is known to have very high infectivity and to affect all age groups, particularly elderly people (Treanor J, 2004, *N Engl J Med.* 350(3):218-20). Influenza viruses are enveloped RNA (ribonucleic acid) viruses belonging to the family Orthomyxoviridae and have a genome composed of eight negative-sense, single-stranded RNA (ribonucleic acid) segments. These influenza viruses are classified into types A, B and C. Influenza A viruses are further divided into subtypes based on their major surface proteins hemagglutinin (HA) and neuraminidase (NA). Up to date, 17 HAs and 10 NAs have been identified (Cheung T K and Poon L L 2007, *Ann N Y Acad. Sci.* 1102:1-25; Tong S, et al. 2012, Proc. Natl. Acad. Sci. U.S.A. 109:4269-4274). Influenza viruses can affect birds, pigs and humans depending on their types and have a genome composed of RNA segments, and for this reason, their genes can continuously mutate and recombine, resulting in new genetic variations (Treanor J, 2004. *N Engl J Med.* 350(3):218-20). Due to this continuous mutation, it is difficult to obtain permanent immunity against influenza viruses, and thus a preventive method that is currently thought to be most effective is a method of administering a vaccine against a particular type of influenza virus expected to be prevalent each year to develop immunity against the influenza virus each year.

Influenza virus vaccines that are currently administered each year are trivalent vaccines containing influenza A H1, H3 subtype HA and influenza type B HA.

Vaccines against influenza viruses are generally produced using eggs, but this production method is a time-consuming and inefficient method. Accordingly, this method has a problem in that it is difficult to produce sufficient amounts of vaccines each year within a limited time frame. In an attempt to solve this problem, studies on methods of producing vaccines by cell culture have been actively conducted by several pharmaceutical companies (GSK, Baxter, etc.). In addition, if pandemic influenza virus infection occurs, it is very difficult to develop a vaccine against the infection within a short time. Also, antiviral drugs are not completely reliable due to a problem associated with the emergence of drug-resistant mutant viruses.

To overcome this problem, antibodies against influenza viruses have recently been actively developed (Throsby et al, 2008, *PloS One* 3 (e3942); Sui et al., 2009, *Nature structural & molecular biology.* 16 (265-273); Simmons et al, 2007, *PloS Medicine* 4 (e178); Wrammert et al., 2011, *J Exp Med.* 208 (181-193); Corti et al., 2011, *Science* 333 (850-856)).

Blood products from recovered patients have been used to treat patients infected with various viruses, as well as to treat pandemic flu infections. For example, when patients infected with Spanish influenza virus had symptoms of pneumonia, blood products collected from patients who recovered from infection with the influenza virus are used to treat the influenza virus (Luke et al., 2006. *Annals of internal medicine.* 145:599). As such, hyperimmune globulin (IgIv) is purified from human plasma and used to treat patients infected with various viruses, but the product obtained as described above may not be safe from potential infectious agents in blood and is inefficient for mass production.

Antibodies against influenza A virus, which were recently filed for patent protection by the applicant, showed neutralizing activity against various influenza subtypes. Particularly, an antibody disclosed in Korean Patent Application No. 10-2011-0020061 showed neutralizing activity, mainly against phylogenetic group 1 (H1, H2, H5 and H9), and an antibody disclosed in Korean Patent Application 10-2012-0107512 showed neutralizing activity, mainly against phylogenetic group 2 (H3 and H7). Accordingly, the present inventors have conducted studies to develop a cocktail formulation containing at least two kinds of antibodies, which can exhibit preventive and therapeutic effects against all viruses belonging to groups 1 and 2, which are likely to be pandemic.

DISCLOSURE

Technical Problem

It is an object of the present invention to provide a composition comprising at least two influenza A virus-neutralizing binding molecules, the composition exhibiting neutralizing activity against both phylogenetic group 1 and phylogenetic group 2.

Another object of the present invention is to provide a method of diagnosing, preventing or treating a disease caused by influenza A virus by administering the composition.

Still another object of the present invention is to provide a method of diagnosing influenza A virus infection using the composition.

Yet another object of the present invention is to provide a kit for diagnosis of influenza A virus, which comprises the composition.

Technical Solution

To achieve the above objects, the present invention provides a composition comprising at least two influenza A virus-neutralizing binding molecules that bind to an epitope in the stem region of influenza A virus hemagglutinin (HA) protein, the composition comprising:

i) a first binding molecule capable of neutralizing at least one influenza A virus subtype selected from the group consisting of H1, H2, H5 and H9; and ii) a second binding molecule capable of neutralizing at least one influenza A virus subtype selected from the group consisting of H1, H3, H5, H7 and H9.

In an embodiment of the present invention, the epitope of the first binding molecule may comprise amino acid residues at positions 18, 38, 40, 291, 292 and 318 of an HA1 polypeptide. Further, the epitope of the first binding molecule may comprise amino acid residues at positions 18, 19, 20, 21, 41, 42, 45, 48, 49, 52 and 53 of an HA2 polypeptide.

In an embodiment of the present invention, the epitope of the first binding molecule may comprise amino acid residues at positions of 18, 38, 40, 291, 292 and 318 of the HA1 polypeptide, and may comprise amino acid residues at positions 18, 19, 20, 21, 41, 42, 45, 48, 49, 52 and 53 of the HA2 polypeptide.

In an embodiment of the present invention, the epitope of the second binding molecule may comprise amino acid residues at positions 278 and 318 of the HA1 polypeptide. Further, the epitope of the second binding molecule may comprise amino acid residues at positions 38, 39, 41, 42, 45, 48, 49, 52 and 53 of the HA2 polypeptide. Furthermore, the epitope of the second binding molecule may comprise amino acid residues at the positions of the HA1 polypeptide and/or HA2 polypeptide of a first monomer of HA, and may further comprise amino acid residues at positions 25, 32 and 33 of the HA1 polypeptide of a second monomer adjacent to the first monomer.

In an embodiment of the present invention, the epitope of the second binding molecule may comprise amino acid residues at positions 278 and 318 of the HA1 polypeptide, and may further comprise amino acid residues at positions 38, 39, 41, 42, 45, 48, 49, 52 and 53 of the HA2 polypeptide. In another embodiment, the epitope of the second binding molecule may comprise amino acid residues at the positions of the HA1 polypeptide and HA2 polypeptide of the first monomer of HA, and may further comprise amino acid residues at positions 25, 32 and 33 of the HA1 polypeptide of the second monomer adjacent to the first monomer.

In an embodiment of the present invention, the epitope of the second binding molecule may comprise amino acid residues at positions 278 and 318 of the HA1 polypeptide, and may comprise amino acid residues at positions 38, 39, 41, 42, 45, 48, 49, 52, 53, 58 and 99 of the HA2 polypeptide. In another embodiment, the epitope of the second binding molecule may comprise amino acid residues at the positions of the HA1 polypeptide and HA2 polypeptide of the first monomer of HA, and may further comprise amino acid residues at positions 25, 27, 32 and 33 of the HA1 polypeptide of the second monomer adjacent to the first monomer.

In an embodiment of the present invention, the epitope of the second binding molecule may comprise amino acid residues at positions 54, 55, 278, 291 and 318 of the HA1 polypeptide, and may comprise amino acid residues at positions 19, 20, 21, 38, 39, 41, 42, 45, 46, 48, 49, 52, 53, 56, 57 and 60 of the HA2 polypeptide. In another embodiment, the epitope of the second binding molecule may comprise amino acid residues at the positions of the HA1 polypeptide and HA2 polypeptide of the first monomer of HA, and may further comprise amino acid residues at positions 25, 32, 33, 310, 311, and 312 of HA1 polypeptide of the second monomer of HA adjacent to the first monomer of HA.

The numbering of the amino acid positions of the epitope is based on H3 HA numbering.

The binding molecules of the present invention can inhibit the fusion of virus to the target cell membrane. In addition, the binding molecules of the present invention can inhibit virus by the Fc functions of antibody, that is, ADCC and CDC.

The first binding molecule according to the present invention is capable of binding to influenza A virus or a fragment thereof with a binding affinity ($K_D$) of less than $1.0\times10^{-8}$ M, preferably less than $1.0\times10^{-9}$ M, more preferably less than $1.0\times10^{-10}$ M, even more preferably less than $1.0\times10^{-11}$ M, most preferably less than $1.0\times10^{-12}$ M.

The second binding molecule according to the present invention is capable of binding to influenza A virus or a fragment thereof with a binding affinity ($K_D$) of less than $1.0\times10^{-6}$ M, preferably less than $1.0\times10^{-7}$ M, more preferably less than $1.0\times10^{-8}$ M, even more preferably $1.0\times10^{-9}$ M, even more preferably less than $1.0\times10^{-10}$ M still more preferably less than $1.0\times10^{-11}$ M, most preferably less than $1.0\times10^{-12}$ M.

The binding affinity ($K_D$) can be measured by surface Plasmon resonance using, for example, a BIACORE system.

In an embodiment of the present invention, the first binding molecule may have an $EC_{50}$ value of 2.0 ug/ml or less for H1 subtype, 7.0 ug/ml or less for H2 subtype, 7.0 ug/ml or less for H5 subtype, or 4.0 ug/ml or less for H9 subtype.

In an embodiment of the present invention, the second binding molecule may have an $EC_{50}$ value of 40.0 ug/ml or less for H3 subtype, 212.0 ug/ml or less for H5 subtype, 8.0 ug/ml or less for H7 subtype, or 8.0 ug/ml or less for H9 subtype.

In an embodiment of the present invention, the composition may have an $EC_{50}$ value for 3.0 ug/ml or less for H1 subtype, 13.0 ug/ml or less for H2 subtype, 70.0 ug/ml or less for H3 subtype, 9.0 ug/ml or less for H5 subtype, 14.0 ug/ml or less for H7 subtype, or 6.0 ug/ml or less for H9 subtype.

The $EC_{50}$ value may be measured by a microneutralization test.

In an embodiment of the present invention, the first binding molecule comprises a polypeptide sequence comprising any one selected from the group consisting of: i) a sequence comprising, as determined according to the Kabat method, a CDR1 region of SEQ ID NO: 1, a CDR2 region of SEQ ID NO: 2, and a CDR3 region of SEQ ID NO: 3; ii) a sequence comprising, as determined according to the Kabat method, a CDR1 region of SEQ ID NO: 4, a CDR2 region of SEQ ID NO: 5, and a CDR3 region of SEQ ID NO: 6; iii) a sequence comprising, as determined according to the Kabat method, a CDR1 region of SEQ ID NO: 7, a CDR2 region of SEQ ID NO: 8, and a CDR3 region of SEQ ID NO: 9; iv) a sequence comprising, as determined according to the Kabat method, a CDR1 region of SEQ ID NO: 10, a CDR2 region of SEQ ID NO: 11, and a CDR3 region of SEQ ID NO: 12; v) a sequence comprising, as determined according to the Kabat method, a CDR1 region of SEQ ID NO: 13, a CDR2 region of SEQ ID NO: 14, and a CDR3 region of SEQ ID NO: 15; and vi) a sequence comprising, as determined according to the Kabat method, a CDR1 region of SEQ ID NO: 16, a CDR2 region of SEQ ID NO: 17, and a CDR3 region of SEQ ID NO: 18.

In an embodiment of the present invention, the first binding molecule comprises: a light-chain variable region comprising, as determined according to the Kabat method, a CDR1 region of SEQ ID NO: 1, a CDR2 region of SEQ ID NO: 2, and a CDR3 region of SEQ ID NO: 3; and a heavy-chain variable region comprising, as determined according to the Kabat method, a CDR1 region of SEQ ID NO: 4, a CDR2 region of SEQ ID NO: 5, and a CDR3 region of SEQ ID NO: 6.

In an embodiment of the present invention, the first binding molecule comprises: a light-chain variable region comprising, as determined according to the Kabat method, a CDR1 region of SEQ ID NO: 7, a CDR2 region of SEQ ID NO: 8, and a CDR3 region of SEQ ID NO: 9; and a heavy-chain variable region comprising, as determined according to the Kabat method, a CDR1 region of SEQ ID NO: 10, a CDR2 region of SEQ ID NO: 11, and a CDR3 region of SEQ ID NO: 12.

In an embodiment of the present invention, the first binding molecule comprises: a light-chain variable region comprising, as determined according to the Kabat method, a CDR1 region of SEQ ID NO: 13, a CDR2 region of SEQ ID NO: 14, and a CDR3 region of SEQ ID NO: 15; and a heavy-chain variable region comprising, as determined according to the Kabat method, a CDR1 region of SEQ ID NO: 16, a CDR2 region of SEQ ID NO: 17, and a CDR3 region of SEQ ID NO: 18.

In an embodiment of the present invention, the second binding molecule comprises any one sequence comprising any one selected from the group consisting of: i) a sequence comprising, as determined according to the Kabat method, a CDR1 region of SEQ ID NO: 19, a CDR2 region of SEQ ID NO: 20, and a CDR3 region of SEQ ID NO: 21; ii) a sequence comprising, as determined according to the Kabat method, a CDR1 region of SEQ ID NO: 22, a CDR2 region of SEQ ID NO: 23, and a CDR3 region of SEQ ID NO: 24; iii) a sequence comprising, as determined according to the Kabat method, a CDR1 region of SEQ ID NO: 25, a CDR2 region of SEQ ID NO: 26, and a CDR3 region of SEQ ID NO: 27; iv) a sequence comprising, as determined according to the Kabat method, a CDR1 region of SEQ ID NO: 28, a CDR2 region of SEQ ID NO: 29, and a CDR3 region of SEQ ID NO: 30; v) a sequence comprising, as determined according to the Kabat method, a CDR1 region of SEQ ID NO: 31, a CDR2 region of SEQ ID NO: 32, and a CDR3 region of SEQ ID NO: 33; vi) a sequence comprising, as determined according to the Kabat method, a CDR1 region of SEQ ID NO: 34, a CDR2 region of SEQ ID NO: 35, and a CDR3 region of SEQ ID NO: 36; vii) a sequence comprising, as determined according to the Kabat method, a CDR1 region of SEQ ID NO: 37, a CDR2 region of SEQ ID NO: 38, and a CDR3 region of SEQ ID NO: 39; and viii) a sequence comprising, as determined according to the Kabat method, a CDR1 region of SEQ ID NO: 40, a CDR2 region of SEQ ID NO: 41, and a CDR3 region of SEQ ID NO: 42.

In an embodiment of the present invention, the second binding molecule comprises: a light-chain variable region comprising, as determined according to the Kabat method, a CDR1 region of SEQ ID NO: 19, a CDR2 region of SEQ ID NO: 20, and a CDR3 region of SEQ ID NO: 21; and a heavy-chain variable region comprising, as determined according to the Kabat method, a CDR1 region of SEQ ID NO: 22, a CDR2 region of SEQ ID NO: 23, and a CDR3 region of SEQ ID NO: 24.

In an embodiment of the present invention, the second binding molecule comprises: a light-chain variable region comprising, as determined according to the Kabat method, a CDR1 region of SEQ ID NO: 25, a CDR2 region of SEQ ID NO: 26, and a CDR3 region of SEQ ID NO: 27; and a heavy-chain variable region comprising, as determined according to the Kabat method, a CDR1 region of SEQ ID NO: 28, a CDR2 region of SEQ ID NO: 29, and a CDR3 region of SEQ ID NO: 30.

In an embodiment of the present invention, the second binding molecule comprises: a light-chain variable region comprising, as determined according to the Kabat method, a CDR1 region of SEQ ID NO: 31, a CDR2 region of SEQ ID NO: 32, and a CDR3 region of SEQ ID NO: 33; and a heavy-chain variable region comprising, as determined according to the Kabat method, a CDR1 region of SEQ ID NO: 34, a CDR2 region of SEQ ID NO: 35, and a CDR3 region of SEQ ID NO: 36.

In an embodiment of the present invention, the second binding molecule comprises: a light-chain variable region comprising, as determined according to the Kabat method, a CDR1 region of SEQ ID NO: 37, a CDR2 region of SEQ ID NO: 38, and a CDR3 region of SEQ ID NO: 39; and a heavy-chain variable region comprising, as determined according to the Kabat method, a CDR1 region of SEQ ID NO: 40, a CDR2 region of SEQ ID NO: 41, and a CDR3 region of SEQ ID NO: 42.

In an embodiment of the present invention, the first binding molecule comprises: a light-chain variable region comprising, as determined according to the Kabat method, a CDR1 region of SEQ ID NO: 7, a CDR2 region of SEQ ID NO: 8, and a CDR3 region of SEQ ID NO: 9; and a heavy-chain variable region comprising, as determined according to the Kabat method, a CDR1 region of SEQ ID NO: 10, a CDR2 region of SEQ ID NO: 11, and a CDR3 region of SEQ ID NO: 12, and the second binding molecule comprises: a light-chain variable region comprising, as determined according to the Kabat method, a CDR1 region of SEQ ID NO: 25, a CDR2 region of SEQ ID NO: 26, and a CDR3 region of SEQ ID NO: 27; and a heavy-chain variable region comprising, as determined according to the Kabat method, a CDR1 region of SEQ ID NO: 28, a CDR2 region of SEQ ID NO: 29, and a CDR3 region of SEQ ID NO: 30.

In the present invention, the complementarity determining regions (CRDs) of variable domains were determined using a conventional method according to the system designed by Kabat et al. (see Kabat et al., Sequences of Proteins of Immunological Interest (5th), National Institutes of Health, Bethesda, Md. (1991)). CDR numbering used in the present invention was performed according to the Kabat method, but the present invention also encompasses binding molecules comprising CDRs determined by other methods, including the IMGT method, the Chothia method, and the AbM method.

In an embodiment of the present invention, the first binding molecule comprises a polypeptide sequence comprising any one selected from the group consisting of SEQ ID NOS: 43 to 48.

In an embodiment of the present invention, the first binding molecule comprises a light chain comprising a polypeptide sequence of SEQ ID NO: 43 and a heavy chain comprising a polypeptide sequence of SEQ ID NO: 44.

In an embodiment of the present invention, the first binding molecule comprises a light chain comprising a polypeptide sequence of SEQ ID NO: 45 and a heavy chain comprising a polypeptide sequence of SEQ ID NO: 46.

In an embodiment of the present invention, the first binding molecule comprises a light chain comprising a polypeptide sequence of SEQ ID NO: 47, and a heavy chain comprising a polypeptide sequence of SEQ ID NO: 48.

In an embodiment of the present invention, the second binding molecule comprises a polypeptide sequence comprising any one selected from the group consisting of SEQ ID NOS: 49 to 56.

In an embodiment of the present invention, the second binding molecule comprises a light chain comprising a polypeptide sequence of SEQ ID NO: 49, and a heavy chain comprising a polypeptide sequence of SEQ ID NO: 50.

In an embodiment of the present invention, the second binding molecule comprises a light chain comprising a polypeptide sequence of SEQ ID NO: 51, and a heavy chain comprising a polypeptide sequence of SEQ ID NO: 52.

In an embodiment of the present invention, the second binding molecule comprises a light chain comprising a polypeptide sequence of SEQ ID NO: 53, and a heavy chain comprising a polypeptide sequence of SEQ ID NO: 54.

In an embodiment of the present invention, the second binding molecule comprises a light chain comprising a polypeptide sequence of SEQ ID NO: 55, and a heavy chain comprising a polypeptide sequence of SEQ ID NO: 56.

In an embodiment of the present invention, the first binding molecule comprises a light chain comprising a polypeptide sequence of SEQ ID NO: 45, and a heavy chain comprising a polypeptide sequence of SEQ ID NO: 46, and the second binding molecule comprises a light chain comprising a polypeptide sequence of SEQ ID NO: 51, and a heavy chain comprising a polypeptide sequence of SEQ ID NO: 52.

In an embodiment of the present invention, the binding molecule is an antibody or an antigen binding fragment thereof. The antibody may have a drug attached thereto.

In an embodiment of the present invention, the composition may be used for the prevention or treatment of a disease caused by influenza virus.

In an embodiment of the present invention, the composition may be used for the diagnosis of a disease caused by influenza virus.

In an embodiment of the present invention, the composition may comprise a pharmaceutically acceptable excipient.

In an embodiment of the present invention, the composition may be in the form of a sterile injectable solution, a lyophilized formulation, a pre-filled syringe solution, an oral dosage form, a formulation for external use, or a suppository, but is not limited thereto.

The present invention also provides a method for treating a disease caused by influenza virus, the method comprising a step of administering a therapeutically effective amount of the composition to a subject having the disease.

The present invention also provides a method for diagnosing, preventing or treating a disease caused by influenza virus, the method comprising: step of i) administering therapeutically effective amounts of the first binding molecule and the second binding molecule at the same time to a subject having the disease; or step ii) administering a therapeutically effective amount of the first binding molecule to a subject having the disease, and then administering a therapeutically effective amount of the second binding molecule to the subject; or step iii) administering a therapeutically effective amount of the second binding molecule to a subject having the disease, and then administering a therapeutically effective amount of the first binding molecule to the subject.

In an embodiment, the present invention provides a method for treating a disease caused by influenza A virus, the method comprising the steps of: i) administering a therapeutically effective amount of the first binding molecule to a subject having the disease; and ii) subsequent to step i), administering a therapeutically effective amount of the second binding molecule to the subject.

In another embodiment, the present invention provides a method for treating a disease caused by influenza A virus, the method comprising the steps of: i) administering a therapeutically effective amount of the second binding molecule to a subject having the disease; and ii) subsequent to step i), administering a therapeutically effective amount of the first binding molecule to the subject.

In an embodiment of the present invention, the method for diagnosing, preventing or treating the disease may further comprise a step of administering an antiviral drug, a virus entry inhibitor or a virus adhesion inhibitor. The antiviral drug may be a neuraminidase inhibitor, a hemagglutinin (HA) inhibitor, a sialic acid inhibitor, an M2 ion channel inhibitor or an RNA polymerase inhibitor, but is not limited thereto.

The neuraminidase inhibitor may be Peramivir, Zanamivir, Oseltamivir or Laninamivir, but is not limited thereto.

The M2 ion channel inhibitor may be Amantadine or Rimantadine, but is not limited thereto.

The RNA polymerase inhibitor may be Favipiravir, but is not limited thereto.

The present invention also provides a method for preventing a disease caused by influenza virus, the method comprising a step of administering a therapeutically effective amount of the composition to a subject having the disease.

In an embodiment, the present invention provides a method for preventing a disease caused by influenza A virus, the method comprising the steps of: i) administering a therapeutically effective amount of the first binding molecule to a subject having the disease; and ii) a therapeutically effective amount of the second binding molecule to the subject.

In another embodiment, the present invention provides a method for preventing a disease caused by influenza A virus, the method comprising the steps of: i) administering a therapeutically effective amount of the second binding molecule to a subject having the disease; and ii) a therapeutically effective amount of the first binding molecule to the subject.

The present invention also provides a method for diagnosing influenza virus infection in a patient, the method comprising the steps of: i) bringing the composition into contact with a sample; and ii) detecting a reaction between the composition and the sample.

The present invention also provides a kit for diagnosing influenza virus, the kit comprising: i) the composition for diagnosing influenza virus; and ii) a container.

Advantageous Effects

The composition of the present invention, which comprises at least two influenza A virus-neutralizing binding molecules, maintains the neutralizing activities of the binding molecules against the respective subtypes without interference between the binding molecules, and, as a result, exhibits additive effects. The composition of the present invention exhibits synergistic effects even when it is administered in combination with a chemical compound. The composition of the present invention can effectively neutralize multiple influenza subtypes of both phylogenetic groups 1 and 2 and may be used in combination with a chemical compound, and thus is very useful for the prevention and treatment of a disease caused by influenza virus.

DESCRIPTION OF DRAWINGS

FIG. 1 is a graph showing the binding affinities of CT104, CT120 and CT123 antibodies for monomeric hemagglutinin (hereinafter referred to as "HA") and trimeric HA.

FIG. 2 is a graph showing the binding affinities of CT147, CT149, CT164 and CT166 antibodies for a monomeric HA subunit (HA1) and a trimeric HA.

FIG. 3 illustrates maps of pCT145 (A) and pCT147 (B) vectors:

A: pCT145 vector;

B: pCT147 vector;

pac: gene encoding Puromycin N-acetyl-tranferase (PAC); and

DS: dyad symmetry sequence (EBNA1 binds to a dyad symmetry (DS) element in oriP).

FIG. 4 is a map of an expression vector that expresses an anti-influenza A virus monoclonal antibody of the present invention.

FIGS. 5a to 5d shows the results of verifying the abilities of CT120 and CT149 antibodies to inhibit membrane fusion induced by HA exposed to low pH, using a cell line that expresses H1(H1N1), H2 (H2N2), H3(H3N2) or H5(H5N1) subtype HA.

FIG. 6a shows the results of an in vitro ADCC assay performed using the CT120 and CT149 antibodies of the present invention, and FIG. 6b shows the results of an in vitro CDC assay performed using the CT120 and CT149 antibodies of the present invention.

FIG. 7 shows the results of an animal test performed using a CT149 antibody having a mouse Fc.

FIG. 8a depicts an amino acid sequence and a schematic view, which show the A/Vietnam/1203/04 (H5N1) virus HA-binding site of a CT120 antibody, and FIGS. 8b and 8c depict amino acid sequences and schematic views, which show the A/Aichi/1968 (H3N2) and A/Anhui/1/2013(H7N9) HA protein-binding sites of a CT149 antibody, respectively.

FIG. 9 is a graph showing the results of verifying the binding affinities of antibodies (CT120, CT149, and a antibody mixture of CT120 and CT149) for HA by a CELISA assay using a cell line that expresses H1(H1N1), H3(H3N2) or H5(H5N1) subtype HA.

FIG. 10 shows the results of an animal test performed by administering CT120 and CT149 antibodies alone or in combination to mice in order to confirm the preventive and therapeutic effects of the antibodies against H1N1.

FIG. 11 shows the results of an animal test performed by administering CT120 and CT149 antibodies alone or in combination to mice in order to confirm the preventive and therapeutic effects of the antibodies against H3N2.

FIG. 12 shows the results of an animal test performed by administering CT120 and CT149 antibodies alone or in combination to mice in order to confirm the preventive and therapeutic effects of the antibodies against H5N1.

FIG. 13 shows the results of an animal test performed by administering a CT149 antibody to mice in order to confirm the preventive and therapeutic effects of the antibody against H7N9.

FIG. 14 shows the results of observing the change in the death rate of mice after Peramivir and an antibody against H1N1 virus or H3N2 virus were administered alone or in combination at non-optimal concentrations.

FIG. 15 shows the results of an MN test on a CT149 antibody and an antibody mixture of CT120 and CT149 against H7N9 (A/Anhui/1/2013, A/Shanghai/2/2013).

FIG. 16a shows the results of an MN test on a CT149 antibody and a mixed antibody of CT120 and CT149 against H7N9 (A/Shanghai/2/2013) wild-type, and FIG. 16b shows the results of an MN test on a CT149 antibody and an antibody mixture of CT120 and CT149 against NAI-resistant H7N9 (A/Shanghai/2/2013) R292K.

FIG. 17a shows the results of an MN test on a CT120 antibody and an antibody mixture of CT120 and CT149 against H1N1 (A/California/04/2009) wild-type, and FIG. 17b shows the results of an MN test on a CT120 antibody and an antibody mixture of CT120 and CT149 against NAI-resistant H1N1 (A/California/04/2009) H275Y.

FIG. 18a shows the results of immunofluorescent staining of CT120 and CT149 antibodies against A/Wisconsin/67/05 (H3N2) wild-type and an HA D19N mutant, and FIG. 18b shows the results of immunofluorescent staining of CT120 and a CT149 antibodies against A/Anhui/1/2013 (H7N9) wild-type and an HA D19N mutant.

BEST MODE

Hereinafter, terms used in the present invention will be defined as follows.

The term "influenza A viruses" as used herein refers to enveloped viruses belonging to the family Orthomyxoviridae and having a genome composed of eight negative-sense, single-stranded RNA (ribonucleic acid) segments. These influenza viruses are classified into types A, B and C, and the influenza A viruses are further divided into subtypes based on their major surface proteins HA (hemagglutinin) and NA (neuraminidase) 17 HAs and 10 NAs have been reported to date.

"H1 subtypes" described in the present invention include H1N1, H1N2, H1N3, H1N4, H1N5, H1N6, H1N7, H1N8, H1N9 and H1N10.

"H2 subtypes" described in the present invention include H2N1, H2N2, H2N3, H2N4, H2N5, H2N6, H2N7, H2N8, H2N9 and H2N10.

"H5 subtypes" described in the present invention include H5N1, H5N2, H5N3, H5N4, H5N5, H5N6, H5N7, H5N8, H5N9 and H5N10.

"H9 subtypes" described in the present invention include H9N1, H9N2, H9N3, H9N4, H9N5, H9N6, H9N7, H9N8, H9N9 and H9N10.

"H3 subtypes" described in the present invention include H3N1, H3N2, H3N3, H3N4, H3N5, H3N6, H3N7, H3N8, H3N9 and H3N10.

"H7 subtypes" described in the present invention include H7N1, H7N2, H7N3, H7N4, H7N5, H7N6, H7N7, H7N8, H7N9 and H7N10.

As used herein, the term "hemagglutinin" (hereinafter referred to as "HA") indicates the envelope glycoprotein of influenza virus. HA mediates the adsorption and penetration of influenza virus into a host cell. 17 HA subtypes have been reported to date.

As used herein, the term "binding molecule" refers either to an intact immunoglobulin comprising monoclonal antibodies, such as chimeric, humanized or human monoclonal antibodies, or to a variable domain, a substrate-binding enzyme, a receptor or a protein, which comprises an immunoglobulin fragment that competes with the intact immunoglobulin for specific binding to the binding partner of the immunoglobulin, for example, the monomeric HA or trimeric HA of influenza A virus. Regardless of structure, the antigen-binding fragment binds with the same antigen that is recognized by the intact immunoglobulin. An antigen-binding fragment may comprise a peptide or polypeptide comprising an amino acid sequence consisting of at least 2, 20, 25, 30, 35, 40, 50, 60, 70, 80, 90, 100, 125, 150, 175, 200, or 250 contiguous amino acid residues of the amino acid sequence of the binding molecule. "Antigen-binding fragments" include, inter alia, Fab, F(ab'), F(ab)$_2$, Fv, dAb, Fd, complementarity determining region (CDR) fragments, single-chain antibodies (scFv), bivalent single-chain antibodies, single-chain phage antibodies, diabodies, triabodies, tetrabodies, polypeptides that contain at least one fragment of an immunoglobulin that is sufficient to confer specific antigen binding to the polypeptide, etc. The above fragments may be produced synthetically or by enzymatic or chemical cleavage of intact immunoglobulins or they may be genetically engineered by recombinant DNA techniques. The methods of production are well known in the art.

As used herein, the term "pharmaceutically acceptable excipient" means any inert substance that is combined with an active molecule such as a drug, agent, or binding molecule for preparing an agreeable or convenient dosage form. The pharmaceutically acceptable excipient is an excipient that is non-toxic to recipients at the used dosages and concentrations, and is compatible with other ingredients of the formulation comprising the drug, agent or binding molecule.

As used herein, the term "therapeutically effective amount" refers to an amount of the binding molecule that is effective for preventing or treating a condition resulting from infection with influenza A virus.

The composition comprising the binding molecules according to the present invention may be formulated as oral dosage forms, including powder, granule, tablet, capsule, suspension, emulsion, syrup and aerosol formulations, as well as formulations for external use, suppositories, sterile injectable solutions, pre-filled syringe solution or lyophilized formulations. Specifically, the composition of the present invention may be formulated with commonly used diluents or excipients, such as fillers, extenders, binders, wetting agents, disintegrants, surfactants, etc. Solid formulations for oral administration include tablets, pills, powders, granules, capsules and the like, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like can be used. As the base of the suppositories, witepsol, Macrogol, Tween 61, cacao butter, laurin fat, glycerogelatin and the like can be used.

The binding molecules that are used in the diagnostic composition of the present invention are preferably detectably labeled. A variety of techniques are available for labeling biomolecules, are well known to the person skilled in the art and are considered to be within the scope of the present invention. Such techniques are, e.g., described in Tijssen, 'Practice and theory of enzyme immuno assays', Burden, R H and von Knippenburg (Eds), Volume 15 (1985), Basic methods in molecular biology; Davis L G, Dibmer M D; Battey Elsevier (1990), Mayer et al., (Eds) 'Immuno-chemical methods in cell and molecular biology' Academic Press, London (1987), 'Methods in Enzymology', Academic Press, Inc.

There are many different labels and methods of labeling known to those of ordinary skill in the art. Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}$P or $^{125}$I), biotin, digoxygenin, colloidal metals, chemi- or bioluminescent compounds (like dioxetanes, luminol or acridiniums). Labeling procedures, such as covalent coupling of enzymes or biotinyl groups, iodinations, phosphorylations, biotinylations, etc., are well known in the art.

Detection methods include, but are not limited to, autoradiography, fluorescence microscopy, direct and indirect enzymatic reactions, etc. Commonly used detection assays include radioisotopic or non-radioisotopic methods. These include, inter alia, RIA (Radioisotopic Assay) and IRMA (Immune Radioimmunometric Assay), EIA (Enzym Immuno Assay), ELISA (Enzyme Linked Immuno Assay), FIA (Fluorescent Immuno Assay), and CLIA (Chemiluminescent Immune Assay).

The antibody according to the present invention may be used in the form of antibody-drug conjugates. The use of antibody-drug conjugates (ADC), i.e. immunoconjugates, for the local delivery of drugs, allows targeted delivery of the drug moiety to infected cells, because administration of unconjugated drug agents may result in unacceptable levels of toxicity to normal cells. The maximal efficacy and minimal toxicity of ADC can be achieved by increasing the selectivity of polyclonal and monoclonal antibodies (mAbs) as well as drug-linking and drug-releasing properties.

Conventional means of attaching, i.e. linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody, thereby generating a heterogeneous antibody-drug conjugate mixture. Depending on reaction conditions, the heterogeneous mixture typically contains a distribution of antibodies with from 0 to about 8 or more, attached to drug moieties. In addition, each subgroup of conjugates with a particular integer ratio of drug moieties to antibody is a potentially heterogeneous mixture where the drug moiety is attached at various sites on the antibody. Antibodies are large, complex and structurally diverse biomolecules, often with many reactive functional groups. Their reactivities with linker reagents and drug-linker intermediates are dependent on factors such as pH, concentration, salt concentration, and co-solvents.

In the present invention, the reactivities of a cocktail composition, obtained by mixing antibodies filed for patent protection (Korean Patent Application No. 10-2011-0020061 and Korean Patent Application No. 10-2012-0107512), with the subtype viruses of phylogenetic group 1 or 2, were measured by a microneutralization test (hereinafter referred to as "MN test"). Among them, CT120 having specific neutralizing activity against group 1 was mixed with CT149 showing neutralizing activity against some viruses of group 1 and the viruses of group 2, and the binding affinities and neutralizing activities of CT120 and CT149 before and after mixing were analyzed. Korean Patent Application No. 10-2011-0020061 and Korean Patent Application No. 10-2012-0107512, filed by the applicant, are incorporated herein by reference.

The binding affinities of antibodies were measured by a surface Plasmon resonance-based method and a CELISA (Cellular Enzyme-Linked Immunosorbent Assay) assay employing a cell line that expresses H1, H3 or H5. As a result, CT120 and CT149 did bind to the cell lines expressing H1 and H5 HAs, respectively, and a mixture of CT120 and CT149 showed a binding affinity similar to that of each of CT120 and CT149. CT149 showed binding affinity in a CELISA assay performed using a cell line expressing H3 HA, but CT120 showed no binding affinity. When a mixture of CT120 and CT149 was analyzed by a CELISA assay, it was found that CT120 did not interfere with the binding of CT149.

The neutralizing activities of CT120 and CT149 before and after mixing were measured by the microneutralization test. As a result, it was found that CT120 and CT149 showed the respective original neutralizing activities without interference therebetween, indicating that CT120 and CT149 showed neutralizing activities against all the influenza A viruses of group 1 and group 2.

In order to examine neutralizing activity in vivo, CT120 and CT149 or a mixture of CT120 and CT149 were administered to mice before and after the mice were infected with influenza A virus. As a result, it was seen that administration of the antibody mixture (referred herein to as CT-P27) reflected the effect of each of the antibodies or showed the combined effects of the antibodies, and the antibodies did not interfere with each other.

CT120 and CT149 showed an enhanced neutralizing effect when they were administered in a mixture or administered in combination with a chemical compound. Peramivir is neuraminidase inhibitor that is used against influenza A infection. When mice were infected with influenza A virus and an amount of CT120 or CT149 difficult to exhibit a neutralizing effect was administered in combination with a low concentration of Peramivir to the mice, an increased effect compared to that in the administration of CT120 or CT149 alone appeared.

Accordingly, in the present invention, antibodies (CT104, CT120 and CT123) effective against the influenza A viruses of group 1, which are represented by CT120, and antibodies (CT147, CT149, CT164, and CT166) effective against the influenza A viruses of group 2, which are represented by CT149, were mixed with one another and administered. As a result, it was found that the antibody mixtures showed neutralizing effects against all the influenza A viruses of groups 1 and 2. In addition, it was found that, when each of the antibodies was administered in combination with a chemical therapeutic agent, it showed an increased neutralizing effect.

Hereinafter, the present invention will be described in detail with reference to examples. It is to be understood, however, that these examples are for illustrative purposes and are not intended to limit the scope of the present invention. References cited in the present invention are incorporated herein by reference.

EXAMPLES

Example 1: Isolation of PBMC from Blood of Patients Who Recovered from Flu

A recovered patient group consisted of patient volunteers who were 2-4 weeks after confirmation of new flu infections. The volunteers were confirmed to have no influenza virus (H1N1) in their blood and had an antibody against the new influenza virus. This study was performed under the approval of the Institutional Review Board (IRB). This patients group had the following characteristics: (1) the patients were not vaccinated against seasonal flu; (2) the patients were negative for other infectious viruses, that is, HBsAg, and were negative for anti-HCV antibody and anti-HIV antibody; (3) the patient's plasma was negative for RT-PCR for the influenza virus H1N1 subtype; (4) the patient's serum showed a titer of 1:160 or higher in ELISA assays for the HA(H1N1) of the influenza A virus H1N1 subtype. About 100 ml of whole blood was collected from the volunteers, and peripheral blood mononuclear cells (PBMCs) were isolated from the collected blood using Lymphoprep™ (Axis-Shield, Norway, 1114545). The isolated PBMCs were washed three times with phosphate-buffered saline, suspended in KM banker II freezing medium (Cosmobio, Japan, KOJ-16092010) at a concentration of $2 \times 10^7$ cells/ml, and stored in a liquid nitrogen tank.

Example 2: Primary Screening of Monoclonal Antibodies

B cells that secrete antigen-specific antibodies were screened using the method described by Jin et al. (Jin A. et al., 2009. Nat. Med. 15, 1088-1092). Briefly, the PBMCs isolated in Example 1 were added to each well of a prepared microarray chip at a density of one cell/well. Antibodies secreted from the single cells were confirmed by the pre-coated anti-human IgG antibody. Whether the screened antibody-secreting cells secreted HA-binding antibodies was analyzed by ELISPOT (enzyme linked immunospot assay: Sedgwick J. D., 2005, Methods Mol Biol. Vol. 302, pp. 314) using the labeled HA antigen. The complete sequences of the heavy-chain and light-chain genes of the antibodies from the individual antibody-secreting cells were obtained by a reverse transcription-polymerase chain reaction (RT-PCR). The obtained heavy-chain and light-chain DNAs were inserted into pcDNA 3.1(+) expression vectors (Invitrogen, USA, V790-20) to prepare expression vectors that produce each of the heavy chain and light chain of the antibodies. The prepared expression vectors were transfected into CHO cells. Then, using the antibodies produced in the transfected CHO cells, antibodies binding to HA were primarily selected by the HA-ELISA method described in Example 3 below. Herein, all the antibodies showing a reaction with HA were primarily screened without serially diluting the antibody samples.

Example 3: Secondary Screening of Monoclonal Antibodies and Antibody Production

In order to secondarily screen monoclonal antibodies, which have a high ability to bind to the HA of H1N1 influenza virus, from the primarily screened antibodies, HA-ELISA was performed using monomeric HA and trimeric HA. A recombinant monomeric HA1 from influenza A virus was purchased from Sino Biological Inc. (China). The monomeric HA (11055-V08H) of the purchased A/CA/04/09 (H1N1) consisted of an extracellular domain (met1-gln529) of HA comprising 10 polyhistidine residues at the C-terminus and the recombinant HA1 subunit (11056-V08H1) of A/Brisbane/10/07(H3N2) consisted of the N-terminal fragment (Met1-Arg345) of the HA comprising polyhistidine residues at the C-terminus and was produced in transfected human cells. The recombinant trimeric HAs (FR-180 and FR-61) of A/CA/04/09 (H1N1) and A/Brisbane/10/07 (H3N2) were provided by IRR (Influenza Reagent Resource, USA). Each of the trimeric HA comprised a thrombin cleavage site at the C-terminus, a trimerizing domain (foldon) and six histidine residues and was produced using a baculovirus system.

The reactivity of the antibody with the HA antigen was measured by ELISA using the HA and the antibody. Specifically, 50 μl of each of monomeric HA antigen and trimeric HA antigen (250 ng/ml) was first adsorbed onto each well of a 96-well microtiter plate (Nunc, Denmark, 449824). The plate was blocked with phosphate-buffered saline (Teknova, USA, D5120) containing 1% bovine serum albumin (BSA), and then a 3-fold serially diluted antibody sample (starting concentration: 1 μg/ml) was added to each well of the plate. Next, the plate was incubated at room temperature for 1 hour, and then treated with peroxidase-labeled goat anti-human gamma antibody (Zymed, USA, 62.8420). After incubation for 1 hour at room temperature, the plate was incubated with tetramethylbenzydine (TMB; Sigma-Aldrich, USA, T0440), and the incubation was stopped by adding 1N HCl. The absorbance at 450/570 nm was measured using a plate reader (Spectramax plus 384, Molecular Device), and the antigen-antibody reactivity was graphically expressed using Graphpad prism program (GraphPad Software Inc. USA).

As shown in FIG. 1, the CT104, CT120 and CT123 antibodies showed high reactivity with the trimeric HA of A/CA/04/09(H1N1), but showed little or no reactivity with the monomeric HA.

As shown in FIG. 2, the CT147, CT149, CT164 and CT166 antibodies did easily bind to the trimeric HA of A/Brisbane/10/07 (H3N2), but did not bind to the HA1 subunit. This suggests that the screened antibodies do not bind to the epitope of previously known HA1, but have the ability to bind only to the boundary between the HA1 and HA2 segments, or to HA2 or to HA with a normal conformation.

On the basis of the results shown in FIGS. 1 and 2, from the primarily screened antibodies, antibodies showing high binding affinities for the trimeric HA were secondarily selected. In order to increase the expression levels of the secondarily selected antibodies, these antibody genes were recloned from the pcDNA vectors into MarEx expression vectors (constructed and patented by Celltrion, Inc.) in the following manner. After recloning, the MarEx expression vectors containing the antibody genes were used to produce antibodies required for a microneutralization test (MN test) and a haemagglutination inhibition test (HI test).

The original pcDNA vectors containing each of the heavy-chain genes and light-chain genes of the secondarily selected antibodies were treated with the restriction enzymes NheI and PmeI to obtain heavy-chain genes and light-chain genes. The obtained heavy-chain genes and light-chain genes were respectively inserted into pCT145 vectors and pCT147 vectors, which had been treated with the same restriction enzymes. The pCT145 and pCT147 vectors were constructed by Celltrion, Inc., in order to clone the heavy chain and light chain of each of the antibodies, respectively (FIG. 3). Next, in order to construct expression vectors containing a heavy-chain transcription unit (promoter-heavy chain gene-poly A) together with a light-chain transcription unit (promoter-light chain gene-poly A), the pCT145 vectors containing the heavy-chain genes were treated with the restriction enzymes PacI and AscI to obtain heavy-chain transcription units, and then the pCT147 vectors containing the light-chain genes were treated with the same restriction enzymes, and the heavy-chain transcription units were inserted therein. Then, vectors containing both the heavy-chain transcription unit and the light-chain transcription unit were screened using restriction enzymes (FIG. 4). The screened vectors were extracted using an Endofree plasmid maxi kit (QIAGEN, Germany, 12362), and the nucleotide sequences of portions of the extracted DNA samples were analyzed, thereby determining the nucleotide sequences of the antibodies.

Next, the DNA of the extracted antibodies was transfected into a suspension culture of an F2N cell line (refer to Korean Patent No. 10-1005967) (prepared by Celltrion, Inc., Korea), thereby preparing a transient cell line producing monoclonal antibodies. The transfection was performed in the following manner. Transient transfection of the cells was carried out using the cationic polymer FreeStyle™ Max (Invitrogen, USA, 16447-100) according to the manufacturer's instruction. On the day before transfection, F2N cells cultured in EX-CELL 293 serum-free media (SAFC, LIK, 14571C; hereinafter referred to as "EX-CELL 293 media") were centrifuged and suspended at a cell concentration of $1\times10^6$ cells/ml in modified EX-CELL 293 medium (SAFC, LIK, 65237; made to order), and 80 ml of the cell suspension was seeded into a 250 ml Erlenmeyer flask, or 200 ml of the cell suspension was seeded into a 1-liter Erlenmeyer flask. On the day of transfection, in the case in which 80 ml of the cell suspension was seeded, each of 100 μg of a monoclonal antibody-encoding DNA and 100 μl of FreeStyle™ Max reagent was diluted to a volume of 1.6 ml using OptiPRO SFM II medium (Invitrogen, USA, 12309), followed by gentle stirring. In the case in which 200 ml of the cell suspension was seeded, each of 250 μg of DNA and 250 μg of FreeStyle™ Max reagent was diluted to a volume of 4 ml using OptiPRO SFM II medium, followed by gentle stirring. Immediately after the stirring process, the solution containing FreeStyle™ Max reagent diluted therein was mixed with the solution containing DNA diluted therein, and the mixed solution was incubated at room temperature for 19 minutes. During incubation at room temperature for 19 minutes, the seeded F2N cells were diluted to a cell concentration of $0.8\times10^6$ cells using fresh modified EX-CELL 293 medium. After incubation for 19 minutes, the F2N cells were treated and transfected with the mixed solution containing DNA and FreeStyle™ Max reagent. On the day after transfection, the same amount of EX-CELL 293 medium was added to the transfected cells which were then incubated for 7-8 days, thereby producing monoclonal antibodies.

Example 4: Examination of In Vitro Neutralizing Activity Against Viruses

The antibodies screened by the present inventors were subjected to a microneutralization (MN) test in order to examine their neutralizing activity against various influenza viruses.

Example 4-1

Culture of MDCK Cell Line and Determination of Virus Concentration

As the Madin-Darby canine kidney (MDCK) cell line, the London line (MDCK-L) was used. The MDCK cell line was cultured in a 5% $CO_2$ humidified incubator at 37° C. using a DMEM medium (Gibco, USA, 11965) containing 10% FBS (Atlas Biologicals, USA, F0500A), 1× pecinillin/streptomycin (Gibco, USA, 15140), 25 mM HEPES (Gibco, USA, 15630) and 2 mM L-glutamine (Gibco, USA, 25030).

Virus concentration was quantified by a cell-based ELISA method to determine the median tissue culture infective dose ($TCID_{50}$). The determination of virus concentration was performed in the following manner. First, a virus stock was serially diluted 10-fold with a virus diluent [DMEM (Gibco, USA), 3% BSA (Gibco, USA, 15260), 1× penicillin/streptomycin (Gibco, USA), and 25 mM HEPES (Gibco, USA)], and 100 μl of the diluted virus was added to each well of a 96-well plate. As a negative control, a virus diluent containing no virus was used. Then, the MDCK cell line that was being cultured was separated from the culture incubator by treatment with trypsin, and then treated with MDCK culture medium to neutralize the trypsin. Next, the cell pellets were washed twice with phosphate-buffered saline, and then diluted with a virus diluent to a cell concentration of $5 \times 10^5$ cells/ml. 3-4 μg/ml of TPCK-trypsin (Sigma, USA) was added to the 96-well plate containing the virus, and then immediately, 100 μl of the MDCK cell line was added to each well of the plate and incubated in a 5% $CO_2$ humidified incubator at 37° C. for 20 hours. The incubated plate was washed once with phosphate buffered saline, and then 200 μl of a mixed solution of cold acetone: phosphate buffered saline (PBS) (80:20) was added to each well of the plate. Next, the cells were fixed for 8 minutes, and the plate was dried at room temperature for 20 minutes. Each well of the plate was washed twice with 200 μl of phosphate buffered saline. Biotinylated anti-nuclear protein (NP) monoclonal antibody (Milipore, USA, MAB8257B) was diluted 2,000-fold with 1% BSA-containing phosphate buffered saline (0.1% Tween 20), and 100 μl of the dilution was added to each well of the plate and incubated at room temperature for 1 hour. The plate was washed three times with 200 μl/well of phosphate buffered saline, and then 100 μl of a 20,000-fold dilution of streptavidin-HRP-conjugated antibody in 1% BSA-containing phosphate buffered saline was added to each well of the plate and incubated at room pressure for 1 hour. After washing the plate four times with phosphate buffered saline, 100 μl of TMB solution was added to each well of the plate, and the plate was developed at room temperature for 10 minutes and treated with sulfuric acid to stop the color development, after which the $OD_{450}$ of each well was measured. Based on the measured $OD_{450}$, $TCID_{50}$ was calculated using the method of Reed & Muench (The American 1938).

Example 4-2: MN Test

Each antibody was diluted with a virus diluent to a concentration of 10 μg/ml. From this initial concentration, the antibody dilution was serially diluted 2-fold with a virus diluent, and 50 μl of each of the dilutions was added to each well of a 96-well plate. Also, 50 μl of viruses were added to each well of the plate at a concentration corresponding to 100 $TCID_{50}$ and were incubated in a 5% $CO_2$ humidified incubator at 37° C. for 1 hour. Next, 3-4 μg/ml of TPCK-trypsin (Sigma, USA, T1426) was added to each well, and 100 μl of the treated MDCK cells were added to each well, followed by incubation in a 5% $CO_2$ humidified incubator at 37° C. for 20 hours. After incubation for 20 hours, an MN test was carried out according to the same method as the virus quantification method described in Example 4-1, thereby determining the $OD_{450}$ value of each well. The wells showing $OD_{450}$ values higher than that of the well introduced only with the cells were determined to be infected with viruses. Among $OD_{450}$ values for each antibody at which no virus antigen was detected, the lowest concentration (μg/ml) of the antibody is shown in Table 1 below, and the lower concentration of the antibody means the higher neutralizing activity against virus.

The neutralizing abilities of specific antibodies against influenza A virus subtype H1 are shown in Table 1 below, and the neutralizing abilities of specific antibodies against influenza A virus subtype H3 are shown in Table 2 below. Among these antibodies, CT120 and CT149 having better effects were subjected to a microneutralization test using the influenza A viruses of various groups. As a result, CT120 showed a neutralizing effect against the influenza A viruses of group 1, and CT149 showed a neutralizing effect against some viruses of group 1 and the influenza A viruses of group 2 (Table 3).

TABLE 1

Results of microneutralization test performed using antibodies and influenza A virus subtype H1

| | H1 Pandemic | | H1 Seasonal | |
| --- | --- | --- | --- | --- |
| mAb ID | (A/Texas/ 05/2009) | (A/New York/ 18/2009) | (A/Solomon Islands/2006) | (A/Ohio/83) |
| CT104 | 0.313 | 0.625 | 0.625 | 0.313 |
| CT120 | 0.313 | 0.313 | 0.625 | 0.156 |
| CT123 | 0.313 | 0.625 | 1.25 | 0.313 |

\* unit: μg/ml

TABLE 2

Results of microneutralization test performed using antibodies and influenza A virus subtype H3

| mAb ID | A/Wisconsin/67/05 | A/Hong Kong/68 | A/Brisbane/10/07 |
| --- | --- | --- | --- |
| CT147 | 2.5 | 2.5 | 0.625 |
| CT149 | 1.25 | 2.5 | 1.25 |
| CT164 | 2.5 | 1.25 | 0.625 |
| CT166 | 5 | 2.5 | 1.25 |

\* unit: μg/ml

TABLE 3

Results of microneutralization test performed using influenza A viruses of group 1 and group 2

| Group | subtype | virus | CT120 | CT149 |
| --- | --- | --- | --- | --- |
| 1 | H1N1 | A/Texas/05/2009-RG15 | 0.156 | >10 |
| | | A/New York/18/2009-RG18 | 0.313 | >10 |
| | | A/Ohio/07/2009 | 0.039 | 5 |
| | | A/Solomon Islands/2006 | 0.625 | >10 |
| | | A/Ohio/83 | 0.156 | >10 |
| | H2N2 | A/Ann Arbor/6/60 ca | 0.312 | >10 |
| | H5N1 | A/Vietnam/1203/04 | 0.156 | 2.5 |
| | | Anhui/1/05 | 0.625 | 0.625 |
| | H9N2 | A/ck/HK/G9/97 | 0.078 | 0.312 |
| | | A/Green-winged teal/209/TX/2009 | 0.625 | 0.156 |
| 2 | H3N2 | A/Wisconsin/67/05 | >10 | 1.25 |
| | | A/Hong Kong/68 | NA | 2.5 |
| | | A/Brisbane/10/07 | >20 | 1.25 |
| | H7N2 | A/turkeyNirginia/02 | >20 | 10 |

\* unit: μg/ml

Example 5: Examination of the Ability of Antibody to Inhibit Hemagglutination Reaction Caused by Viruses Because the antibodies of the present invention are neutralizing antibodies targeting the HA of viruses, the mechanism by which the antibodies of the present invention show neutralizing activity against the functions of HA was examined. One of the functions of HA is to bind to the receptor on the cell surface to allow the virus to adhere to the cell. Because this function can be observed by a hemagglutination reaction, the inhibitory effect of the antibody against a hemagglutination reaction induced by HA was examined. For this, the antibody was serially diluted 2-fold on a V-bottom 96-well plate, and viruses having 4-fold HA units were added to and mixed with the antibody. Next, the plate was incubated at room temperature for 30 minutes, and then 1% avian red blood cells were added to each well of the plate. The hemagglutination inhibition end point was determined as the lowest antibody concentration at which no hemagglutination reaction was observed.

As a result, all the antibodies against influenza A virus subtype H1 (Table 4) or the antibodies against influenza A virus subtype H3 (Table 5) did not inhibit hemagglutination for A/Texas/05/2009 and A/New York/18/2009, A/Brisbane/10/07, against which the antibodies showed neutralizing effects in the MN test, even at high concentrations (>20 µg/ml).

TABLE 4

Results of hemagglutination inhibition test performed using antibodies and influenza A virus H1 subtype

| mAb ID | A/Texas/05/2009 | A/New York/18/2009 |
|---|---|---|
| CT104 | >20 | >20 |
| CT120 | >20 | >20 |
| CT123 | >20 | >20 |

* unit: µg/ml

TABLE 5

Results of hemagglutination inhibition test performed using antibodies and influenza A virus H3 subtype

| mAb ID | A/Brisbane/10/07 |
|---|---|
| CT147 | >20 |
| CT149 | >20 |
| CT164 | >20 |
| CT166 | >20 |

* unit: µg/ml

Example 6: Examination of the Ability of Antibody to Inhibit Membrane Fusion

In order to examine the mechanism of action of the neutralizing antibody, the inhibitory effect of the antibody against another function (membrane fusion ability) of HA was examined. When HA is exposed to a low-pH environment after the virus entered cells by endocytosis, it functions to induce the membrane fusion between the endosome and envelope of the virus so that the genome of the virus can penetrate the cells. In order to reproduce this function in vitro, CHO cell lines expressing the HA of A/CA/04/09 (H1N1), A/Japan/305-11957 (H2N2), A/Brisbane/10/07 (H3N2) or A/Vietnam/1203/04 (H5N1) were developed and used in a test. When each of the cell lines is exposed to low pH, the cell membranes are fused to form syncytia. Specifically, each of the cell lines was seeded into a 6-well plate at a density of 1×10⁵ cells per well, and 10% FBS-containing DMEM/F12 medium was added to each well, followed by incubation in a 5% $CO_2$ humidified incubator at 37° C. for 2 days. Next, the cells were washed with PBS and incubated in FBS-free DMEM/F12 medium for 30 minutes, after which the cells were treated with 4 µg/ml of TPCK-Trypsin for 5 minutes to activate HA. Next, the medium was replaced with 10% FBS-containing DMEM/F12 medium, followed by incubation for 20 minutes. The cells were treated with 20 µg/ml of each of the neutralizing antibodies, and then incubated in a 5% $CO_2$ humidified incubator at 37° C. for 1 hour. The incubated cells were washed with PBS, and then treated with low-pH buffer (150 mM NaCl, 10 mM Hepes, pH 5.0) for 6 minutes. Next, the medium was replaced with 10% FBS-containing DMEM/F12 medium, followed by incubation for 1 hour. Next, the cells were washed with PBS, fixed with methanol, and then stained with trypan blue, and the degree of membrane fusion of the cells was observed with a microscope. As a result, it was shown that CT120 inhibited the membrane fusion of the CHO cell line expressing the HA of A/CA/04/09 (H1N1), A/Japan/305-11957 (H2N2) or A/Vietnam/1203/04 (H5N1), and CT149 inhibited the membrane fusion of the cell line expressing the HA of A/CA/04/09 (H1N1), A/Brisbane/10/07 (H3N2) or A/Vietnam/1203/04 (H5N1) (FIGS. 5a to 5d).

Thus, the results of Examples 5 and 6 indicated that the antibodies of the present invention exhibit neutralizing effects against viruses according to the mechanism by which they bind to HA to inhibit membrane fusion.

Example 7: Examination of Fc Function Mediated Anti-Viral Effect of Antibodies

Example 7-1: In Vitro ADCC Assay

To measure the antibody dependent cell cytotoxicity (ADCC) of the antibody, a calcein-AM release assay was used.

Calcein-AM was added to a CHO K1 cell line expressing the HA of influenza H1N1 (A/California/04/2009) in order to use the cell line as target cells. The target cells having calcein-AM added thereto were treated with varying concentrations of each of CT120, CT149 and the negative control CT-P6 (anti-Her2 antibody), and then treated with effector cells. After incubating the plate at 37° C. for 4 hours, the plate was centrifuged, and the supernatant was transferred to an opaque plate, followed by measurement of fluorescence. Percent (%) cytotoxicity at each antibody concentration was calculated using maximal release (MR) and spontaneous release (SR).

As shown in FIG. 6a, the negative control showed no cytotoxicity at varying antibody concentrations, but CT120 and CT149 showed higher cytotoxicities (i.e., higher ADCC) at higher concentrations, and CT120 showed higher cytotoxicity than CT149.

Example 7-2: In Vitro CDC Assay

Complement dependent cell cytotoxicity (CDC) was measured using a cell counting kit-8 (CCK-8) in which absorbance increases in proportion to the number of viable cells.

Specifically, a CHO K1 cell line expressing the HA of influenza H1N1 (A/California/04/2009) was attached to a plate and used as target cells. The target cells were treated with varying concentrations of each of CT120, CT149 and the negative control CT-P6, and then treated with human serum as the source of complement. The plate was incubated at 37° C. for 2 hours, and then treated with CCK-8 and incubated overnight, after which the absorbance of the plate was measured. Percent (%) cytotoxicity at each antibody concentration was calculated using the maximum absorbance and minimum absorbance of the test system.

As shown in FIG. 6b, the negative control showed no cytotoxicity at varying antibody concentrations, but CT120 and CT149 showed higher cytotoxicities (i.e., higher ADCC) at higher concentrations.

Example 7-3: Production of CT149 Antibody Having Mouse Fc

In order to make a CT149 antibody having mouse Fc, five mouse IgG1 sequences (GenBank Accession Nos. L27437.1, L35037.1, AB097849.1, Q724328.1 and M745099.1) in the NCBI database were compared to one another, and the constant region sequence of AB097849.1 having the highest identity to other sequences was selected as the mouse IgG1 constant region. As the mouse IgG2a constant region, the constant region sequence of X70423.1 was optionally selected, because two mouse IgG2a sequences (GenBank Accession Nos. X70423.1 and AB097847.1) in the NCBI database had the same amino acid sequence, even though there was a difference of 1 bp between the two sequences. In addition, four mouse kappa sequences (GenBank Accession Nos. U65535.1, BC028540.1, BC094013.1 and BC002112.1) in the NCBI database were compared to one another, and as a result, the kappa sequences were found to be identical to one another.

The selected mouse IgG1 and IgG2a constant regions were synthesized, a chimeric IgG1 heavy-chain having a human variable region and a mouse constant region was obtained by overlapping PCR with the human variable region of CT149. To obtain a mouse light-chain, a kappa constant region from hybridoma RNA was obtained by RT-PCR, and then a chimeric light-chain (kappa) having a human variable region and a mouse constant region was obtained by overlapping PCR. It was found that the sequences of the obtained heavy-chain and light-chain were identical to the sequences in the NCBI database.

The prepared chimeric antibody genes were cloned into expression vectors (constructed by Celltrion Inc.) which were then introduced into CHOK1 cells. The cells were incubated in SFM4CHO medium (Hyclone, Cat. No.: SH30549.02) containing 8 ug/ml of puromycin, and stable cell lines were selected from the cells. The selected cell lines were batch-cultured to produce IgG1 form and IgG2a form antibodies having mouse Fc.

Example 7-4: Animal Test Using CT149 Having Mouse Fc

Each mouse group consisting of five mice was intranasally infected with 5 $LD_{50}$ of A/California/04/09 virus. At 24 hours after viral infection, 3 mg/kg of each antibody was administered to each mouse by intraperitoneal injection, and the survival rate of the mice was measured. The antibodies used in the experiment had the antigen binding site of CT149 and the human Fc or the mouse IgG1 or IgG2a Fc. In the case of mouse antibodies, IgG2a has a higher affinity for FcgR than IgG1 (Bruhn P, 2012, Blood, 119(24):5640-5649).

As a result, as shown in FIG. 7, CT149 having the mouse IgG2a Fc showed a higher survival rate compared to other antibodies. Thus, it could be seen that the antibody of the present invention exhibited its effect by the Fc even in vivo.

Example 8: Determination of Sites that CT120 and CT149 Antibodies Bind to H5 and H3 Subtypes HA In order to determine the HA-binding site of the antibody of the present invention, the amino acid sequence of an antibody fragment that binds to HA protein was analyzed by X-ray crystallography (FIGS. 8*a* and 8*b*). As a result, the major element of the CT120 epitope was localized to the helix side of the HA2 subunit of A/Vietnam/1203/04 (H5N1) (FIG. 8*a*). CT149 was localized to the helix side of the HA2 subunit of A/Aichi/1968 (H3N2) while it did bind to other monomers adjacent to the HA2 subunit, indicating that it did bind to three subunits in a single HA trimer (FIG. 8*b*).

Example 8-1: Expression of Recombinant HA Protein

In order to produce a recombinant HA protein for use in X-ray diffraction analysis, the ectodomain of the HA gene of each of A/Vietnam/1203/04 (H5N1) and A/Aichi/1968 (H3N2) viruses was cloned into the baculovirus vector pAcGP67-A (BD Pharmingen). A Tricoplusia ni (High 5) cell line (Invitrogen) was infected with baculovirus (constructed using the vector) at an MOI (multiplicity of infection) of 5-10 at 28° C. for 72 hours. The expressed and secreted HA protein was purified from the collected medium by metal affinity chromatography and size exclusion gel filtration chromatography (Superdex 200 16/60 column; GE Healthcare). For crystallization, the purified HA was incubated with 3 units of thrombin at 4° C. for 18 hours to remove the C-terminal foldon/histidine tag.

Example 8-2: Purification of Antibody Fragment

Each of CT120 and CT149 antibodies was mixed with Papain (Roche REF #:10108014001) at a ratio of 100:1, and then treated with Papain at 37° C. for 1 hour, after which 20 mM IAA (Sigma:A3221) was added thereto, followed by incubation at 37° C. for 45 minutes. The medium was replaced with a buffer containing 20 mM sodium phosphate and 25 mM NaCl (pH7.0) using a HiPrep 26/10 desalting column (GE Healthcare Cat No. 17-5087-01), and then the incubated material was loaded into a Mabselect Sure column (GE Healthcare Cat No. 17-5438-03) to remove the Fc region, and the Fab fragment was concentrated to a concentration of 10 mg/ml using an Amicon ultra centrifugal filter unit (Millipore, REF #:UFC901096). The concentrated Fab fragment was further purified by size exclusion gel filtration chromatography (Superdex200 10/300 GL GE Healthcare, Cat No:17-5175-01) with PBS buffer.

Example 8-3: Co-Crystallization of Antibody Fragment and HA Protein

The Fab fragment of CT120 was in the form of a trimer and was mixed at a ratio of 5:1 with the HA protein of A/Vietnam/1203/04 (H5N1) purified according to the method of Example 7-1, followed by crystallization, and the CT149 Fab fragment was mixed with the HA protein of A.Aichi/2/68 (H3N2) at a ratio of 5:1, followed by crystallization. The produced crystals were separated by size exclusion gel filtration chromatography (Superdex 200 10/30 column; GE Healthcare) using a buffer containing 50 mM Tris-HCl (pH 8.0) and 150 mM NaCl, and were then concentrated to 15 mg/ml and 12 mg/ml, respectively.

Initial sparse-matrix crystallization screening was carried out using a Topaz™ Free Interface Diffusion (FID) Crystallizer system (Fluidigm Corporation, San Francisco, Calif.). Preliminary crystallization conditions for the CT120 Fab-H5 complex were obtained within 24 hours in several conditions containing the precipitant, polyethylene glycol (PEG) 6,000. Through optimization, conditions capable of making a crystal that can be analyzed by diffraction analysis were established. Finally, crystals were grown at 23° C. using the hanging drop vapor diffusion crystallization by mixing 1.0 μL of the CT120/H5 complex with the same volume of 10% PEG 6,000, 100 mM Na cacodylate (pH 6.5) and 400 mM Na formate. A diffraction data set for the CT120 Fab-H5 complex was collected at 4.0 Å resolution at the Advanced Photon Source (APS) SER CAT 22-ID beamline CT120 Fab-H5 was crystallized in the p1 primitive triclinic space group.

Preliminary crystallization conditions for the CT149 Fab-H3 complex were obtained within 24 hours in several conditions containing the precipitant, polyethylene glycol (PEG) 3,000. Through optimization, conditions capable of making a crystal that can be analyzed by diffraction analysis were established. Finally, crystals were grown at 23° C. using the hanging drop vapor diffusion crystallization by mixing 1.0 μL of the CT149 Fab-H3 complex with the same volume of 20% PEG 3,000 and 100 mM Na citrate (pH 5.5). A diffraction data set for the CT149 Fab-H3 complex was collected at 3.5 Å resolution at the Advanced Photon Source (APS) SER CAT 22-ID beamline. CT149 Fab-H3 was crystallized in the $p3_1$ primitive trigonal space group.

Example 8-4: X-Ray Diffraction Analysis

Data collection and refinement statistics are presented in Table 6 below. Data were processed and scaled using HKL2000 and Denzo program. The structures of the CT120 Fab-HA3 complex and the CT149 Fab-HA3 complex were solved by molecular replacement using Phaser program. The solution obtained by molecular replacement was subjected to rigid body and restrained refinement using REFMAC5 program, and model building was performed using Coot. $2F_o\text{-}F_c$ electron density was well defined throughout the model, and restrained refinement of the structure was completed in REFMAC5.

TABLE 6

Data collection and refinement statistics

| | | CT120/H5 | CT149/H3 |
|---|---|---|---|
| Data collection | Space group | P1 | $P3_1$ |
| | Cell dimensions | 146.3Å, 145Å, 260.5Å, 69.9°, 69.9°, 59.9° | 128.7Å, 128.7Å, 428.3Å, 90°, 90°, 120° |
| | Resolution (Å) | 50-4.0 (4.07-4.0) | 50-3.5 (3.50-3.56)* |
| | $R_{sym}$ (%) | 8.2(60.7) | 13.6(71.8) |
| | I/σ | 10.1(1.2) | 11.9(1.7) |
| | Completeness (%) | 98.0(96.4) | 99.5(100) |
| | Redundancy | 2.0(1.9) | 3.7(3.9) |
| Refinement | Resolution (Å) | 239-4.0(4.1-40) | 142.8-3.5(3.49-3.59) |
| | No. of reflections (total) | 132730 | 94527 |
| | No. of reflections (test) | 7050 | 4981 |
| | $R_{work}/R_{free}$ | 28.7/31.1 | 25.9/28.8 |
| | No. of atoms | 88404 | 43357 |
| | r.m.s.d.-bond length (Å) | 0.105 | 0.005 |
| | r.m.s.d.-bond angle (°) | 1.754 | 0.80 |
| MolProbity[#] scores | Favored (%) | 91.0 | 93.3 |
| | Allowed (%) | 98.6 | 99.6 |
| | Outliers (%) $_{(No.\ of\ residues)}$ | 1.4 $_{(153/11202)}$ | 0.4 $_{(21/5450)}$ |

Example 8-5: Validation and Analyses of Structural Data

Residues were numbered in the HA region of the two complexes according to the complete HA1 and HA2 subunits. Structural validation was carried out using Procheck and the RCSB PDB validation server. The connectivity and nomenclature of carbohydrate moieties was validated using PDBCARE (Glycosciences.de) site. Model manipulations, RMSD calculations and distance measurements were carried out using Coot and Pymol. Solvent accessible surface area calculations were carried out using PISA and Protorp.

Example 9: Determination of Site that CT149 Antibody Binds to H7 Subtype HA

In order to determine the binding site of the CT149 antibody of the present invention, on the HA of the H7 subtype (H7N9, A/Anhui/1/2013), the amino acid sequence of HA protein where an antibody fragment binds to was analyzed by X-ray crystallography (FIG. 8*c*).

TABLE 7

Data collection and refinement statistics

| | | CT149/H7 |
|---|---|---|
| Data collection | Space group | R32 |
| | Cell dimensions | 126.9Å, 126.9Å, 409.6Å, 90°, 90°, 120° |
| | Resolution (Å) | 50.0-2.8 (2.9-2.8) |
| | $R_{sym}$ (%) | 11.5 (88.3) |
| | I/σ | 17.2 (2.4) |
| | Completeness (%) | 99.5 (99.9) |
| | Redundancy | 7.8 (7.7) |
| Refinement | Resolution (Å) | 48.4-2.8 (2.9-2.8) |
| | No. of reflections (total) | 31755 |
| | No. of reflections (test) | 1606 |

TABLE 7-continued

Data collection and refinement statistics

| | | CT149/H7 |
|---|---|---|
| | $R_{work}/R_{free}$ | 26.4/31.1 |
| | No. of atoms | 5675 |
| | r.m.s.d.-bond lengths (Å) | 0.004 |
| | r.m.s.d.- Bond angles (°) | 0.780 |
| Ramachandran Plot | favoured regions (%) | 84.5 |
| | allowed regions (%) | 13.9 |
| | Generously allowed regions (%) | 1.6 |
| | Disallowed regions (%) | 0 |

Example 10: Determination of Antigen-Antibody Affinity by Surface Plasmon Resonance Technology The surface plasmon resonance assay (Biacore, Inc.) determines the binding affinity of antibodies with kinetic measurements of on-rate and off-rate constants.

Binding of CT120 and CT149 antibodies to a purified recombinant influenza HA protein was determined by surface plasmon resonance-based measurements with a Biacore T200 (GE Healthcare) using running buffer HBS-EPB (10 mM HEPES [pH 7.4], 150 mM NaCl, 3 mM EDTA, 0.1 mg/ml BSA and 0.005% surfactant P20) at 25° C. Approximately 5000 RU of anti-6× his tag antibody diluted in 10 mM sodium acetate (pH 5.0) was directly immobilized across a CM5 research grade biosensor chip using a standard amine coupling kit according to manufacturer's instructions and procedures at 1 µg/ml. Unreacted moieties on the biosensor surface were blocked with ethanolamine. For kinetic analysis, Biacore T200 control software and Biacore T200 Evaluation software were used. CT120 and CT149 antibodies were diluted in HBS-EP buffer. A recombinant influenza HA protein to be captured as a ligate was injected over reaction matrices at a flow rate of 10 µl/min. During the assay, all measurements were referenced against the capture surface having no captured recombinant influenza HA. The association and dissociation rate constants, Ka ($M^{-1}$ $s^{-1}$) and Kd ($s^{-1}$) were determined at a flow rate of 30 µl/min Rate constants were derived by making kinetic binding measurements at different antigen concentrations ranging from 1.23-100 nM, as a 3-fold dilution series, and included buffer-only injection in order to be used for double referencing. The equilibrium dissociation constant KD (M) of the interaction between antibodies and the target antigen was then calculated from the kinetic rate constants by the following formula: $K_D=Kd/Ka$. Binding is recorded as a function of time and kinetic rate constants are calculated.

The binding affinities of CT120 and CT149 for the purified recombinant HA of various influenza viruses were determined (Tables 8 to 18). CT120 showed a higher affinity for H1 than CT149, but has no affinity for H3. CT149 generally showed high affinities for H3 depending the strain of virus. Both CT120 and CT149 showed high affinities for H5. For H7, CT120 showed no affinity, but CT149 showed high affinity.

TABLE 8

Measurement of binding affinity for HA protein of H1N1 (A/California/04/09)

| | Ka ($M^{-1}s^{-1}$) | Kd ($s^{-1}$) | KD(M) | Average |
|---|---|---|---|---|
| CT120 | 6.15E+05 | 9.94E−04 | 1.62E−09 | 1.62E−09 |
| | 6.31E+05 | 0.001023 | 1.62E−09 | |
| CT149 | 1.29E+06 | 3.88E−02 | 3.02E−08 | 3.06E−08 |
| | 1.29E+06 | 3.99E−02 | 3.10E−08 | |

TABLE 9

Measurement of binding affinity for HA protein of H1N1 (A/Texas/05/09)

| | Ka ($M^{-1}s^{-1}$) | Kd ($s^{-1}$) | KD(M) | Average |
|---|---|---|---|---|
| CT120 | 6.06E+05 | 1.19E−03 | 1.97E−09 | 1.76E−09 |
| | 6.32E+05 | 9.80E−04 | 1.55E−09 | |
| CT149 | 1.66E+06 | 5.58E−02 | 3.36E−08 | 3.38E−08 |
| | 1.65E+06 | 5.62E−02 | 3.41E−08 | |

TABLE 10

Measurement of binding affinity for HA protein of H1N1 (A/Solomon Island/03/06)

| | Ka ($M^{-1}s^{-1}$) | Kd ($s^{-1}$) | KD(M) | Average |
|---|---|---|---|---|
| CT120 | 2.45E+05 | 6.84E−04 | 2.79E−09 | 2.82E−09 |
| | 2.46E+05 | 7.03E−04 | 2.85E−09 | |
| CT149 | 2.46E+05 | 9.04E−02 | 3.68E−07 | 3.45E−07 |
| | 3.24E+05 | 1.05E−01 | 3.23E−07 | |

TABLE 11

Measurement of binding affinity for HA protein of H1N1 (A/Ohio/07/09)

| | Ka ($M^{-1}s^{-1}$) | Kd ($s^{-1}$) | KD(M) | Average |
|---|---|---|---|---|
| CT120 | 3.76E+05 | 6.63E−04 | 1.76E−09 | 2.00E−09 |
| | 3.52E+05 | 7.89E−04 | 2.24E−09 | |
| CT149 | 7.46E+05 | 3.79E−02 | 5.09E−08 | 5.13E−08 |
| | 7.47E+05 | 3.87E−02 | 5.17E−08 | |

TABLE 12

Measurement of binding affinity for HA protein of H3N2 (A/Philippines/2/82)

| | Ka ($M^{-1}s^{-1}$) | Kd ($s^{-1}$) | KD(M) | Average |
|---|---|---|---|---|
| CT149 | 2.92E+05 | 1.47E−05 | 5.02E−11 | 4.56E−11 |
| | 2.85E+05 | 1.17E−05 | 4.11E−11 | |

TABLE 13

Measurement of binding affinity for HA protein of H3N2 (A/Wisconsin/67/05)

| | Ka ($M^{-1}s^{-1}$) | Kd ($s^{-1}$) | KD(M) | Average |
|---|---|---|---|---|
| CT149 | 8.41E+04 | 7.23E−03 | 8.60E−08 | 8.86E−08 |
| | 8.16E+04 | 7.45E−03 | 9.13E−08 | |

TABLE 14

Measurement of binding affinity for HA protein of H3N2 (A/Brisbane/10/07)

| | Ka (M$^{-1}$s$^{-1}$) | Kd (s$^{-1}$) | KD(M) | Average |
|---|---|---|---|---|
| CT149 | 1.73E+05 | 3.19E-04 | 1.85E-09 | 1.81E-09 |
| | 1.79E+05 | 3.16E-04 | 1.77E-09 | |

TABLE 15

Measurement of binding affinity for HA protein of H5N1 (A/Vietnam/1203/04)

| | Ka (M$^{-1}$s$^{-1}$) | Kd (s$^{-1}$) | KD(M) | Average |
|---|---|---|---|---|
| CT120 | 1.13E+09 | 4.23E+00 | 3.74E-09 | 3.97E-09 |
| | 9.24E+08 | 3.88E+00 | 4.20E-09 | |
| CT149 | 1.32E+06 | 3.91E-03 | 2.96E-09 | 2.94E-09 |
| | 1.32E+06 | 3.86E-03 | 2.93E-09 | |

TABLE 16

Measurement of binding affinity for HA protein of H7N7 (A/England/268/96)

| | Ka (M$^{-1}$s$^{-1}$) | Kd (s$^{-1}$) | KD(M) | Average |
|---|---|---|---|---|
| CT149 | 4.01E+05 | 1.76E-03 | 4.40E-09 | 4.41E-09 |
| | 4.06E+05 | 1.80E-03 | 4.43E-09 | |

TABLE 17

Measurement of binding affinity for HA protein of H7N9 (A/Shanghai/1/2013)

| | Ka (M$^{-1}$s$^{-1}$) | Kd (s$^{-1}$) | KD(M) | Average |
|---|---|---|---|---|
| CT149 | 1.97E+07 | 2.80E-03 | 1.42E-10 | 1.49E-10 |
| | 1.83E+07 | 2.85E-03 | 1.55E-10 | |

TABLE 18

Measurement of binding affinity for HA protein of H7N9 (A/Anhui/1/2013)

| | Ka (M$^{-1}$s$^{-1}$) | Kd (s$^{-1}$) | KD(M) | Average |
|---|---|---|---|---|
| CT149 | 1.98E+07 | 3.26E-03 | 1.65E-10 | 1.83E-10 |
| | 1.57E+07 | 3.16E-03 | 2.01E-10 | |

Example 11: Cellular ELISA (CELISA) Assay

The binding affinity of antibodies for HA was analyzed by a CELISA assay using a cell line expressing the H1, H3 or H5 HA. To obtain the H1 expressing cell line, a gene was synthesized using the genetic information of the HA of A/CA/04/09 virus, and then subcloned into an expression vector which was then transfected into a CHO-K1 cell line, after which the H1 expressing cell line was selected. The H3 expressing cell line was obtained using the genetic information of the HA of A/Brisbane/10/07 virus. The H5 expressing cell line was obtained using the genetic information of the HA of A/Vietnam/1203/04 virus. Each of the HA expressing cell lines was cultured in a 5% $CO_2$ humidified incubator at 37° C. using 10% FBS-containing DMEM medium. The cultured cell line was detached from the culture bottle by treating trypsin, and centrifuged after adding culture medium to neutralize the trypsin and then, diluted in culture medium at a concentration of 2×10$^5$ cells/ml. 100 µl of the diluted cells were added to each well of a 96-well plate and cultured in a 5% $CO_2$ humidified incubator 37° C. for 18 hours so as to be attached to the 96-well plate. After culture, each well was washed twice with 200 µl of cold PBS, and then 150 µl of 3.7% formaldehyde solution was added to each well and incubated at room temperature for 15 minutes to fix the cells. Each well was washed three times with 200 µl of PBS containing 0.05% Tween 20, and then blocked with 200 µl of dilution buffer (TEKNOVA, Cat. No. D5120) at room temperature for 60 minutes. The concentration (ug/ml) of each antibody sample (CT120 or CT149) was serially diluted 4-fold with dilution buffer, and then 100 µl of the antibody sample was added to each well and incubated at room temperature for 60 minutes. Each well was washed three times with 200 µl of 0.05% Tween 20-containing PBS buffer, and then 100 µl of a 1:1000 dilution of a HRP-conjugated anti-human kappa chain antibody was added to each well and incubated at room temperature for 40 minutes. Each well was washed three times with 200 µl of 0.05% Tween 20-containing PBS buffer, and then 100 µl of TMB buffer (Sigma, Cat. No. T0440) was added to each well and incubated at room temperature for 6 minutes. Next, 100 µl of 1 N sulfuric acid was added to each well to stop the incubation, and the absorbance at 450 nm was measured.

As a result, CT120 and CT149 did bind to the cell lines expressing the HAs of H1 and H5, respectively, and CT-P27 obtained by mixing CT120 and CT149 at a ratio of 1:1 showed a binding affinity similar to that of each of CT120 and CT149 (FIGS. 9A and 9C). CT149 showed a binding affinity in CELISA performed using the cell line expressing the HA of H3, but CT120 did not bind to the HA of H3. CT-P27 showed a binding affinity similar to that of CT149, suggesting that CT120 did not interfere with the binding of CT149 (FIG. 9B).

Example 12: Neutralizing Activities of Antibodies Before and after Mixing Against Influenza A Virus CT120 and CT149 were mixed with each other at a ratio of 1:1, and the mixture was named "CT-P27". The $EC_{50}$ values of the antibody for various influenza virus subtypes were measured using a modification of the microneutralization test described in Example 4. To measure the $EC_{50}$ values, antibodies were adjusted to an initial concentration of 800-6400 µg/ml, and then serially diluted four-fold to prepare infectious viruses. The absorbance at $OD_{450}$ of each well was measured, and the basis value obtained for the well introduced only with medium was restricted, after which a 4-parameter graph as a function of concentration was plotted using Sigma plot program, and the concentration corresponding to 50% of the maximum absorbance at $OD_{450}$ was calculated, thereby determining $EC_{50}$ values.

$EC_{50}$ is the antibody concentration that shows 50% of the maximal neutralizing activity of the antibody against virus, and a lower $EC_{50}$ value indicates the higher neutralizing activity of the antibody.

As a result, each of CT120 and CT149 showed similar neutralizing abilities against viruses against which they originally showed neutralizing activities, and a mixture of the two antibodies showed effective neutralizing ability without interference with the two antibodies. Thus, the use of the mixture of CT120 and CT149 showed neutralizing effects against all the influenza A viruses of group 1 and group 2 (Table 19).

TABLE 19

Results of measurement of $EC_{50}$ for various influenza A viruses

| Subtype | Virus | $EC_{50}$ (µg/mL) | | |
|---|---|---|---|---|
| | | CT-P22 | CT-P23 | CT-P27 |
| H1N1 | A/PuertoRico/8/34 | 0.33 | W* | 0.67 |
| | A/Texas/05/09-RG15 | 1.19 | W* | 2.05 |
| | A/Solomon Islands/3/2006 | 0.25 | W* | 0.27 |
| | A/Ohio/83 | 0.26 | W* | 0.73 |
| | A/CA/04/09 (mouse adapted) | 1.18 | W* | 2.78 |
| | A/CA/04/09 | 0.21 | NT | 0.62 |
| | A/Ohio/ 07/09 | 0.14 | W* | 0.29 |
| H2N2 | A/Ann Athor/6/60 ca | 6.53 | N** | 12.7 |
| H3N2 | A/Hong Kong/68 (mouse adapted) | N** | 0.76 | 10.8 |
| | A/Philippines/2/82 (mouse adapted) | N** | 0.57 | 1.64 |
| | A/Sydney/5/97 | N** | 2.93 | 6.53 |
| | A/Beijing/32/92-R-H3N2 PR8 | N** | 1.36 | 3.1 |
| | A/Perth/16/09 | N** | 2.06 | 3.99 |
| H5N1 | A/Vietnam/1203/04XPR8 | 3.46 | 212 | 7.29 |
| | A/Anhui/01/2005(H5N1)-PR8 | 6.92 | 11 | 8.02 |
| H7N9 | A/Anhui/1/2013[1] | NT | 0.9 | 2.38 |
| | A/Shanghai/2/2013[1] | NT | 1.17 | 3.55 |
| | A/Shanghai/2/2013[2] | NT | 7.71 | 13.14 |
| H9N2 | A/ck/HK/G9/97(H9N2)/PR8 | 3.12 | 7.39 | 5.09 |

W*: Weak neutralization effect/
N**: No neutralization effect
NT: Not tested/To be tested
[1]Tested in Contract Lab A
[2]Tested in Contract Lab B

Example 13: Examination of Preventive and Therapeutic Effects of Antibody Mixture Against Influenza A Virus by Animal Test In order to examine whether administration of CT120 and CT149 antibodies alone or in a mixture shows preventive and therapeutic effects against influenza A virus in mice, the survival rate of mice was examined. Each group consisting of 5-10 mice was intranasally infected with 5-10 $LD_{50}$ of influenza virus. The antibody was administered to the mice by intraperitoneal injection in an amount of 7.5, 15 30 mg/kg at 24 hours before viral infection or at 24 hours after viral infection. CT-P27 was a 1:1 mixture of CT120 and CT149 and the total amount thereof is indicated, and thus the amount of each of CT120 and CT149 in the antibody mixture was equal to half of the indicated amount.

As a result, CT-P27 maintained the effect of each of CT120 and CT149 antibodies and did not show the interference between the antibodies.

13-1: Preventive and Therapeutic Effects of Antibody Mixture Against H1N1

Each group consisting of 5-10 mice was intranasally infected with 5-10 $LD_{50}$ of A/Califomia/04/09. The antibody was administered to the mice by intraperitoneal injection at 24 hours before viral infection or at 24 hours after viral infection, and the survival rate of the mice was measured.

As a result, as shown in FIG. 10, when the CT120, CT149 or CT-P27 antibody was administered at 24 hours before viral infection, all the mice did survive for the period of the experiment in a manner independent of the concentration of the antibody. When the antibody was administered at 24 hours after viral infection, the survival rate of the mice administered with the CT120, CT149 or CT-P27 antibody increased as the concentration of the antibody increased. The survival rate of the mice administered with CT120 was slightly higher than that of the mice administered with CT149. CT-P27 showed a survival rate similar to the sum of survival rates shown by CT120 and CT149 (additive effect), indicating that the decrease in effects by the mixing of the antibodies did not occur.

13-2: Preventive and Therapeutic Effects of Antibody Mixture Against H3N2

Each group consisting of 5-10 mice was intranasally infected with 10 $LD_{50}$ of A/Brisbane/10/07 or 5 $LD_{50}$ of A/Philippines/2/82. The antibody was administered to the mice by intraperitoneal injection at 24 hours before viral infection or at 24 hours after viral infection, and the survival rate of the mice was measured.

As a result, as shown in FIG. 11, when each of the antibodies was administered at 24 hours before viral infection, CT120 did not contribute to the increase in the survival rate of the mice, whereas all the mice administered with CT149 or CT-P27 did survive for the period of the experiment in any concentration of the antibody tested. When each of the antibodies was administered at 24 hours after infection with A/Philippines/2/82 virus, the CT120 antibody did not contribute to the increase in the survival rate of the mice, whereas CT149 and CT-P27 showed the increase in the survival rate as an increase in the concentration thereof. CT-P27 showed a survival rate corresponding to the concentration of the CT149 antibody thereof, indicating that there was no interference between CT120 and CT149 in the antibody mixture.

13-3: Therapeutic Effect of Antibody Mixture Against H5N1

Each group consisting of 5-10 mice was intranasally infected with 10 $LD_{50}$ of A/Vietnam/1203/04 virus. The antibody was administered to the mice by intraperitoneal injection at 24 hours after viral infection, and the survival rate of the mice was measured.

As a result, as shown in FIG. 12, when the mice were administered with the antibody at 24 hours after infection with A/Vietnam/1203/04 virus, all the mice did survive for the period of the experiment in any concentration of the antibody tested.

13-4: Therapeutic Effect of CT149 Antibody Against H7N9

Each group consisting of 10 mice was intranasally infected with $10^6$ PFU of A/Anhui/1/2013 virus. The antibody was administered to the mice by intraperitoneal injection at 24 hours after viral infection, and the survival rate of the mice was measured.

As a result, as shown in FIG. 13, when the negative control antibody was administered, the mice started to die 3 days after administration, and almost all died after 7 days. However, the survival rate of the mice administered with the CT149 antibody at 24 hours after viral infection increased as the concentration of the antibody increased.

Example 14: Effect of Administration of Antibody Mixture in Combination with Chemical Compound Each group consisting of 5 mice was intranasally infected with 5 LD$_{50}$ of mouse adapted A/CA/04/09 virus or 5 LD$_{50}$ of A/Philippines/2/82 virus. At 24 hours after viral infection, the neuraminidase inhibitor Peramivir was administered once (×1) over five consecutive days (×5) to the mice by intraperitoneal injection. Alternatively, varying concentrations of the antibodies were administered alone or in combination with Peramivir, and the survival rate was measured.

As a result, as shown in FIG. 14A, when 15 mg of Peramivir or 1 mg of CT120 was administered alone to the mice at 24 hours after infection with A/CA/04/09 virus, the survival rates of the mice were 40% and 20%, respectively, but when 15 mg of Peramivir and 1 mg of CT120 administered in combination, the survival rate of the mice was as high as 80%. Similarly, as shown in FIG. 14B, when 15 mg of Peramivir was administered alone at 24 hours after infection with A/Philippines/2/82 virus, a survival rate of 40% appeared, and when 1 mg of CT149 was administered alone, all the mice died on day 8. However, administration of CT149 in combination with Peramivir showed a survival rate as high as 80%. Administration of the antibody or Peramivir alone showed high death rate, because the concentration of the antibody or Peramivir is not an optimized concentration, whereas administration of the antibody in combination with Peramivir showed a synergistic effect.

Example 15: Neutralizing Effect of Antibody Mixture Against Neuraminidase Inhibitor-Resistant H7N9 Mutant R292K For A/Shanghai/2/2013 virus and A/Anhui/1/2013 virus, the abilities of CT149 (CT-P23) and CT-P27 to the infectivity of the viruses were analyzed by an in vitro neutralization assay. The analysis was performed as described in Example 4, and the results of the analysis are shown in FIG. 15. CT149 and CT-P27 all showed the ability to neutralize the viruses, and the IC50 values thereof are shown in FIG. 15.

For A/Shanghai/1/2013 (wild type) virus and its mutant (R292K), the abilities of the antibodies to neutralize the viruses were also analyzed by an in vitro neutralization assay. The analysis was performed as described in Example 4, and the results of the analysis are shown in FIGS. 16*a* and 16*b*. CT149 and CT-P27 all showed the ability to neutralize the viruses, and the IC50 values thereof are shown in Table 20 below.

TABLE 20

Abilities (IC50) of CT149 and CT-P27 to neutralize A/Shanghai/1/2013 (wild type) and its mutant

| Virus strain | type | CT-P23 | CT-P27 |
|---|---|---|---|
| A/Shanghai/1/2013 | Wild type | 7.705 | 13.14 |
| A/Shanghai/1/2013 | R292K | 14.87 | 16.28 |

* unit: ug/mL

Example 16: Neutralizing Effect of Antibody Mixture Against Neuraminidase Inhibitor-Resistant H1N1 Mutant H275Y CT120 (CT-P22) and CT149 (CT-P23) were mixed with each other at a ratio of 1:1, and the mixture was named "CT-P27". The $EC_{50}$ values of CT120 and CT-P27 for neuraminidase inhibitor-resistant H1N1 mutant H275Y were measured the microneutralization test described in Example 4. To measure the $EC_{50}$ values, antibodies were adjusted to initial concentrations of 800 μg/ml for CT120 and 400 μg/ml for CT-P27, and then serially diluted 4-fold. The absorbance at $OD_{450}$ of each well was measured, and the basis value obtained for the well introduced only with medium was restricted, after which a 4-parameter graph as a function of concentration was plotted using Sigma plot program, and the concentration corresponding to 50% of the maximum absorbance at $OD_{450}$ was calculated, thereby determining $EC_{50}$ values.

$EC_{50}$ is the antibody concentration that shows 50% of the maximal neutralizing activity of the antibody against virus, and a lower $EC_{50}$ value indicates the higher neutralizing activity of the antibody.

As a result, as shown in FIGS. 17*a* and 17*b*, each of CT120 and CT-P27 showed the ability to neutralize the neuraminidase inhibitor-resistant H1N1 mutant H275Y virus, and particularly, the mixture (CT-P27) of the two antibodies showed the ability to neutralize the mutant virus, without interference between the two antibodies.

Example 17: Binding Affinity of Antibody Mixture for HA Mutant

As reported in the literature, similar to CT149, CR8020 antibody showing neutralizing effects against the influenza viruses of group 2 showed a low binding affinity for naturally occurring HA D19N mutants (Ekiert D C. et. al. 2011, Science 333(6044):843-50). Accordingly, a D19N mutation was artificially introduced into the HA of each of A/Wisconsin/67/05 (H3N2) and A/Anhui/1/2013 (H7N9), for which CT149 has binding affinity, to prepare HA-expressing CHO cell lines. Immunofluorescent staining of the cell lines was performed using CT149.

As a result, CT120 having no binding affinity did not stain the CHO cells, whereas CT149 easily stained not only the wild-type CHO cells, but also the HA-expressing CHO cells introduced with the D19N mutation (FIGS. 18*a* and 18*b*).

The invention claimed is:

1. A composition comprising at least two influenza A virus-neutralizing binding molecules that bind to an epitope in a stem region of influenza A virus hemagglutinin (HA) protein, the composition comprising:

i) a first binding molecule capable of neutralizing at least one influenza A virus subtype selected from the group consisting of H1, H2, H5 and H9;
wherein the first binding molecule comprises any one polypeptide selected from the group consisting of:

i) a polypeptide comprising a light-chain variable region comprising, as determined according to the Kabat method, a CDR1 region of SEQ ID NO: 1, a CDR1 region of SEQ ID NO: 2 and a CDR3 region of SEQ ID NO: 3, and a heavy-chain variable region comprising, as according to the Kabat method, a CDR1 region of SEQ ID NO: 4, a CDR2 region of SEQ ID NO: 5 and a CDR3 region of SEQ ID NO: 6;

ii) a polypeptide comprising a light-chain variable region comprising, as determined according to the Kabat method, a CDR1 region of SEQ ID NO: 7, a CDR2 region of SEQ ID NO: 8 and a CDR3 region of SEQ ID NO: 9, and a heavy-chain variable region comprising, as according to the Kabat method, a CDR1 region of SEQ ID NO: 10, a CDR2 region of SEQ ID NO: 11 and a CDR3 region of SEQ ID NO: 12; and iii) a polypeptide comprising a light-chain variable region comprising, as determined according to the Kabat method, a CDR1 region of SEQ ID NO: 13, a CDR2 region of SEQ NO: 14 and a CDR3 region of SEQ ID NO: 15, and a heavy-chain variable region comprising, as according to the Kabat method, a CDR1 region of SEQ ID NO: 16, a CDR2 region of SEQ ID NO: 17 and a CDR3 region of SEQ ID NO: 18; and ii) a second binding molecule capable of neutralizing at least one influenza A virus subtype selected from the group consisting of H1, H3, H5, H7 and H9, wherein the second binding molecule comprises any one polypeptide selected from the group consisting of:

i) a polypeptide comprising a light-chain variable region comprising, as determined according to the Kabat method, a CDR1 region of SEQ ID NO: 19, a CDR2 region of SEQ ID NO: 20 and a CDR3 region of SEQ ID NO: 21, and a heavy-chain variable region comprising, as according to the Kabat method, a CDR1 region of SEQ ID NO: 22, a CDR2 region of SEQ NO: 23 and a CDR3 region of SEQ ID NO: 24;

ii) a polypeptide comprising a light-chain variable region comprising, as determined according to the Kabat method, a CDR1 region of SEQ ID NO: 25, a CDR2 region of SEQ ID NO: 26 and a CDR3 region of SEQ ID NO: 27, and a heavy-chain variable region comprising, as according to the Kabat method, a CDR1 region of SEQ ID NO: 28, a CDR2 region of SEQ ID NO: 29 and a CDR3 region of SEQ ID NO: 30;

iii) a polypeptide comprising a light-chain variable region comprising, as determined according to the Kabat method, a CDR1 region of SEQ ID NO: 31, a CDR2 region of SEQ ID NO: 32 and a CDR3 region of SEQ ID NO: 33, and a heavy-chain variable region comprising, as according to the Kabat method, a CDR1 region of SEQ ID NO: 34, a CDR2 region of SEQ ID NO: 35 and a CDR3 region of SEQ ID NO: 36; and iv) a polypeptide comprising a light-chain variable region comprising, as determined according to the Kabat method, a CDR1 region of SEQ ID NO: 37, a CDR2 region of SEQ ID NO: 38 and a CDR3 region of SEQ ID NO: 39, and a heavy-chain variable region comprising, as according to the Kabat method, a CDR1 region of SEQ ID NO: 40, a CDR2 region of SEQ ID NO: 41 and a CDR3 region of SEQ ID NO: 42; and wherein the first and second binding molecules are produced by a CHO cell culture.

2. The composition of claim 1, wherein the first binding molecule binds to the epitope that comprises amino acid residues at positions 18, 38, 40, 291, 292 and 318 of an HA1 polypeptide of influenza A virus, and comprises amino acid residues at positions 18, 19, 20, 21, 41, 42, 45, 48, 49, 52 and 53 of an HA2 polypeptide of influenza A virus wherein the numbering of the amino acid positions of the epitope is based on H3 HA numbering.

3. The composition of claim 1, wherein the composition is capable of neutralizing an H1N1 mutation having a histidine (His)-to-tyrosine (Tyr) substitution at position 275 of a neuraminidase polypeptide.

4. The composition of claim 1, wherein the composition is capable of neutralizing an H7N9 mutation having an arginine (Arg)-to-lysine (Lys) substitution at position 292 of a neuraminidase polypeptide.

5. The composition of claim 1, wherein the binding molecules inhibit membrane fusion between the virus and a target cell.

6. The composition of claim 1, wherein the first binding molecule has a binding affinity ($K_D$) of less than $1 \times 10^{-8}$ M.

7. The composition of claim 1, wherein the second binding molecule has a binding affinity ($K_D$) of less than $1 \times 10^{-6}$ M.

8. The composition of claim 1, wherein the first binding molecule has an $EC_{50}$ value of 2.0 ug/ml or less for H1 subtype, 7.0 ug/ml or less for H2 subtype, 7.0 ug/ml or less for H5 subtype, or 4.0 ug/ml or less for H9 subtype.

9. The composition of claim 1, wherein the second binding molecule has an $EC_{50}$ value of 40.0 ug/ml or less for H3 subtype, 212.0 ug/ml or less for H5 subtype, 8.0 ug/ml or less for H7 subtype, or 8.0 ug/ml or less for H9 subtype.

10. The composition of claim 1, wherein the composition has an $EC_{50}$ value of 3.0 ug/ml or less for H1 subtype, 13.0 ug/ml or less for H2 subtype, 70.0 ug/ml or less for H3 subtype, 9.0 ug/ml or less for H5 subtype, 1.4.0 ug/ml or less for H7 subtype, or 6.0 ug/ml or less for H9 subtype.

11. The composition of claim 1, wherein the first binding molecule comprises any one polypeptide selected from the group consisting of:

a polypeptide comprising a light chain comprising a polypeptide sequence of SEQ ID NO: 43 and a heavy chain comprising a polypeptide sequence of SEQ ID NO: 44;

a polypeptide comprising a light chain comprising a polypeptide sequence of SEQ ID NO: 45 and a heavy chain comprising a polypeptide sequence of SEQ ID NO: 46; and a polypeptide comprising a light chain comprising a polypeptide sequence of SEQ ID NO: 47 and a heavy chain comprising a polypeptide sequence of SEQ ID NO: 48.

12. The composition of claim 1, wherein the second binding molecule comprises any one polypeptide selected from the group consisting of:

a polypeptide comprising a light chain comprising a polypeptide sequence of SEQ ID NO: 49 and a heavy chain comprising a polypeptide sequence of SEQ ID NO: 50;

a polypeptide comprising a light chain comprising a polypeptide sequence of SEQ ID NO: 51 and a heavy chain comprising a polypeptide sequence of SEQ ID NO: 52;

a polypeptide comprising a light chain comprising a polypeptide sequence of SEQ ID NO: 53 and a heavy chain comprising a polypeptide sequence of SEQ ID NO: 54; and a polypeptide comprising a light chain comprising a polypeptide sequence of SEQ ID NO: 55 and a heavy chain comprising a polypeptide sequence of SEQ ID NO: 56.

13. The composition of claim 1, wherein
the first binding molecule comprises: a light-chain variable region comprising, as determined according to the Kabat method, a CDR1 region of SEQ ID NO: 7, a CDR2 region of SEQ ID NO: 8 and a CDR3 region of SEQ ID NO: 9; and a heavy-chain variable region comprising, as determined according to the Kabat method, a CDR1 region of SEQ ID NO: 10, a CDR2 region of SEQ ID NO: 11 and a CDR3 region of SEQ ID NO: 12; and
the second binding molecule comprises: a light-chain variable region comprising, as determined according to the Kabat method, a CDR1 region of SEQ ID NO: 25, a CDR2 region of SEQ ID NO: 26 and a CDR3 region of SEQ ID NO: 27; and a heavy-chain variable region comprising, as determined according to the Kabat method, a CDR1 region of SEQ ID NO: 28, a CDR2 region of SEQ ID NO: 29 and a CDR3 region of SEQ ID NO: 30.

14. The composition of claim 1, wherein
the first binding molecule comprises a light chain comprising a polypeptide sequence of SEQ ID NO: 45 and a heavy chain comprising a polypeptide sequence of SEQ ID NO: 46, and
the second binding molecule comprises a light chain comprising a polypeptide sequence of SEQ ID NO: 51 and a heavy chain comprising a polypeptide sequence of SEQ ID NO: 52.

15. The composition of claim 1, wherein the binding molecule is an antibody or an antigen binding fragment thereof.

16. The composition of claim 15, wherein an antiviral drug is further attached to the antibody.

17. The composition of claim 1, wherein the composition is for diagnosing, preventing or treating a disease caused by influenza virus.

18. The composition of claim 1, wherein the composition is in the form of a sterile injectable solution, a lyophilized formulation, a pre-filled syringe solution, an oral dosage form, a formulation for external use, or a suppository.

19. A kit for diagnosing influenza virus, the kit comprising:
   i) a composition for diagnosing influenza virus according to claim 17; and
   ii) a container.

20. The composition of claim 1, wherein the second binding molecule binds to the epitope that comprises amino acid residues at positions 278 and 318 of an HA1 polypeptide of influenza A virus, and comprises amino acid residues at positions 38, 39, 41, 42, 45, 48, 49, 52 and 53 of an HA2 polypeptide of influenza A virus;
   wherein the numbering of the amino acid positions of the epitope is based on H3 HA numbering.

21. The composition of claim 1, wherein the epitope to which the second binding molecule binds comprises amino acid residues at the positions of the HA1 polypeptide and HA2 polypeptide of a first monomer of HA, and further comprises amino acid residues at positions 25, 32 and 33 of the HA' polypeptide of a second monomer of HA adjacent to the first monomer of HA;
   wherein the numbering of the amino acid positions of the epitope is based on H3 HA numbering.

22. The composition of claim 1, wherein the epitope to which the second binding molecule binds further comprises amino acid residues at positions 58 and 99 of the HA2 polypeptide;
   wherein the numbering of the amino acid positions of the epitope is based on H3 HA numbering.

23. The composition of claim 21, wherein the epitope to which the second binding molecule binds further comprises an amino acid residue at position 27 of the HA1 polypeptide of the second monomer adjacent to the first monomer;
   wherein the numbering of the amino acid positions of the epitope is based on H3 HA numbering.

24. The composition of claim 1, wherein the epitope to which the second binding molecule binds further comprises amino acid residues at positions 54, 55 and 291 of the HA1 polypeptide, and amino acid residues at positions 19, 20, 21, 46, 56, 57 and 60 of the HA2 polypeptide;
   wherein the numbering of the amino acid positions of the epitope is based on H3 HA numbering.

25. The composition of claim 21, wherein the epitope to which the second binding molecule binds further comprises amino acid residues at positions of 310, 311 and 312 of the HA1 polypeptide of the second monomer of HA adjacent to the first monomer of HA;
   wherein the numbering of the amino acid positions of the epitope is based on H3 HA numbering.

* * * * *